US008945562B2

(12) United States Patent
Van Vlasselaer et al.

(10) Patent No.: US 8,945,562 B2
(45) Date of Patent: *Feb. 3, 2015

(54) ANTI-COMPLEMENT C1S ANTIBODIES

(71) Applicant: True North Therapeutics, Inc., South San Francisco, CA (US)

(72) Inventors: Peter Van Vlasselaer, Portola Valley, CA (US); Graham Parry, South San Francisco, CA (US); Nancy E. Stagliano, South San Francisco, CA (US); Sandip Panicker, South San Francisco, CA (US)

(73) Assignee: True North Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/070,186

(22) Filed: Nov. 1, 2013

(65) Prior Publication Data

US 2014/0140933 A1 May 22, 2014

Related U.S. Application Data

(60) Provisional application No. 61/846,402, filed on Jul. 15, 2013, provisional application No. 61/779,180, filed on Mar. 13, 2013, provisional application No. 61/754,123, filed on Jan. 18, 2013, provisional application No. 61/721,916, filed on Nov. 2, 2012.

(51) Int. Cl.
*A61K 39/395* (2006.01)
*C07K 16/00* (2006.01)
*C07K 16/36* (2006.01)
*C07K 16/40* (2006.01)
*C07K 16/18* (2006.01)
*A61K 39/00* (2006.01)

(52) U.S. Cl.
CPC ............... *C07K 16/40* (2013.01); *C07K 16/18* (2013.01); *A61K 2039/505* (2013.01); *C07K 2317/24* (2013.01); *C07K 2317/35* (2013.01); *C07K 2317/54* (2013.01); *C07K 2317/55* (2013.01); *C07K 2317/76* (2013.01); *C07K 2317/92* (2013.01)
USPC .................. 424/145.1; 424/130.1; 424/133.1; 424/141.1; 424/158.1; 530/387.1; 530/387.3; 530/388.1; 530/388.2; 530/388.22

(58) Field of Classification Search
None
See application file for complete search history.

(56) References Cited

U.S. PATENT DOCUMENTS

| | | | |
|---|---|---|---|
| 4,945,039 A | 7/1990 | Suzuki et al. | |
| 6,090,777 A | 7/2000 | Hack et al. | |
| 7,049,282 B2 | 5/2006 | Frank et al. | |
| 7,071,299 B2 | 7/2006 | West et al. | |
| 7,666,627 B2 | 2/2010 | Gál et al. | |
| 7,897,561 B2 | 3/2011 | Kotwal et al. | |
| 7,919,094 B2 | 4/2011 | Schwaeble et al. | |
| 7,923,010 B2 | 4/2011 | Christadoss et al. | |
| 8,071,532 B2 | 12/2011 | Mannesse et al. | |
| 8,148,330 B2 | 4/2012 | Barres et al. | |
| 8,221,756 B2 | 7/2012 | Fung et al. | |
| 8,329,169 B2 | 12/2012 | Fung et al. | |
| 8,415,288 B2 | 4/2013 | Mannesse et al. | |
| 8,501,705 B2 | 8/2013 | Christadoss et al. | |
| 8,545,850 B2 | 10/2013 | Chen et al. | |
| 2002/0037915 A1 | 3/2002 | Illig et al. | |
| 2002/0102256 A1 | 8/2002 | West et al. | |
| 2005/0004031 A1 | 1/2005 | Subasinghe et al. | |
| 2005/0032157 A1 | 2/2005 | Gal et al. | |
| 2005/0222027 A1 | 10/2005 | Chiang et al. | |
| 2005/0267035 A1 | 12/2005 | West et al. | |
| 2005/0271660 A1 | 12/2005 | Wang | |
| 2006/0002937 A1 | 1/2006 | Schwaeble et al. | |
| 2006/0018896 A1 | 1/2006 | Schwaeble et al. | |
| 2006/0148015 A1 | 7/2006 | Roos et al. | |
| 2007/0172483 A1 | 7/2007 | Schwaeble et al. | |
| 2009/0259019 A1 | 10/2009 | Willis et al. | |
| 2009/0269356 A1 | 10/2009 | Epstein et al. | |
| 2009/0324585 A1 | 12/2009 | Robinson et al. | |
| 2010/0074899 A1 | 3/2010 | Schwaeble et al. | |
| 2010/0143343 A1 | 6/2010 | Halstead et al. | |
| 2010/0143344 A1 | 6/2010 | Baas et al. | |
| 2010/0166862 A1 | 7/2010 | Francois et al. | |
| 2011/0020337 A1 | 1/2011 | Schwaeble et al. | |
| 2011/0091450 A1 | 4/2011 | Schwaeble et al. | |
| 2011/0104156 A1 | 5/2011 | Christadoss et al. | |
| 2011/0190221 A1 | 8/2011 | Francois et al. | |
| 2011/0281757 A1 | 11/2011 | Tyan et al. | |
| 2011/0311549 A1 | 12/2011 | Schwaeble et al. | |

(Continued)

FOREIGN PATENT DOCUMENTS

WO    WO01/57079       8/2001
WO    WO03/009803      2/2003
WO    WO2013/093027    6/2013

OTHER PUBLICATIONS

Carroll, "Strategies for Generating Therapeutic Antibodies", Dissertation, The University of Texas at Austin, 2012.
An et al., "IgG2m4, an engineered antibody isotype with reduced Fc function", mAbs, 2009, 1(6):572-579.
Anti-Complement C1s Antibody, Cat# LS-C121168, LifeSpan Biosciences, http://www.lsbio.com/antibodies/anti-complement-c1s-antibody-mouse-anti-human-monoclonal-for-ihc-western-blot-ls-c121168/124626, See attached datasheet.
Anti-Complement C1s Antibody (aa1-688), Cat# LS-C128271, LifeSpan Biosciences, http://www.lsbio.com/antibodies/anti-complement-c1s-antibody-aa1-688-mouse-anti-human-polyclonal-for-western-blot-ls-c128271/131891, See attached datasheet.

(Continued)

*Primary Examiner* — Phillip Gambel
(74) *Attorney, Agent, or Firm* — Paula A. Borden; Bozicevic, Field & Francis LLP.

(57) ABSTRACT

The present disclosure provides antibodies that bind complement C1s protein; and nucleic acid molecules that encode such antibodies. The present disclosure also provides compositions comprising such antibodies, and methods to produce and use such antibodies, nucleic acid molecules, and compositions.

47 Claims, 49 Drawing Sheets

(56) References Cited

U.S. PATENT DOCUMENTS

| | | |
|---|---|---|
| 2011/0312505 A1 | 12/2011 | Reddy et al. |
| 2012/0195880 A1 | 8/2012 | Barres et al. |
| 2012/0225056 A1 | 9/2012 | Rother et al. |
| 2012/0230953 A1 | 9/2012 | Goldenberg et al. |
| 2012/0244139 A1 | 9/2012 | Madison et al. |
| 2012/0251549 A1 | 10/2012 | Fung et al. |
| 2012/0258095 A1 | 10/2012 | Demopulos et al. |
| 2012/0263717 A1 | 10/2012 | Dennis et al. |
| 2012/0282263 A1 | 11/2012 | Dudler et al. |
| 2012/0315266 A1 | 12/2012 | Olson et al. |
| 2012/0328601 A1 | 12/2012 | Barres et al. |
| 2013/0064820 A1 | 3/2013 | Magro |
| 2013/0078245 A1 | 3/2013 | Holers et al. |
| 2013/0123473 A1 | 5/2013 | Goldenberg et al. |
| 2013/0202612 A1 | 8/2013 | Lin et al. |
| 2013/0203678 A1 | 8/2013 | Francois et al. |
| 2013/0224187 A1 | 8/2013 | Rother et al. |
| 2013/0237589 A1 | 9/2013 | Benedict et al. |
| 2013/0244941 A1 | 9/2013 | Massesse et al. |
| 2013/0259860 A1 | 10/2013 | Smith et al. |
| 2013/0261287 A1 | 10/2013 | Sabbadini et al. |
| 2013/0273052 A1 | 10/2013 | Gies et al. |

OTHER PUBLICATIONS

Anti-Complement C1s Antibody [clone M81], Cat# LS-C140039, LifeSpan Biosciences, http://www.lsbio.com/antibodies/anti-complement-c1s-antibody-clone-m81-mouse-anti-human-monoclonal-for-ihc-western-blot-ls-c140039/144752, See attached datasheet.
Anti-Complement C1s Antibody (Internal) [clone EPR9067(B)], Cat# LS-C154704, LifeSpan Biosciences, http://www.lsbio.com/antibodies/anti-complement-c1s-antibody-internal-clone-epr9067b-rabbit-anti-human-monoclonal-for-western-blot-ls-c154704/161379, See attached datasheet.
Anti-Complement C1s Antibody (Internal) [clone EPR9066(B)], Cat# LS-C154717, LifeSpan Biosciences, http://www.lsbio.com/antibodies/anti-complement-c1s-antibody-internal-clone-epr9066b-rabbit-anti-human-monoclonal-for-ihc-western-blot-ls-c154717/161392, See attached datasheet.
Anti-Complement C1s Antibody [clone 4D9], Cat# LS-C173424, LifeSpan Biosciences, http://www.lsbio.com/antibodies/anti-complement-c1s-antibody-clone-4d9-mouse-anti-human-monoclonal-for-western-blot-ls-c173424/180848, See attached datasheet.
Anti-Complement C1s Antibody [clone 2F5], Cat# LS-C173425, LifeSpan Biosciences, http://www.lsbio.com/antibodies/anti-complement-c1s-antibody-clone-2f5-mouse-anti-human-monoclonal-for-western-blot-ls-c173425/180849, See attached datasheet.
Anti-Complement C1s Antibody [clone 4D10], Cat# LS-C173540, LifeSpan Biosciences, http://www.lsbio.com/antibodies/anti-complement-c1s-antibody-clone-4d10-mouse-anti-human-monoclonal-for-western-blot-ls-c173540/180964, See attached datasheet.
Anti-Complement C1s Antibody [clone 5F2], Cat# LS-C173718, LifeSpan Biosciences, http://www.lsbio.com/antibodies/anti-complement-c1s-antibody-clone-5f2-mouse-anti-human-monoclonal-for-ihc-western-blot-ls-c173718/181142, See attached datasheet.
Anti-Complement C1s Antibody [clone 2D11], Cat# LS-C173719, LifeSpan Biosciences, http://www.lsbio.com/antibodies/anti-complement-c1s-antibody-clone-2d11-mouse-anti-human-monoclonal-for-ihc-western-blot-ls-c173719/181143, See attached datasheet.
Anti-Complement C1s Antibody [clone 2A8], Cat# LS-C173720, LifeSpan Biosciences, http://www.lsbio.com/antibodies/anti-complement-c1s-antibody-clone-2a8-mouse-anti-human-monoclonal-for-ihc-western-blot-ls-c173720/181144, See attached datasheet.
Anti-Complement C1s Antibody, Cat# LS-C6208, LifeSpan Biosciences, http://www.lsbio.com/antibodies/anti-complement-c1s-antibody-mouse-anti-human-monoclonal-ls-c6208/6949, See attached datasheet.
Anti-Complement C1s Antibody [clone 49], Cat# LS-C6209, LifeSpan Biosciences, http://www.lsbio.com/antibodies/anti-complement-c1s-antibody-clone-49-mouse-anti-human-monoclonal-ls-c6209/6950, See attached datasheet.
Basiglio et al., "Complement activation and disease: protective effects of hyperbilirubinaemia", Clinical Science, 2010, 118:99-113.
Brahmi et al., "Synergistic inhibition of human cell-mediated cytotoxicity by complement component antisera indicates that target cell lysis may result from an enzymatic cascade involving granzymes and perforin", Nat. Immun., 1995, 14:271-285.
Carroll et al., "Antibody-mediates inhibition of human C1s and the classical complement pathway", Immunobiol., 2013, 218:1041-1048.
Gal et al., "C1s, the protease messenger of C1. Structure, function and physiological significance", Immunoniol, 2002, 205:383-394.
Gal et al., "Early complement proteases: C1r, C1s and MASPs. A structural insight into activation and functions", Molec. Immuno., 2009, 46:2745-2752.
Hamad et al., "Complement activation by PEGylated single-walled carbon nanotubes is independent of C1q and alternative pathway turnover", Mol. Immunol., 2008, 45(14):3797-3803.
Heinz et al., "Monoclonal antibodies against components of the classical pathway of complement", Complement Inflamm., 1989, 6:166-174.
Kidmose, et al., "Structural Basis for Activation of the Complement System by Component C4 Cleavage", PNAS, 2012, vol. 109, No. 38, pp. 15425-15430.
Matsumoto et al., "Acceleration of site-to-site transfer of C1—by a monoclonal antibody to C1-S", Mol. Immunol., 1989, 26:697-703.
Matsumoto et al., "Functional analysis of activated C1s, a subcomponent of the first component of human complement, by monoclonal antibodies", J. Immunol., 1986, 137:2907-2912.
Matsumoto et al., "Probing the C4-binding site on C1s with monoclonal antibodies. Evidence for a C4/C4b-binding site on the gamma-domain.", J. Immunol., 1989, 142:2743-2750.
Nagaki et al., "Specific antisera to C1s: detection of different electrophoretic species of C1s", J. Immunol., 1969, 103:141-145.
Nakagawa et al., "Complement C1s activation in degenerating articular cartilage of rheumatoid arthritis patients: immunohistochemical studies with an active form specific antibody", Ann. Rheum. Dis., 1999, 58:175-181.
Nakagawa et al., "Coordinated change between complement C1s production and chondrocyte differentiation in vitro", Cell Tissue Res., 1997, 289:299-305.
"Phuan, et al., ""C1q-targeted monoclonal antibody prevents complement-dependent cytotoxicity and neuropathology in in vitro and mouse models of neuromyelitis optica"", Acta Neuropathol, 2013, vol. 125, pp. 829-840."
Rossi, et a. "Baculovirus-mediated expression of truncated modular fragments from the catalytic region of human complement serine protease C1s. Evidence for the involvement of both complement control protein modules in the recognition of the C4 protein substrate", . J. Biol. Chem., 1998, 273, 1232-1239.
Reddy et al., "Elimination of Fc receptor-dependent effector functions of a modified IgG4 monoclonal antibody to human CD4", J Immunol., 2000, 164:1925-1933.
Sakiyama et al., "Biochemical characterization and tissue distribution of hamster complement C1s", J. Immunol., 1991, 146:183-187.
Sakiyama et al., "Complement C1s, a classsical enzyme with novel functions at the endochondral ossification center: immunohistochemical staining of activated C1s with a neoantigen-specific antibody", Cell Tissue Res., 1997, 288:557-565.
Sakiyama et al., "Site-directed mutagenesis of hamster complement C1s: characterization with an active form-specific antibody and possible involvement of C1s in tumorigenicity", Int. J. Cancer, 1996, 66:768-771.
Thielens et al., "Comparative study of the fluid-phase proteolytic cleavage of human complement subcomponents C4 and C2 by C1s and C1r2-C1s2", FEBS, 1984, 165(1):111-116.

(56) References Cited

OTHER PUBLICATIONS

Tseng et al., "Probing the structure of C1 with an anti-C1s monoclonal antibody: the possible existence of two forms of C1 in solution", Mol. Immunol., 1997, 34:671-679.

Veerhuis et al., "Early complement components in Alzhemier's disease brains", Acta Neuropathol., 1996, 91:53-60.

Wines et al., "The IgG Fc contains distinct Fc receptor (FcR) binding sites: The leukocyte receptors FcyRI and FcyRlla bind to a region in the Fc distinct from that recognized by neonatal FcR and Protein A", J Immunol., 2000, 164:5313-5318.

Figure 1

EPTMYGEILSPNYPQAYPSEVEKSWDIEVPEGYGIHLYFTHLDIELSENCAYDSVQIISG
DTEEGRLCGQRSSNNPHSPIVEEFQVPYNKLQVIFKSDFSNEERFTGFAAYVATDINEC
TDFVDVPCSHFCNNFIGGYFCSCPPEVFLHDDMKNCGVNCSGDVFTALIGEIASPNYPKP
YPENSRCEYQIRLEKGFQVVVTLRREDEDVEAADSAGNCLDSLVFVAGDRQFGPYCGHGF
PGPLNIETKSNALDIIFQTDLTGQKKGWKLRYHGDPMPCPKEDTPNSVWEPAKAKYVFRD
VVQITCLDGFEVVEGRVGATSFYSTCQSNGKWSNSKLKCQPVDCGIPESIENGKVEDPES
TLFGSVIRYTCEEPYYYMENGGGGEYHCAGNGSWVNEVLGPELPKCVPVCGVPREPEEK
QRIIGGSDADIKNFPWQVFFDNPWAGGALINEYWVLTAAHVVEGNREPTMYVGSTSVQTS
RLAKSKMLTPEHVFIHPGWKLLEVPEGRTNFDNDIALVRLKDPVKMGPTVSPICLPGTSS
DYNLMDGDLGLISGWGRTEKRDRAVRLKAARLPVAPLRKCKEVRVEKPTADAEAYVFTPN
MICAGGEKGMDSCKGDSGGAFAVQDPNDKTKFYAAGLVSWGPQCGTYGLYTRVKNYVDWI
MKTMQENSTPRED (SEQ ID NO:9)

Figure 2
Table 2

| Antibody | CDR-1 | CDR-2 | CDR-3 | V region |
|---|---|---|---|---|
| IPN-M34 VL | SEQ ID NO:1<br>SSVSSSYLHWYQ | SEQ ID NO:2<br>STSNLASGYP | SEQ ID NO:3<br>HQYYRLPPIT | SEQ ID NO:7<br>DIVMTQTTAIMSASLGERVTMTCTASSSVSSSYL HWYQQKPGSSPKLWIYSTSNLASGVPARFSGSG SGTFYSLTISSMEAEDDATYYCHQYYRLPPITFG AGTKLELK |
| IPN-M34 VH | SEQ ID NO:4<br>GFTFSNYAMSWV | SEQ ID NO:5<br>ISSGGSHTYY | SEQ ID NO:6<br>ARLFTGYAMDY | SEQ ID NO:8<br>QVKLEESGGALVKPGGSLKLSCAASGFTFSNYA MSWVRQIPEKRLEWVATISSGGSHTYYLDSVK GRFTISRDNARDTLYLQMSSLRSEDTALYYCAR LFTGYAMDYWGQGTSVT |

| Antibody | Isotype | Inactive C1s | | | Active C1s | | |
|---|---|---|---|---|---|---|---|
| | | $K_D$ (M) | $K_{on}$ (1/Ms) | $K_{dis}$ (1/s) | $K_D$ (M) | $K_{on}$ (1/Ms) | $K_{dis}$ (1/s) |
| M81 | IgG1 | 1.23E-09 | 1.65E+05 | 2.72E-04 | 1.09E-09 | 1.68E+05 | 1.84E-04 |
| IPN003 | IgG2a | 1.58E-09 | 3.56E+05 | 5.53E-04 | 2.04E-09 | 3.23E+05 | 6.58E-04 |

Figure 9

Table 4: Characterization of IPN003 binding to inactive and active human C1s

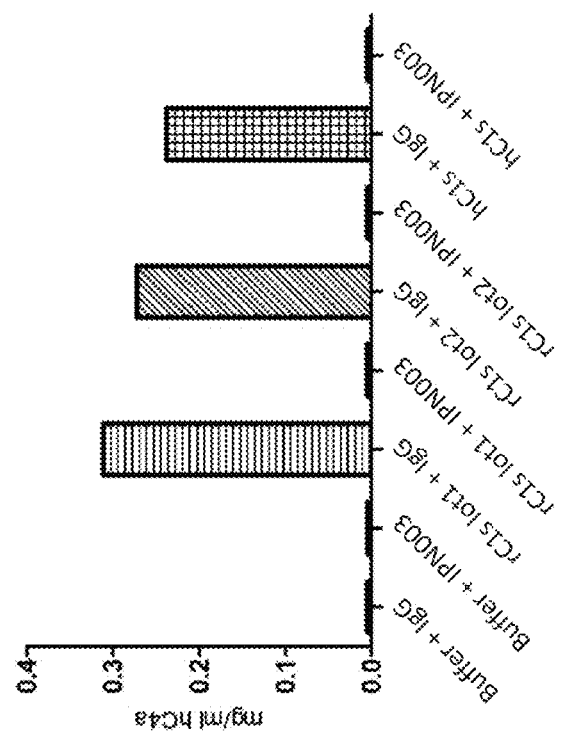

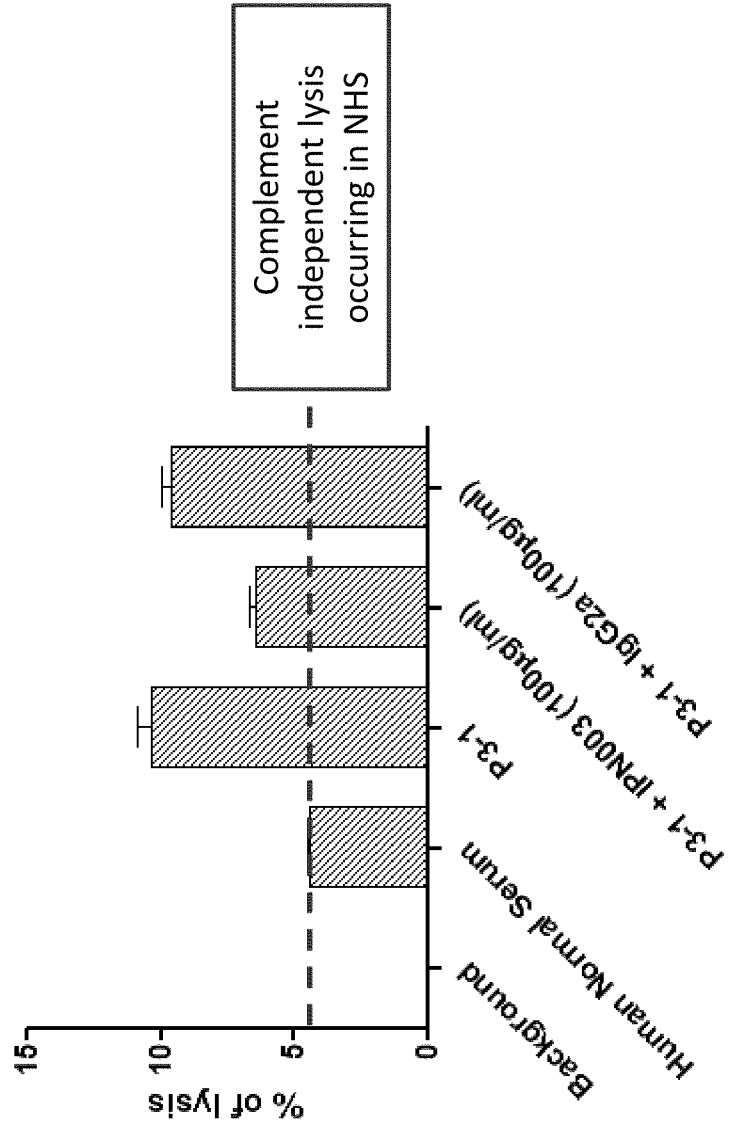
Figure 13. INP003 inhibits AIHA patient (P3-1) mediated hRBC lysis

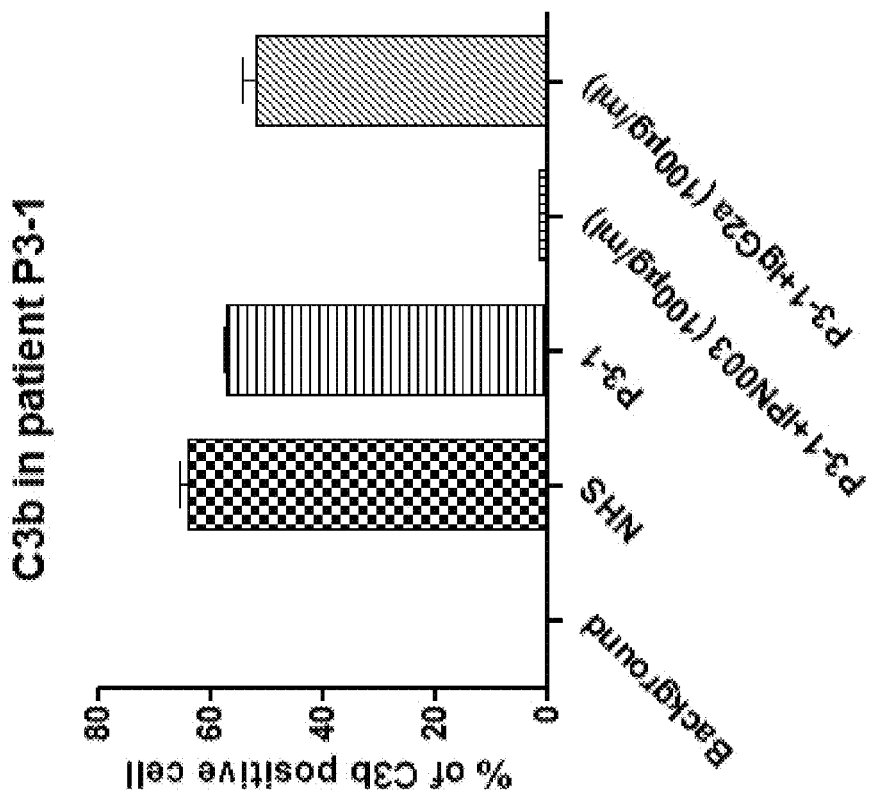
Figure 14. IPN003 inhibits C3b deposition on hRBC incubated in an AIHA serum sample

Figure 15

| Antibody | CDR-1 | CDR-2 | CDR-3 | V region |
|---|---|---|---|---|
| IPN003 VL | SEQ ID NO:32<br>TASSSVSSSYLH | SEQ ID NO:33<br>STSNLAS | SEQ ID NO:3<br>HQYYRLPPIT | SEQ ID NO:37<br>QIVLTQSPAIMSASLGERVTMTCTASSSVSSSYL<br>HWYQQKPGSSPKLWIYSTSNLASGVPARFSGSG<br>SGTFYSLTISSMEAEDDATYYCHQYYRLPPITFG<br>AGTKLELK |
| IPN003 VH | SEQ ID NO:34<br>NYAMS | SEQ ID NO:35<br>TISSGGSHTYYLD<br>SVKG | SEQ ID NO:36<br>LFTGYAMDY | SEQ ID NO:38<br>EVMLVESGGALVKPGGSLKLSCAASGFTFSNYA<br>MSWVRQIPEKRLEWVATISSGGSHTYYLDSVK<br>GRFTISRDNARDTLYLQMSSLRSEDTALYYCAR<br>LFTGYAMDYWGQGTSVTVSS |

CDR definitions according to Kabat numbering system.

Figure 16

VH variant 1

```
         10         20         30         40         50         60         70         80         90        100
GAAGTGATGCTGGTGGAGTCTGGGGGAGGCTTAGTGAAGCCTGGAGGGTCCCTGAGACTCTCCTGTGCAGCCTCTGGATTCACTTTCAGTAATTATGCCA
 E  V  M  L  V  E  S  G  G  G  L  V  K  P  G  G  S  L  R  L  S  C  A  A  S  G  F  T  F  S  N  Y  A
                        10                   20                               30

110        120        130        140        150        160        170        180        190        200
TGTCTTGGGTTCGCCAGGCTCCAGGGAAGGGGCTGGAGTGGGTCGCAACCATTAGTAGTGGTGGTAGTCACTATTATTTAGACAGTGTGAAGGGTCG
 M  S  W  V  R  Q  A  P  G  K  G  L  E  W  V  A  T  I  S  S  G  G  S  H  Y  Y  L  D  S  V  K  G  R
              40                            50 52 A                     60

210        220        230        240        250        260        270        280        290        300
ATTCACCATCTCCAGAGACAATTCCAAGAACACCCTGTACCTGCAAATGAGCAGTCTGAGGGCTGAGGACACGGCCCTGTATTATTGTGCAAGACTGTTT
 F  I  S  R  D  N  S  K  N  T  L  Y  L  Q  M  S  S  L  R  A  E  D  T  A  L  Y  Y  C  A  R  L  F
        70                         80  82 A B C                          90

310        320        330        340        350
ACCGGCTATGCTATGGACTATTGGGGTCAAGGAACCTCAGTCACCGTCTCCTCA       (SEQ ID NO:39)
 T  G  Y  A  M  D  Y  W  G  Q  G  T  S  V  T  V  S  S
       100 A                       110
```

Figure 17

VH variant 2

```
         10        20        30        40        50        60        70        80        90
GAAGTGATGCTGGTGGAGTCTGGGGGAGGCTTAGTGAAGCCTGGAGGGTCCCTGAGACTCTCCTGTGCAGCCTCTGGATTCACTTTCAGTAATTATGCCA
 E  V  M  L  V  E  S  G  G  G  L  V  K  P  G  G  S  L  R  L  S  C  A  A  S  G  F  T  F  S  N  Y  A
                          10                        20                        30

110       120       130       140       150       160       170       180       190       200
TGTCTTGGGTTCGCCAGGCTCCAGGGAAGGGGCTGGAGTGGGTCGCAACCATTAGTAGTGGTGGTAGTCACACCTATTATTTAGACAGTGTGAAGGGTCG
 M  S  W  V  R  Q  A  P  G  K  G  L  E  W  V  A  T  I  S  S  G  G  S  H  T  Y  Y  L  D  S  V  K  G  R
                  40                        50                        60
                                         52 A 210       220       230       240       250       260       270       280       290       300
ATTCACCATCTCCAGAGACAATTCCAAGGACACCCTGTACCTGCAAATGAACAGTCTGAGGGCTGAGGACACGGCCCTGTATTATTGTGCAAGACTGTTT
 F  I  S  R  D  N  S  K  D  T  L  Y  L  Q  M  N  S  L  R  A  E  D  T  A  L  Y  Y  C  A  R  L  F
             70                        80                        90
                                    82 A B C 310       320       330       340       350
ACCGGGCTATGCTATGGACTATTGGGGTCAAGGAACCCTGGTCACCGTCTCCTCA  (SEQ ID NO:40)
 T  G  Y  A  M  D  Y  W  G  Q  G  T  L  V  T  V  S  S
         100                       110
             A
```

Figure 18

VH variant 3

```
         10         20         30         40         50         60         70         80         90        100
GAAGTGATGCTGGTGGAGTCTGGGGGAGGCTTAGTGAAGCCTGGAGGGTCCCTGAGACTCTCCTGTGCAGCCTCTGGATTCACTTTCAGTAATTATGCCA
 E  V  M  L  V  E  S  G  G  G  L  V  K  P  G  G  S  L  R  L  S  C  A  A  S  G  F  T  F  S  N  Y  A
                             10                         20                          30

110        120        130        140        150        160        170        180        190
TGTCTTGGGTTCGCCAGGCTCCAGGGAAGGGGCTGGAGTGGGTCGCAACCATTAGTAGTGGTGGTAGTCACACCTATTATTTAGACAGTGTGAAGGGTCG
 M  S  W  V  R  Q  A  P  G  K  G  L  E  W  V  A  T  I  S  S  G  G  S  H  T  Y  Y  L  D  S  V  K  G  R
                    40                              50                     60
                                                    52 A 210        220        230        240        250        260        270        280        290        300
ATTCACCATCTCCAGAGACAATTCCAAGAACACCCTGTACCTGCAAATGAACAGTCTGAGGGCTGAGGACACGGCCCTGTATTATTGTGCAAGACTGTTT
 F  T  I  S  R  D  N  S  K  N  T  L  Y  L  Q  M  N  S  L  R  A  E  D  T  A  L  Y  Y  C  A  R  L  F
             70                         80                         90
                                         82 A B C 310        320        330        340        350
ACCGGCTATGCTATGGACTATTGGGGTCAAGGAACCCTGGTCACCGTCTCCTCA     (SEQ ID NO:41)
 T  G  Y  A  M  D  Y  W  G  Q  G  T  L  V  T  V  S  S
         100 A                   110
```

Figure 19

VH variant 4

```
         10         20         30         40         50         60         70         80         90        100
GAAGTGCAGCTGGTGGAGTCTGGGGGAGGCTTAGTGAAGCCTGGAGGGTCCCTGAGACTCTCCTGTGCAGCCTCTGGATTCACTTTCAGTAATTATGCCA
 E  V  Q  L  V  E  S  G  G  G  L  V  K  P  G  G  S  L  R  L  S  C  A  A  S  G  F  T  F  S  N  Y  A
                         10                         20                              30

110        120        130        140        150        160        170        180        190        200
TGTCTTGGGTTCGCCAGGCTCCAGGGAAGGGGCTGGAGTGGGTCGCAGTTATTAGTAGTGGTGGTAGTCACACCTATTATTTAGACAGTGTGAAGGGTCG
 M  S  W  V  R  Q  A  P  G  K  G  L  E  W  V  A  V  I  S  S  G  G  S  H  T  Y  Y  L  D  S  V  K  G  R
             40                              50 52 A                            60

210        220        230        240        250        260        270        280        290        300
ATTCACCATCTCCAGAGACAATTCCAAGAACACCCTGTACCTGCAAATGAACAGTCTGAGGGCTGAGGACACGGCCCTGTATTATTGTGCAAGACTGTTT
 F  T  I  S  R  D  N  S  K  N  T  L  Y  L  Q  M  N  S  L  R  A  E  D  T  A  L  Y  Y  C  A  R  L  F
       70                         80  82 A B C                              90

310        320        330        340        350
ACCGGCTATGCTATGGACTATTGGGGTCAAGGAACCCTGGTCACCGTCTCCTCA    (SEQ ID NO:42)
 T  G  Y  A  M  D  Y  W  G  Q  G  T  L  V  T  V  S  S
       100 A                             110
```

Figure 20

VK variant 1

```
         10         20         30         40         50         60         70         80         90        100
CAAATTGTTCTCACCCAGTCTCCAGCAATCCTGTCTCTGTCTCCAGGGGAACGGGCCACCATGTCCTGCACAGCCAGCTCAAGTGTAAGTTCCAGTTACT
 Q  I  V  L  T  Q  S  P  A  I  L  S  L  S  P  G  E  R  A  T  M  S  C  T  A  S  S  V  S  S  S  Y
                                                       10                    20               27 A   30

110        120        130        140        150        160        170        180        190        200
TGCACTGGTACCAGCAGAAGCCAGGAAAGGCCCCCAAACTCTGGATTTATAGCACATCCAACCTGGCTTCTGGAGTCCCATCTCGCTTCAGTGGCAGTGG
 L  H  W  Y  Q  Q  K  P  G  K  A  P  K  L  W  I  Y  S  T  S  N  L  A  S  G  V  P  S  R  F  S  G  S  G
                          40                             50                             60

210        220        230        240        250        260        270        280        290        300
GTCTGGGACCTTTTACACTCTCACAATCAGCAGCCTGCAAGCTGAAGATTTTGCCACTTATTACTGCCACCAGTATTATCGTTTACCACCCATCACGTTC
 S  G  T  F  Y  T  L  T  I  S  S  L  Q  A  E  D  F  A  T  Y  Y  C  H  Q  Y  Y  R  L  P  P  I  T  F
             70                             80                             90               95 A 310        320
GGTCAGGGGACCAAGCTGGAGATCAAA    (SEQ ID NO:43)
 G  Q  G  T  K  L  E  I  K
    100               106 A
```

Figure 21

VK variant 2

```
         10         20         30         40         50         60         70         80         90        100
CAAATTGTTCTCACCCAGTCTCCAGCAACCCTGTCTCTGTCTCCAGGGGAACGGGCCACCATGTCCTGCACAGTCCAGCTCAAGTGTAAGTTCCAGTTACT
 Q  I  V  L  T  Q  S  P  A  T  L  S  L  S  P  G  E  R  A  T  M  S  C  T  A  S  S  V  S  S  S  Y
                            10                          20                         27 A    30
        110        120        130        140        150        160        170        180        190        200
TGCACTGGTACCAGCAGAAGCCAGGAAAGGCCCCCCAAACTCTGGATTTATAGCACATCCAACCTGGCTTCGGAGTCCCATCTCGCTTCAGTGGCAGTGG
 L  H  W  Y  Q  Q  K  P  G  K  A  P  K  L  W  I  Y  S  T  S  N  L  A  S  G  V  P  S  R  F  S  G  S  G
                    40                              50                          60
        210        220        230        240        250        260        270        280        290        300
GTCTGGGACCGATTACACTCTCACAATCAGCAGCCTGCAGCCTGAAGATTTTGCCACTTATTACTGCCACCAGTATTATCGTTTACCACCCATCACGTTC
 S  G  T  D  Y  T  L  T  I  S  S  L  Q  P  E  D  F  A  T  Y  Y  C  H  Q  Y  Y  R  L  P  P  I  T  F
            70                          80                          90                  95 A
        310        320
GGTCAGGGGACCAAGCTGGAGATCAAA     (SEQ ID NO:44)
 G  Q  G  T  K  L  E  I  K
100                   106 A
```

Figure 22

VK variant 3

```
         10         20         30         40         50         60         70         80         90        100
CAAATTGTTCTCACCCAGTCTCCAGCAACCCTGTCTCTGTCTCCAGGGGAACGGGCCACCCTGTCCTGCACAGCCAGTCAAGTGTAAGTTCCAGTTACT
 Q  I  V  L  T  Q  S  P  A  T  L  S  L  S  P  G  E  R  A  T  L  S  C  T  A  S  S  V  S  S  S  Y
                            10                           20                  27 A                 30

110        120        130        140        150        160        170        180        190        200
TGCACTGGTACCAGCAGAAGCCAGGAAAGGCCCCCAAACTCTGGATTTATAGCACATCTAACCTGGCTTCTGGAGTCCCATCTCGCTTCAGTGGCAGTGG
 L  H  W  Y  Q  Q  K  P  G  K  A  P  K  L  W  I  Y  S  T  S  N  L  A  S  G  V  P  S  R  F  S  G  S  G
                   40                                         50                              60

210        220        230        240        250        260        270        280        290        300
GTCTGGGACCGATTACACTCTCACAATCAGCAGCCTGCAGCCTGAAGATTTTGCCACTTATTACTGCCACCAGTATTATCGTTTACCACCCATCACGTTC
 S  G  T  D  Y  T  L  T  I  S  S  L  Q  P  E  D  F  A  T  Y  Y  C  H  Q  Y  Y  R  L  P  P  I  T  F
           70                           80                          90                  95 A 310        320
GGTCAGGGGACCAAGCTGGAGATCAAA    (SEQ ID NO:45)
 G  Q  G  T  K  L  E  I  K
100                106 A
```

Figure 23

Table 7: VH Variants

| Amino Acid Position | IPN003 (Parental antibody) | VH Variant 1 | VH Variant 2 | VH Variant 3 | VH Variant 4 |
|---|---|---|---|---|---|
| 3 | M | M | M | M | Q |
| 10 | A | G | G | G | G |
| 19 | K | R | R | R | R |
| 40 | I | A | A | A | A |
| 42 | E | G | G | G | G |
| 44 | R | G | G | G | G |
| 74 | A | S | S | S | S |
| 75 | R | K | K | K | K |
| 76 | D | D | D | N | N |
| 82A | S | S | N | N | N |
| 84 | S | A | A | A | A |
| 108 | S | S | L | L | L |

Table 8: Vk Variants

| Amino Acid Position | IPN003 (Parental antibody) | Vk Variant 1 | Vk Variant 2 | Vk Variant 3 |
|---|---|---|---|---|
| 10 | I | I | T | T |
| 11 | M | L | L | L |
| 13 | A | L | L | L |
| 15 | L | P | P | P |
| 19 | V | A | A | A |
| 21 | M | M | M | L |
| 22 | T | S | S | S |
| 42 | S | K | K | K |
| 43 | S | A | A | A |
| 60 | A | S | S | S |
| 70 | F | F | D | D |
| 72 | S | T | T | T |
| 78 | M | L | L | L |
| 79 | E | Q | Q | Q |
| 80 | A | A | P | P |
| 83 | D | F | F | F |
| 100 | A | Q | Q | Q |
| 106 | L | I | I | I |

Figure 24

Table 9: Binding of IPN003 variants to activated C1s

| Antibody | $K_D$ (M) | $K_{on}$ (1/Ms) | $K_{dis}$ (1/s) |
|---|---|---|---|
| VH1/Vk1 | 2.348E-10 | 9.734E+05 | 2.285E-04 |
| VH1/Vk2 | 2.616E-10 | 1.049E+06 | 2.744E-04 |
| VH1/Vk3 | 3.758E-10 | 9.137E+05 | 3.433E-04 |
| VH2/Vk1 | 2.555E-10 | 1.073E+06 | 2.742E-04 |
| VH2/Vk2 | 2.728E-10 | 1.026E+06 | 2.798E-04 |
| VH2/Vk3 | 2.965E-10 | 9.477E+05 | 2.810E-04 |
| VH3/Vk1 | 2.461E-10 | 1.034E+06 | 2.544E-04 |
| VH3/Vk2 | 2.742E-10 | 1.133E+06 | 3.108E-04 |
| VH3/Vk3 | 3.351E-10 | 1.075E+06 | 3.601E-04 |
| VH4/Vk1 | 2.284E-10 | 1.187E+06 | 2.711E-04 |
| VH4/Vk2 | 2.624E-10 | 1.005E+06 | 2.638E-04 |
| VH4/Vk3 | 2.981E-10 | 1.041E+06 | 3.103E-04 |

Table 10: Binding of IPN003 variants to pro- C1s

| Antibody | $K_D$ (M) | $K_{on}$ (1/Ms) | $K_{dis}$ (1/s) |
|---|---|---|---|
| VH1/Vk1 | 1.908E-10 | 1.039E+06 | 1.982E-04 |
| VH1/Vk2 | 2.287E-10 | 1.089E+06 | 2.490E-04 |
| VH1/Vk3 | 3.028E-10 | 9.406E+05 | 2.849E-04 |
| VH2/Vk1 | 2.521E-10 | 1.040E+06 | 2.622E-04 |
| VH2/Vk2 | 2.710E-10 | 9.930E+05 | 2.691E-04 |
| VH2/Vk3 | 2.839E-10 | 9.675E+05 | 2.747E-04 |
| VH3/Vk1 | 2.518E-10 | 1.015E+06 | 2.554E-04 |
| VH3/Vk2 | 2.908E-10 | 1.083E+06 | 3.150E-04 |
| VH3/Vk3 | 3.305E-10 | 1.061E+06 | 3.508E-04 |
| VH4/Vk1 | 2.908E-10 | 1.097E+06 | 3.189E-04 |
| VH4/Vk2 | 2.616E-10 | 1.007E+06 | 2.633E-04 |
| VH4/Vk3 | 2.775E-10 | 1.104E+06 | 3.063E-04 |

Figure 25

| V Region IDs | Relative IC$_{50}$ | Yield from 50ml transient culture (µg) |
|---|---|---|
| VH1/Vκ1 | 1.24 | 410.6 |
| VH1/Vκ2 | 1.03 | 11.8 |
| VH1/Vκ3 | 1.21 | 11.7 |
| VH2/Vκ1 | 1.15 | 13.7 |
| VH2/Vκ2 | 1.04 | 18.3 |
| VH2/Vκ3 | 0.81 | 353.0 |
| VH3/Vκ1 | 0.92 | 105.2 |
| VH3/Vκ2 | 1.27 | 11.1 |
| VH3/Vκ3 | 1.05 | 16.7 |
| VH4/Vκ1 | 1.06 | 7.6 |
| VH4/Vκ2 | 0.76 | 329.5 |
| VH4/Vκ3 | 0.97 | 21.5 |
| IPN003 | 0.91 | - |

Figure 28

|  | IC$_{50}$ (hemolysis) | | IC$_{50}$ (C3b depositon) | |
| --- | --- | --- | --- | --- |
|  | (ug/ml) | (nM) | (ug/ml) | (nM) |
| IPN003 | 0.73 | 4.87 | 1.62 | 10.77 |
| VH1/VK1 | 1.07 | 7.13 | 1.61 | 10.74 |
| VH2/VK2 | 0.962 | 6.41 | 3.52 | 23.47 |
| VH2/VK3 | 0.657 | 4.38 | 1.96 | 13.05 |
| VH3/VK1 | 0.578 | 3.85 | 1.05 | 6.97 |
| VH4/VK2 | 0.505 | 3.37 | 0.72 | 4.77 |
| VH4/VK3 | 1.012 | 6.75 | 2.66 | 17.75 |

|  | IC$_{50}$ (hemolysis) | | IC$_{50}$ (C3b depositon) | |
| --- | --- | --- | --- | --- |
|  | (ug/ml) | (nM) | (ug/ml) | (nM) |
| IPN003 | 0.313 | 2.09 | 0.55 | 3.63 |
| VH1/VK1 | 0.611 | 4.07 | 0.90 | 6.00 |
| VH2/VK2 | 0.562 | 3.75 | 0.79 | 5.23 |
| VH2/VK3 | 0.432 | 2.88 | 0.64 | 4.24 |
| VH3/VK1 | 0.437 | 2.91 | 0.62 | 4.14 |
| VH4/VK2 | 0.346 | 2.31 | 0.61 | 4.09 |
| VH4/VK3 | 0.538 | 3.59 | 0.47 | 3.13 |

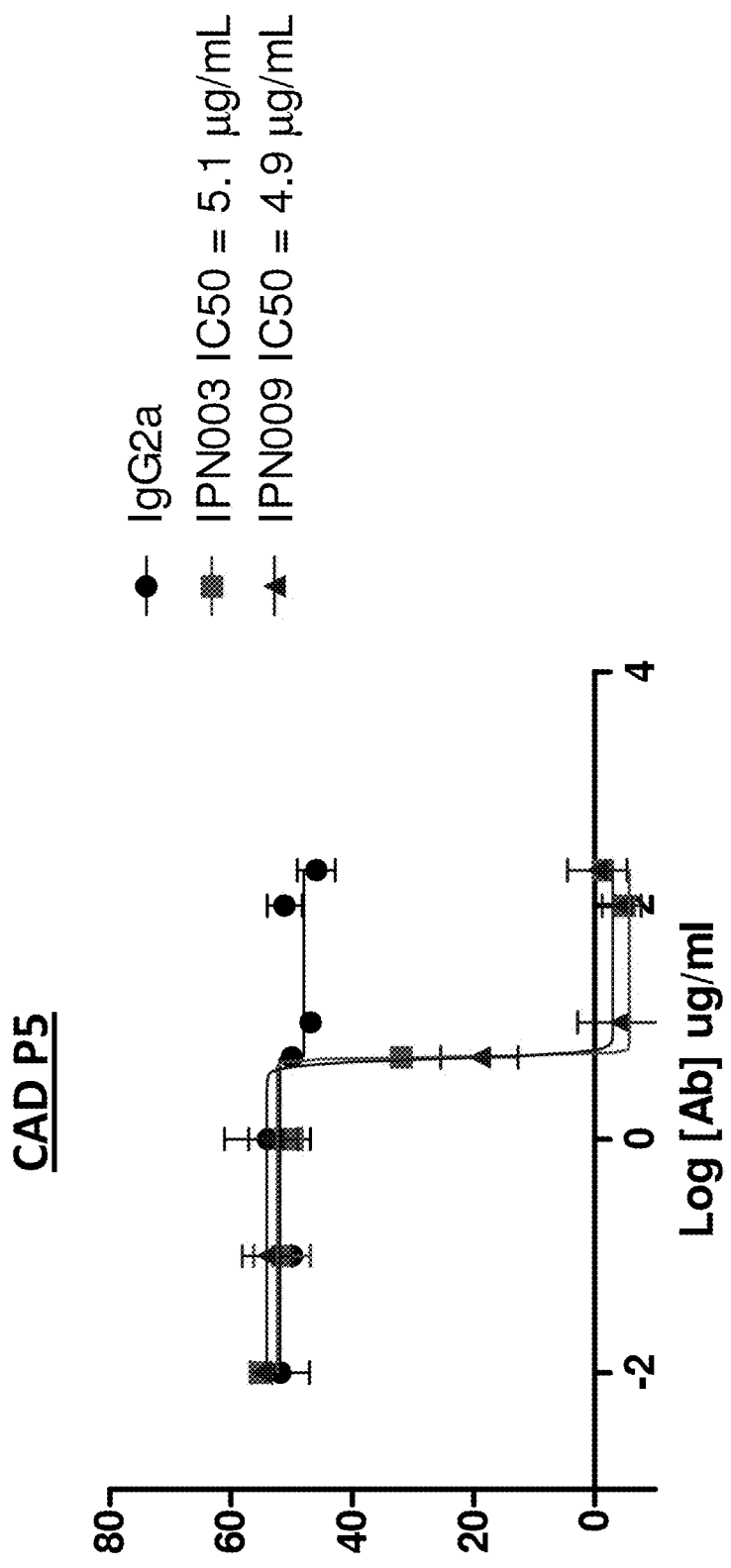
Figure 29. IPN003 and hu-IPN003 Inhibit Complement Dependent Hemolysis in CAD Patient Plasma

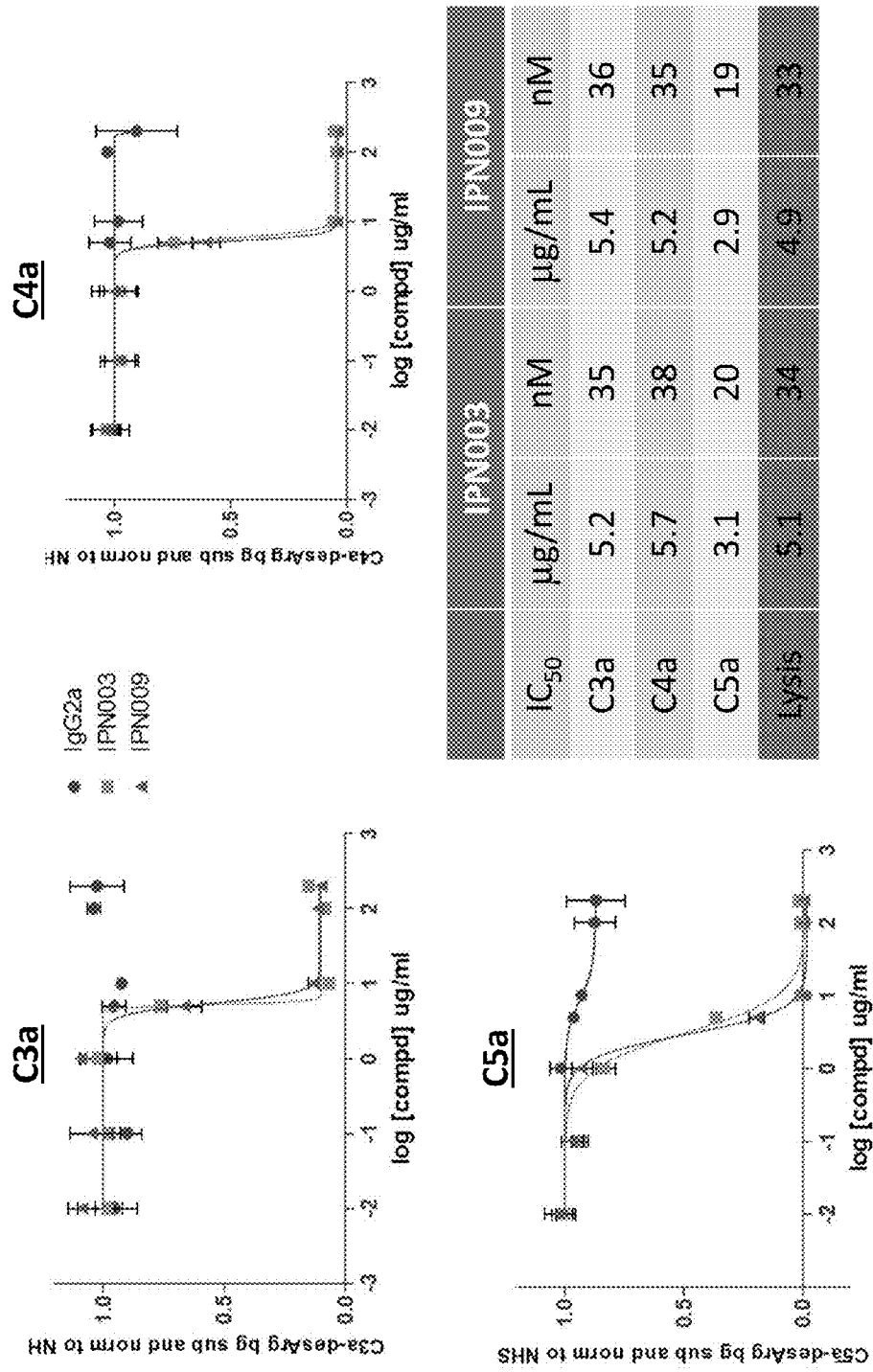
Figure 30. hu-IPN003 and IPN009 Inhibit Anaphylatoxin Production in CAD Plasma Mediated hRBC Hemolysis Assays

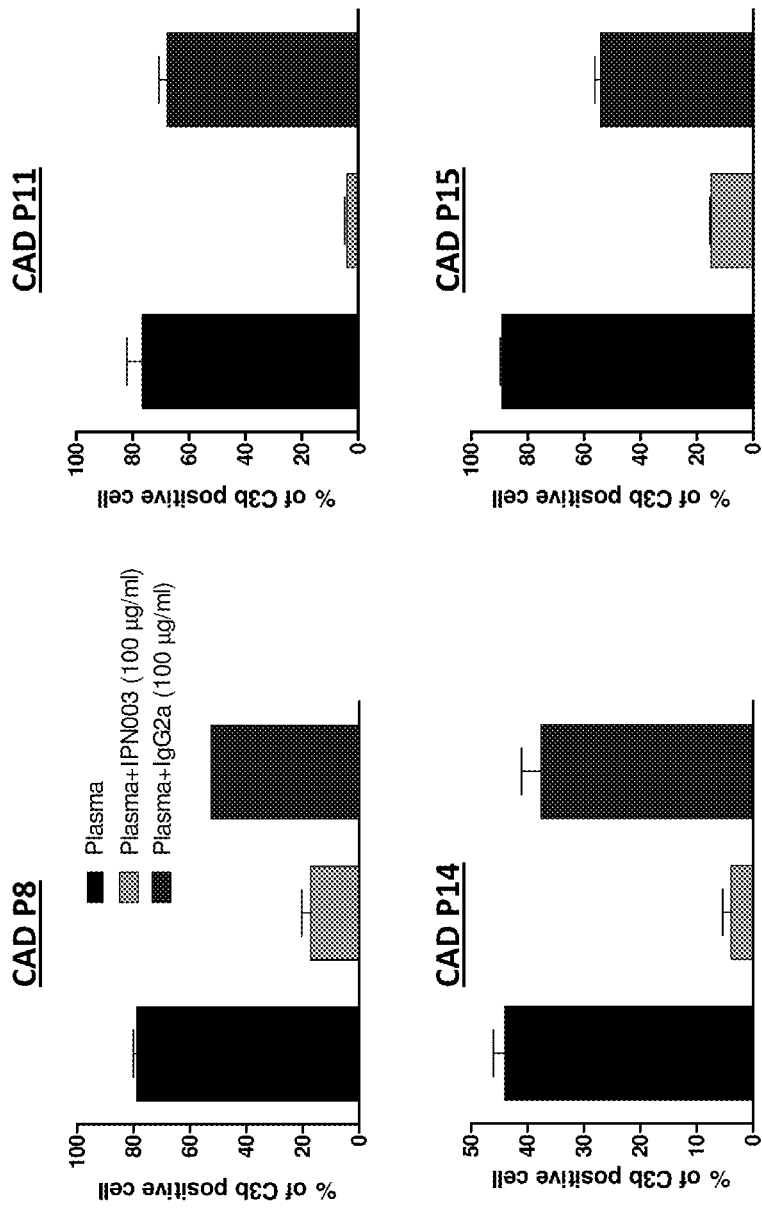
Figure 31. IPN003 Inhibits CAD Patient Plasma Mediated C3b Deposition on hRBC

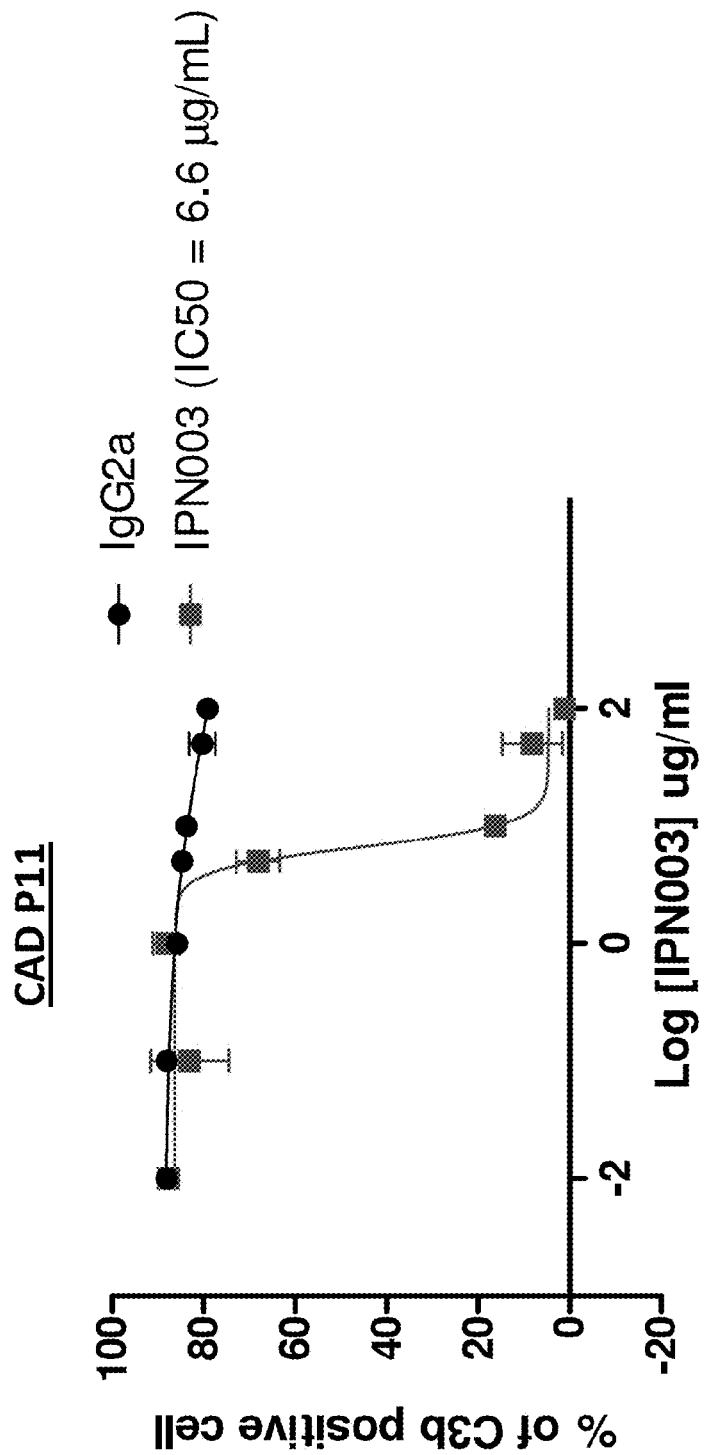
Figure 32. IPN003 Inhibits CAD Plasma Mediated C3b Deposition in a Concentration Dependent Manner (a)

(b)

SEQUENCE LISTING

```
<160> NUMBER OF SEQ ID NOS: 69

<210> SEQ ID NO 1
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 1

Thr Ala Ser Ser Ser Val Ser Ser Ser Tyr Leu His
1               5                   10

<210> SEQ ID NO 2
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 2

Ser Thr Ser Asn Leu Ala Ser
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 3

His Gln Tyr Tyr Arg Leu Pro Pro Ile Thr
1               5                   10

<210> SEQ ID NO 4
<211> LENGTH: 5
<212> TYPE: PRT
<213> ORGANISM: Artificial sequence
```

```
<220> FEATURE:
<223> OTHER INFORMATION: Synthetic amino acid sequence

<400> SEQUENCE: 4

Asn Tyr Ala Met Ser
1               5

<210> SEQ ID NO 5
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 5

Thr Ile Ser Ser Gly Gly Ser His Thr Tyr Tyr Leu Asp Ser Val Lys
1               5                   10                  15

Gly

<210> SEQ ID NO 6
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 6

Leu Phe Thr Gly Tyr Ala Met Asp Tyr
1               5

<210> SEQ ID NO 7
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 7

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Phe Tyr Ser Leu Thr Ile Ser Ser Met Glu
65                  70                  75                  80

Ala Glu Asp Asp Ala Thr Tyr Tyr Cys His Gln Tyr Tyr Arg Leu Pro
                85                  90                  95

Pro Ile Thr Phe Gly Ala Gly Thr Lys Leu Glu Leu Lys
            100                 105

<210> SEQ ID NO 8
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 8

Glu Val Met Leu Val Glu Ser Gly Gly Ala Leu Val Lys Pro Gly Gly
1               5                   10                  15
```

Ser Leu Lys Leu Ser Cys Ala Ala Ser Gly Phe Thr Phe Ser Asn Tyr
            20                  25                  30

Ala Met Ser Trp Val Arg Gln Ile Pro Glu Lys Arg Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ala Arg Asp Thr Leu Tyr
65                  70                  75                  80

Leu Gln Met Ser Ser Leu Arg Ser Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Ser Val Thr Val Ser Ser
            115

<210> SEQ ID NO 9
<211> LENGTH: 673
<212> TYPE: PRT
<213> ORGANISM: Homo sapiens

<400> SEQUENCE: 9

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Val Thr Leu Arg Arg Glu Asp Phe
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr

```
                260                 265                 270
His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Gln Ile
        290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Tyr Met Glu Asn Gly Gly Gly Gly
    370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
        435                 440                 445

Leu Ile Asn Glu Tyr Trp Val Leu Thr Ala Ala His Val Val Glu Gly
    450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525

Thr Val Ser Pro Ile Cys Leu Pro Gly Thr Ser Ser Asp Tyr Asn Leu
    530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp
```

```
<210> SEQ ID NO 10
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 10

Gly Ser Gly Gly Ser
1               5

<210> SEQ ID NO 11
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 11

Gly Gly Gly Ser
1

<210> SEQ ID NO 12
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 12

Gly Gly Ser Gly
1

<210> SEQ ID NO 13
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 13

Gly Gly Ser Gly Gly
1               5

<210> SEQ ID NO 14
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 14

Gly Ser Gly Ser Gly
1               5

<210> SEQ ID NO 15
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 15

Gly Ser Gly Gly Gly
1               5
```

```
<210> SEQ ID NO 16
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 16

Gly Gly Gly Ser Gly
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 17

Gly Ser Ser Ser Gly
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 18

Tyr Pro Tyr Asp Val Pro Asp Tyr Ala
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 19

Asp Tyr Lys Asp Asp Asp Asp Lys
1               5

<210> SEQ ID NO 20
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 20

Glu Gln Lys Leu Ile Ser Glu Glu Asp Leu
1               5                   10

<210> SEQ ID NO 21
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 21

His His His His His
1               5

<210> SEQ ID NO 22
```

```
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 22

His His His His His His
1               5

<210> SEQ ID NO 23
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 23

Trp Ser His Pro Gln Phe Glu Lys
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 24

Arg Tyr Ile Arg Ser
1               5

<210> SEQ ID NO 25
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 25

Phe His His Thr
1

<210> SEQ ID NO 26
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 26

Trp Glu Ala Ala Ala Arg Glu Ala Cys Cys Arg Glu Cys Cys Ala Arg
1               5                   10                  15

Ala

<210> SEQ ID NO 27
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 27

Thr Phe Phe Tyr Gly Gly Cys Arg Gly Lys Arg Asn Asn Phe Lys Thr
1               5                   10                  15

Glu Glu Tyr
```

```
<210> SEQ ID NO 28
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 28

Thr Phe Phe Tyr Gly Gly Ser Arg Gly Lys Arg Asn Asn Phe Lys Thr
1               5                   10                  15

Glu Glu Tyr

<210> SEQ ID NO 29
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 29

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 30
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 30

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 31
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 31

Thr Phe Val Tyr Gly Gly Cys Arg Ala Lys Arg Asn Asn Phe Lys Ser
1               5                   10                  15

<210> SEQ ID NO 32
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 32

Thr Ala Ser Ser Ser Val Ser Ser Ser Tyr Leu His
1               5                   10

<210> SEQ ID NO 33
<211> LENGTH: 7
<212> TYPE: PRT
<213> ORGANISM: Artificial sequence
```

```
<220> FEATURE:
<223> OTHER INFORMATION: Synthetic amino acid sequence

<400> SEQUENCE: 33

Ser Thr Ser Asn Leu Ala Ser
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 34

Asn Tyr Ala Met Ser
1               5

<210> SEQ ID NO 35
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 35

Thr Ile Ser Ser Gly Gly Ser His Thr Tyr Tyr Leu Asp Ser Val Lys
1               5                   10                  15

Gly

<210> SEQ ID NO 36
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 36

Leu Phe Thr Gly Tyr Ala Met Asp Tyr
1               5

<210> SEQ ID NO 37
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 37

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Phe Tyr Ser Leu Thr Ile Ser Ser Met Glu
65                  70                  75                  80

Ala Glu Asp Asp Ala Thr Tyr Tyr Cys His Gln Tyr Tyr Arg Leu Pro
                85                  90                  95

Pro Ile Thr Phe Gly Ala Gly Thr Lys Leu Glu Leu Lys
                100                 105
```

<210> SEQ ID NO 38
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 38

```
Glu Val Met Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Ile Pro Glu Lys Arg Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ala Arg Asp Thr Leu Tyr
65                  70                  75                  80

Leu Gln Met Ser Ser Leu Arg Ser Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Ser Val Thr Val Ser Ser
        115
```

<210> SEQ ID NO 39
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 39

```
Glu Val Met Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ser Lys Asp Thr Leu Tyr
65                  70                  75                  80

Leu Gln Met Ser Ser Leu Arg Ala Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Ser Val Thr Val Ser Ser
        115
```

<210> SEQ ID NO 40
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 40

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Leu Val Thr Val Ser Ser
            115

<210> SEQ ID NO 41
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 41

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ser Lys Asp Thr Leu Tyr
65                  70                  75                  80

Leu Gln Met Ser Ser Leu Arg Ala Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Ser Val Thr Val Ser Ser
            115

<210> SEQ ID NO 42
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Leu Val Thr Val Ser Ser
        115

<210> SEQ ID NO 43
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 43

Gln Ile Val Leu Thr Gln Ser Pro Ala Ile Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Phe Tyr Thr Leu Thr Ile Ser Ser Leu Gln
65                  70                  75                  80

Ala Glu Asp Phe Ala Thr Tyr Tyr Cys His Gln Tyr Tyr Arg Leu Pro
                85                  90                  95

Pro Ile Thr Phe Gly Gln Gly Thr Lys Leu Glu Ile Lys
            100                 105

<210> SEQ ID NO 44
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 44

Gln Ile Val Leu Thr Gln Ser Pro Ala Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr Tyr Arg Leu Pro
                85                  90                  95

Pro Ile Thr Phe Gly Gln Gly Thr Lys Leu Glu Ile Lys
            100                 105

<210> SEQ ID NO 45
<211> LENGTH: 109
<212> TYPE: PRT

<213> ORGANISM: Artificial sequence
<220> FEATURE:
<223> OTHER INFORMATION: Synthetic amino acid sequence

<400> SEQUENCE: 45

```
Gln Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Leu His Trp Tyr Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr Arg Leu Pro
            85                  90                  95

Pro Ile Thr Phe Gly Gln Gly Thr Lys Leu Glu Ile Lys
            100                 105
```

<210> SEQ ID NO 46
<211> LENGTH: 354
<212> TYPE: DNA
<213> ORGANISM: Artificial sequence
<220> FEATURE:
<223> OTHER INFORMATION: Synthetic nucleic acid sequence

<400> SEQUENCE: 46

```
gaagtgatgc tggtggagtc tgggggaggc ttagtgaagc ctggagggtc cctgagactc    60
tcctgtgcag cctctggatt cactttcagt aattatgcca tgtcttgggt tcgccaggct   120
ccagggaagg ggctggagtg ggtcgcaacc attagtagtg gtggtagtca cacctattat   180
ttagacagtg tgaagggtcg attcaccatc tccagagaca attccaagga caccctgtac   240
ctgcaaatga gcagtctgag ggctgaggac acggccctgt attattgtgc aagactgttt   300
accggctatg ctatggacta ttggggtcaa ggaacctcag tcaccgtctc ctca         354
```

<210> SEQ ID NO 47
<211> LENGTH: 354
<212> TYPE: DNA
<213> ORGANISM: Artificial sequence
<220> FEATURE:
<223> OTHER INFORMATION: Synthetic nucleic acid sequence

<400> SEQUENCE: 47

```
gaagtgatgc tggtggagtc tgggggaggc ttagtgaagc ctggagggtc cctgagactc    60
tcctgtgcag cctctggatt cactttcagt aattatgcca tgtcttgggt tcgccaggct   120
ccagggaagg ggctggagtg ggtcgcaacc attagtagtg gtggtagtca cacctattat   180
ttagacagtg tgaagggtcg attcaccatc tccagagaca attccaagga caccctgtac   240
ctgcaaatga acagtctgag ggctgaggac acggccctgt attattgtgc aagactgttt   300
accggctatg ctatggacta ttggggtcaa ggaaccctgg tcaccgtctc ctca         354
```

<210> SEQ ID NO 48
<211> LENGTH: 354
<212> TYPE: DNA
<213> ORGANISM: Artificial sequence
<220> FEATURE:
<223> OTHER INFORMATION: Synthetic nucleic acid sequence

<400> SEQUENCE: 48

```
gaagtgatgc tggtggagtc tgggggaggc ttagtgaagc ctggagggtc cctgagactc    60
tcctgtgcag cctctggatt cactttcagt aattatgcca tgtcttgggt tcgccaggct   120
ccagggaagg ggctggagtg ggtcgcaacc attagtagtg gtggtagtca cacctattat   180
ttagacagtg tgaagggtcg attcaccatc tccagagaca attccaagga caccctgtac   240
ctgcaaatga gcagtctgag ggctgaggac acggccctgt attattgtgc aagactgttt   300
accggctatg ctatggacta ttggggtcaa ggaacctcag tcaccgtctc ctca         354
```

<210> SEQ ID NO 49
<211> LENGTH: 354
<212> TYPE: DNA
<213> ORGANISM: Artificial sequence
<220> FEATURE:
<223> OTHER INFORMATION: Synthetic nucleic acid sequence

<400> SEQUENCE: 49

```
gaagtgcagc tggtggagtc tgggggaggc ttagtgaagc ctggagggtc cctgagactc    60
tcctgtgcag cctctggatt cactttcagt aattatgcca tgtcttgggt tcgccaggct   120
ccagggaagg ggctggagtg ggtcgcaacc attagtagtg gtggtagtca cacctattat   180
ttagacagtg tgaagggtcg attcaccatc tccagagaca attccaagaa caccctgtac   240
ctgcaaatga acagtctgag ggctgaggac acggccctgt attattgtgc aagactgttt   300
accggctatg ctatggacta ttggggtcaa ggaaccctgg tcaccgtctc ctca         354
```

<210> SEQ ID NO 50
<211> LENGTH: 327
<212> TYPE: DNA
<213> ORGANISM: Artificial sequence
<220> FEATURE:
<223> OTHER INFORMATION: Synthetic nucleic acid sequence

<400> SEQUENCE: 50

```
caaattgttc tcacccagtc tccagcaatc ctgtctctgt ctccagggga acgggccacc    60
atgtcctgca cagccagctc aagtgtaagt tccagttact tgcactggta ccagcagaag   120
ccaggaaagg cccccaaact ctggatttat agcacatcca acctggcttc tggagtccca   180
tctcgcttca gtggcagtgg gtctgggacc ttttacactc tcacaatcag cagcctgcag   240
gctgaagatt ttgccactta ttactgccac cagtattatc gtttaccacc catcacgttc   300
ggtcagggga ccaagctgga gatcaaa                                       327
```

<210> SEQ ID NO 51
<211> LENGTH: 327
<212> TYPE: DNA
<213> ORGANISM: Artificial sequence
<220> FEATURE:
<223> OTHER INFORMATION: Synthetic nucleic acid sequence

<400> SEQUENCE: 51

```
caaattgttc tcacccagtc tccagcaacc ctgtctctgt ctccagggga acgggccacc    60
atgtcctgca cagccagctc aagtgtaagt tccagttact tgcactggta ccagcagaag   120
ccaggaaagg cccccaaact ctggatttat agcacatcca acctggcttc tggagtccca   180
tctcgcttca gtggcagtgg gtctgggacc gattacactc tcacaatcag cagcctgcag   240
cctgaagatt ttgccactta ttactgccac cagtattatc gtttaccacc catcacgttc   300
ggtcagggga ccaagctgga gatcaaa                                       327
```

<210> SEQ ID NO 52
<211> LENGTH: 327
<212> TYPE: DNA
<213> ORGANISM: Artificial sequence
<220> FEATURE:
<223> OTHER INFORMATION: Synthetic nucleic acid sequence

<400> SEQUENCE: 52

```
caaattgttc tcacccagtc tccagcaacc ctgtctctgt ctccagggga acgggccacc    60
ctgtcctgca cagccagctc aagtgtaagt tccagttact tgcactggta ccagcagaag   120
ccaggaaagg cccccaaact ctggatttat agcacatcca acctggcttc tggagtccca   180
tctcgcttca gtggcagtgg gtctgggacc gattacactc tcacaatcag cagcctgcag   240
cctgaagatt ttgccactta ttactgccac cagtattatc gtttaccacc catcacgttc   300
ggtcagggga ccaagctgga gatcaaa                                       327
```

<210> SEQ ID NO 53
<211> LENGTH: 25
<212> TYPE: PRT
<213> ORGANISM: Artificial sequence
<220> FEATURE:
<223> OTHER INFORMATION: Synthetic peptide

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 54
<211> LENGTH: 13
<212> TYPE: PRT
<213> ORGANISM: Artificial sequence
<220> FEATURE:
<223> OTHER INFORMATION: Synthetic peptide

<400> SEQUENCE: 54

```
Trp Val Arg Gln Ala Pro Gly Lys Gly Leu Glu Trp Val
1               5                   10
```

<210> SEQ ID NO 55
<211> LENGTH: 30
<212> TYPE: PRT
<213> ORGANISM: Artificial sequence
<220> FEATURE:
<223> OTHER INFORMATION: Synthetic peptide

<400> SEQUENCE: 55

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30
```

<210> SEQ ID NO 56
<211> LENGTH: 11
<212> TYPE: PRT
<213> ORGANISM: Artificial sequence
<220> FEATURE:
<223> OTHER INFORMATION: Synthetic peptide

<400> SEQUENCE: 56

```
Trp Gly Gln Gly Thr Leu Val Thr Val Ser Ser
```

<210> SEQ ID NO 57
<211> LENGTH: 30
<212> TYPE: PRT
<213> ORGANISM: Artificial sequence
<220> FEATURE:
<223> OTHER INFORMATION: Synthetic peptide

<400> SEQUENCE: 57

Arg Phe Thr Ile Ser Ala Asp Thr Ser Lys Asn Thr Ala Tyr Leu Gln
1               5                   10                  15
Met Asn Ser Leu Arg Ala Glu Asp Thr Ala Val Tyr Tyr Cys
            20                  25                  30

<210> SEQ ID NO 58
<211> LENGTH: 25
<212> TYPE: PRT
<213> ORGANISM: Artificial sequence
<220> FEATURE:
<223> OTHER INFORMATION: Synthetic peptide

<400> SEQUENCE: 58

Gln Val Gln Leu Val Gln Ser Gly Ala Glu Val Lys Lys Pro Gly Ala
1               5                   10                  15
Ser Val Lys Val Ser Cys Lys Ala Ser
            20                  25

<210> SEQ ID NO 59
<211> LENGTH: 13
<212> TYPE: PRT
<213> ORGANISM: Artificial sequence
<220> FEATURE:
<223> OTHER INFORMATION: Synthetic peptide

<400> SEQUENCE: 59

Trp Val Arg Gln Ala Pro Gly Gln Gly Leu Glu Trp Met
1               5                   10

<210> SEQ ID NO 60
<211> LENGTH: 30
<212> TYPE: PRT
<213> ORGANISM: Artificial sequence
<220> FEATURE:
<223> OTHER INFORMATION: Synthetic peptide

<400> SEQUENCE: 60

Arg Val Thr Ile Thr Ala Asp Thr Ser Thr Ser Thr Ala Tyr Met Glu
1               5                   10                  15
Leu Ser Ser Leu Arg Ser Glu Asp Thr Ala Val Tyr Tyr Cys
            20                  25                  30

<210> SEQ ID NO 61
<211> LENGTH: 25
<212> TYPE: PRT
<213> ORGANISM: Artificial sequence
<220> FEATURE:
<223> OTHER INFORMATION: Synthetic peptide

<400> SEQUENCE: 61

Gln Val Gln Leu Gln Glu Ser Gly Pro Gly Leu Val Lys Pro Ser Gln
1               5                   10                  15
Thr Leu Ser Leu Thr Cys Thr Val Ser
            20                  25

<210> SEQ ID NO 62
<211> LENGTH: 13
<212> TYPE: PRT
<213> ORGANISM: Artificial sequence
<220> FEATURE:
<223> OTHER INFORMATION: Synthetic peptide

<400> SEQUENCE: 62

Trp Ile Arg Gln Pro Pro Gly Lys Gly Leu Glu Trp Ile
1               5                   10

<210> SEQ ID NO 63
<211> LENGTH: 30
<212> TYPE: PRT
<213> ORGANISM: Artificial sequence
<220> FEATURE:
<223> OTHER INFORMATION: Synthetic peptide

<400> SEQUENCE: 63

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 64
<211> LENGTH: 23
<212> TYPE: PRT
<213> ORGANISM: Artificial sequence
<220> FEATURE:
<223> OTHER INFORMATION: Synthetic peptide

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 65
<211> LENGTH: 15
<212> TYPE: PRT
<213> ORGANISM: Artificial sequence
<220> FEATURE:
<223> OTHER INFORMATION: Synthetic peptide

<400> SEQUENCE: 65

Trp Tyr Leu Gln Lys Pro Gly Gln Ser Pro Gln Leu Leu Ile Tyr
1               5                   10                  15

<210> SEQ ID NO 66
<211> LENGTH: 32
<212> TYPE: PRT
<213> ORGANISM: Artificial sequence
<220> FEATURE:
<223> OTHER INFORMATION: Synthetic peptide

<400> SEQUENCE: 66

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 67
<211> LENGTH: 23
<212> TYPE: PRT
<213> ORGANISM: Artificial sequence

```
<220> FEATURE:
<223> OTHER INFORMATION: Synthetic peptide

<400> SEQUENCE: 67

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 68
<211> LENGTH: 15
<212> TYPE: PRT
<213> ORGANISM: Artificial sequence
<220> FEATURE:
<223> OTHER INFORMATION: Synthetic peptide

<400> SEQUENCE: 68

Trp Tyr Gln Gln Lys Pro Gly Gln Pro Pro Lys Leu Leu Ile Tyr
1               5                   10                  15

<210> SEQ ID NO 69
<211> LENGTH: 32
<212> TYPE: PRT
<213> ORGANISM: Artificial sequence
<220> FEATURE:
<223> OTHER INFORMATION: Synthetic peptide

<400> SEQUENCE: 69

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Phe Ala Val Tyr Tyr Cys
            20                  25                  30
```

US 8,945,562 B2

ANTI-COMPLEMENT C1S ANTIBODIES

CROSS-REFERENCE

This application claims the benefit of U.S. Provisional Patent Application Nos. 61/721,916, filed Nov. 2, 2012, 61/754,123, filed Jan. 18, 2013, 61/779,180, filed Mar. 13, 2013, and 61/846,402, filed Jul. 15, 2013, which applications are incorporated herein by reference in their entirety.

INTRODUCTION

The complement system is a well-known effector mechanism of the immune response, providing not only protection against pathogens and other harmful agents but also recovery from injury. The complement pathway comprises a number of proteins that typically exist in the body in inactive form. The classical complement pathway is triggered by activation of the first component of complement, referred to as the C1 complex, which consists of C1q, C1r, and C1s proteins. Upon binding of C1 to an immune complex or other activator, the C1s component, a diisopropyl fluorophosphate (DFP)-sensitive serine protease, cleaves complement components C4 and C2 to initiate activation of the classical complement pathway. The classical complement pathway appears to play a role in many diseases and disorders.

There is a need in the art for compounds that treat a complement-mediated disease or disorder. There is also a need for compounds that can detect or monitor such disease or disorder. Also needed are methods to produce and use such compounds and compositions thereof.

SUMMARY

The present disclosure provides antibodies that bind complement C1s protein; and nucleic acid molecules that encode such antibodies. The present disclosure also provides compositions comprising such antibodies, and methods to produce and use such antibodies, nucleic acid molecules, and compositions.

The present disclosure provides an isolated humanized monoclonal antibody that inhibits cleavage of complement component C4, where the antibody does not inhibit cleavage of complement component C2. In some cases, the antibody inhibits a component of the classical complement pathway; in some cases, the classical complement pathway component is C1s. In some instances, the antibody does not inhibit protease activity of C1s.

The present disclosure provides an isolated humanized monoclonal antibody that specifically binds an epitope within a region encompassing domains IV and V of complement component is (C1s). In some cases, the antibody inhibits binding of C1s to complement component 4 (C4). In some cases, the antibody does not inhibit protease activity of C1s. In some cases, the epitope bound by an isolated humanized monoclonal antibody of the present disclosure is a conformational epitope.

The present disclosure provides an isolated humanized monoclonal antibody that binds complement component C1s in a C1 complex with high avidity.

The present disclosure provides an isolated humanized monoclonal antibody that is specific for complement component C1s and that inhibits complement-mediated cell lysis with an IC50 of less than $10 \times 10^{-9}$ M and/or inhibits C4 activation with an IC50 of less than $50 \times 10^{-9}$ M.

In any of the embodiments of the present disclosure, the antibody can comprise one or more of the complementarity determining regions (CDRs) of an antibody light chain variable region comprising amino acid sequence SEQ ID NO:7 or one or more of the CDRs of an antibody heavy chain variable region comprising amino acid sequence SEQ ID NO:8.

In any of the embodiments of the present disclosure, the antibody can comprise: a) a complementarity determining region (CDR) having an amino acid sequence selected from the group consisting of SEQ ID NO:1, SEQ ID NO:2, SEQ ID NO:3, SEQ ID NO:4, SEQ ID NO:5, and SEQ ID NO:6; or b) a CDR having an amino acid sequence selected from the group consisting of SEQ ID NO:32, SEQ ID NO:33, SEQ ID NO:3, SEQ ID NO:34, SEQ ID NO:35: and SEQ ID NO:36.

In any of the embodiments of the present disclosure, the antibody can comprise: a) light chain CDRs of an antibody light chain variable region comprising amino acid sequence SEQ ID NO:7 or heavy chain CDRs of an antibody heavy chain variable region comprising amino acid sequence SEQ ID NO:8; or b) light chain CDRs of an antibody light chain variable region comprising amino acid sequence SEQ ID NO:37 or heavy chain CDRs of an antibody heavy chain variable region comprising amino acid sequence SEQ ID NO:38.

In any of the embodiments of the present disclosure, the antibody can comprise: a) light chain CDRs of an antibody light chain variable region comprising amino acid sequence SEQ ID NO:7 and heavy chain CDRs of an antibody heavy chain variable region comprising amino acid sequence SEQ ID NO:8; or b) light chain CDRs of an antibody light chain variable region comprising amino acid sequence SEQ ID NO:37 and heavy chain CDRs of an antibody heavy chain variable region comprising amino acid sequence SEQ ID NO:38.

In any of the embodiments of the present disclosure, the antibody can comprise heavy and light chain complementarity-determining regions (CDRs) having an amino acid sequence selected from: a) SEQ ID NO:1, SEQ ID NO:2, SEQ ID NO:3, SEQ ID NO:4, SEQ ID NO:5, and SEQ ID NO:6; and b) a CDR having an amino acid sequence selected from the group consisting of SEQ ID NO:32, SEQ ID NO:33, SEQ ID NO:3, SEQ ID NO:34, SEQ ID NO:35: and SEQ ID NO:36.

The present disclosure provides a humanized antibody that specifically binds complement component 1s (C1s), wherein the antibody competes for binding the epitope with an antibody that comprises one or more of the CDRs of an antibody light chain variable region comprising amino acid sequence SEQ ID NO:7 or one or more of the CDRs of an antibody heavy chain variable region comprising amino acid sequence SEQ ID NO:8.

The present disclosure provides a humanized antibody that specifically binds complement component 1s (C1s), wherein the antibody is selected from the group consisting of: a) a humanized antibody that specifically binds an epitope within the complement C1s protein, wherein the antibody competes for binding the epitope with an antibody that comprises a CDR having an amino acid sequence selected from the group consisting of SEQ ID NO:1, SEQ ID NO:2, SEQ ID NO:3, SEQ ID NO:4, SEQ ID NO:5, and SEQ ID NO:6; and b) a humanized antibody that specifically binds an epitope within the complement C1s protein, wherein the antibody competes for binding the epitope with an antibody that comprises a CDR having an amino acid sequence selected from the group consisting of SEQ ID NO:32, SEQ ID NO:33, SEQ ID NO:3, SEQ ID NO:34, SEQ ID NO:35, and SEQ ID NO:36.

The present disclosure provides a humanized antibody that binds a complement C1s protein, wherein the antibody specifically binds an epitope within the complement C1s protein, wherein the antibody competes for binding the epitope with an antibody that comprises: a) light chain CDRs of an antibody light chain variable region comprising amino acid sequence SEQ ID NO:7 or SEQ ID NO:37; or b) heavy chain CDRs of an antibody heavy chain variable region comprising amino acid sequence SEQ ID NO:8 or SEQ ID NO:38.

The present disclosure provides a humanized antibody that binds a complement C1s protein, wherein the antibody specifically binds an epitope within the complement C1s protein, wherein the antibody competes for binding the epitope with an antibody that comprises: a) light chain CDRs of an antibody light chain variable region comprising amino acid sequence SEQ ID NO:7 or SEQ ID NO:37; and b) heavy chain CDRs of an antibody heavy chain variable region comprising amino acid sequence SEQ ID NO:8 or SEQ ID NO:38. In some cases, the antibody competes for binding the epitope with an antibody that comprises heavy and light chain CDRs comprising: a) SEQ ID NO:1, SEQ ID NO:2, SEQ ID NO:3, SEQ ID NO:142, SEQ ID NO:5, and SEQ ID NO:6; or b) SEQ ID NO:32, SEQ ID NO:33, SEQ ID NO:3, SEQ ID NO:34, SEQ ID NO:35, and SEQ ID NO:36.

In any of the embodiments of the present disclosure, the antibody can bind a human complement C1s protein. In any of the embodiments of the present disclosure, the antibody can bind a rat complement C1s protein. In any of the embodiments of the present disclosure, the antibody can bind a monkey complement C1s protein. In any of the embodiments of the present disclosure, the antibody can bind a human complement C1s protein, a rat complement C1s protein, and a monkey complement C1s protein. In any of the embodiments of the present disclosure, the antibody can comprise a humanized light chain framework region. For example, the humanized light chain framework region can comprise 1, 2, 3, 4, 5, 6, 7, 8, 9, 10, 11, 12, 13, 14, 15, 16, 17, or 18 of the amino acid substitutions depicted in Table 8. In any of the embodiments of the present disclosure, the antibody can comprise a humanized heavy chain framework region. For example, the humanized heavy chain framework region can comprise 1, 2, 3, 4, 5, 6, 7, 8, 9, 10, 11, or 12 of the amino acid substitutions depicted in Table 7. In any of the embodiments of the present disclosure, the antibody can be an antigen binding fragment that binds complement C1s protein. In any of the embodiments of the present disclosure, the antibody is selected from the group consisting of an Ig monomer, a Fab fragment, a F(ab')₂ fragment, a Fd fragment, a scFv, a scAb, a dAb, a Fv, a single domain heavy chain antibody, and a single domain light chain antibody. In any of the embodiments of the present disclosure, the antibody is selected from the group consisting of a mono-specific antibody, a bi-specific antibody, and a multi-specific antibody. In any of the embodiments of the present disclosure, the antibody can comprise a light chain region and a heavy chain region that are present in separate polypeptides. In any of the embodiments of the present disclosure, the antibody can comprise a light chain region and a heavy chain region that are present in a single polypeptide. In any of the embodiments of the present disclosure, the antibody can comprise an Fc region. In any of the embodiments of the present disclosure, the light chain and heavy chain CDRs are selected from the group consisting of: a) SEQ ID NO:1, SEQ ID NO:2, SEQ ID NO:3, SEQ ID NO:4, SEQ ID NO:5, and SEQ ID NO:6; and b) SEQ ID NO:32, SEQ ID NO:33, SEQ ID NO:3, SEQ ID NO:34, SEQ ID NO:35, and SEQ ID NO:36.

The present disclosure provides an antibody that binds a complement C1s protein, where the antibody comprises a complementarity-determining region (CDR) having an amino acid sequence selected from the group consisting of SEQ ID NO:1, SEQ ID NO:2, SEQ ID NO:3, SEQ ID NO:4, SEQ ID NO:5, and SEQ ID NO:6. In some embodiments, the antibody comprises a light chain variable region comprising amino acid sequences SEQ ID NO:1, SEQ ID NO:2, and SEQ ID NO:3. In some embodiments, the antibody comprises a heavy chain variable region comprising amino acid sequences SEQ ID NO:4, SEQ ID NO:5, and SEQ ID NO:6. In some embodiments, the antibody comprises a CDR-L1 having amino acid sequence SEQ ID NO:1, a CDR-L2 having amino acid sequence SEQ ID NO:2, a CDR-L3 having amino acid sequence SEQ ID NO:3, a CDR-H1 having amino acid sequence SEQ ID NO:4, a CDR-H2 having amino acid sequence SEQ ID NO:5, and a CDR-H3 having amino acid sequence SEQ ID NO:6.

In some embodiments, an anti-C1s antibody of the present disclosure comprises a light chain variable region comprising an amino acid sequence that is 90% identical to amino acid sequence SEQ ID NO:7. In some embodiments, an anti-C1s antibody of the present disclosure comprises a heavy chain variable region comprising an amino acid sequence that is 90% identical to amino acid sequence SEQ ID NO:8. In some embodiments, an anti-C1s antibody of the present disclosure comprises a light chain variable region comprising amino acid sequence SEQ ID NO:7. In some embodiments, an anti-C1s antibody of the present disclosure comprises a heavy chain variable region comprising amino acid sequence SEQ ID NO:8. In some embodiments, an anti-C1s antibody of the present disclosure comprises a light chain variable region comprising an amino acid sequence that is 90% identical to amino acid sequence SEQ ID NO:7 and a heavy chain variable region comprising an amino acid sequence that is 90% identical to amino acid sequence SEQ ID NO:8. In some embodiments, an anti-C1s antibody of the present disclosure comprises a light chain variable region comprising amino acid sequence SEQ ID NO:7 and a heavy chain variable region comprising amino acid sequence SEQ ID NO:8.

The present disclosure provides an antibody that binds a complement C1s protein, wherein the antibody specifically binds an epitope within the complement C1s protein, wherein the antibody competes for binding the epitope with an antibody that comprises light chain CDRs of an antibody light chain variable region comprising amino acid sequence SEQ ID NO:7 and heavy chain CDRs of an antibody heavy chain variable region comprising amino acid sequence SEQ ID NO:8. In some embodiments, an anti-C1s antibody of the present disclosure comprises light chain CDRs of an antibody light chain variable region comprising amino acid sequence SEQ ID NO:7 and heavy chain CDRs of an antibody heavy chain variable region comprising amino acid sequence SEQ ID NO:8.

In any of the above-noted embodiments, an anti-C1s antibody of the present disclosure binds a human complement C1s protein. In some embodiments, an anti-C1s antibody of the present disclosure binds a rat complement C1s protein. In some embodiments, an anti-C1s antibody of the present disclosure inhibits cleavage of at least one substrate cleaved by complement C1s protein. In some embodiments, the substrate is selected from the group consisting of complement C2 and complement C4.

In any of the above-noted embodiments, an anti-C1s antibody of the present disclosure can comprise a humanized light chain framework region. In any of the above-noted embodiments, an anti-C1s antibody of the present disclosure can comprise a humanized heavy chain framework region.

In any of the above-noted embodiments, an anti-C1s antibody of the present disclosure can be an Ig monomer or an antigen-binding fragment thereof that binds complement C1s protein. In any of the above-noted embodiments, an anti-C1s antibody of the present disclosure can be an antigen-binding fragment that binds complement C1s protein. In any of the above-noted embodiments, an anti-C1s antibody of the present disclosure is selected from the group consisting of an Ig monomer, a Fab fragment, a F(ab')$_2$ fragment, a Fd fragment, a scFv, a scAb, a dAb, a Fv, a single domain heavy chain antibody, and a single domain light chain antibody. In any of the above-noted embodiments, an anti-C1s antibody of the present disclosure is selected from the group consisting of a mono-specific antibody, a bi-specific antibody, and a multi-specific antibody.

In some embodiments, an anti-C1s antibody of the present disclosure comprises a light chain region and a heavy chain region that are present in separate polypeptides. In some embodiments, an anti-C1s antibody of the present disclosure comprises a light chain region and a heavy chain region that are present in a single polypeptide. In some embodiments, an anti-C1s antibody of the present disclosure comprises a Fc region.

The present disclosure provides an antibody that competes for binding the epitope bound by antibody IPN003 (also referred to herein as "IPN-M34" or "M34" or "TNT003"). The present disclosure provides an antibody comprising a variable domain of antibody IPN003. The present disclosure provides antibody IPN003.

The present disclosure provides an anti-C1s antibody produced by a method comprising recombinant production.

The present disclosure provides an antibody that binds a complement C1s protein, wherein the antibody is encapsulated in a liposome.

The present disclosure provides an antibody that binds a complement C1s protein, wherein the antibody comprises a covalently linked non-peptide synthetic polymer. In some embodiments, the synthetic polymer is a poly(ethylene glycol) polymer.

The present disclosure provides an antibody that binds a complement C1s protein, wherein the antibody is formulated with an agent that facilitates crossing the blood-brain barrier.

The present disclosure provides an antibody that binds a complement C1s protein, wherein the antibody is fused, directly or through a linker, to a compound that promotes the crossing of the blood-brain barrier, wherein the compound is selected from the group consisting of a carrier molecule, a peptide, or a protein.

The present disclosure provides a nucleic acid molecule that encodes an anti-C1s antibody of any of the embodiments disclosed herein. In some embodiments, the present disclosure provides a recombinant vector comprising such a nucleic acid molecule. In some embodiments, the present disclosure provides a recombinant molecule comprising such a nucleic acid molecule. In some embodiments, the present disclosure provides a recombinant cell comprising such a recombinant molecule.

The present disclosure provides a pharmaceutical composition comprising an anti-C1s antibody of any of the embodiments disclosed herein and a pharmaceutically acceptable excipient. Some embodiments include a sterile container comprising such a pharmaceutical composition. In some embodiments, the container is selected from the group consisting of a bottle and a syringe.

The present disclosure provides a method to treat an individual having a complement-mediated disease or disorder, the method comprising administering to the individual an anti-C1s antibody of any of the embodiments disclosed herein or a pharmaceutical composition thereof. In some embodiments, the individual is a mammal. In some embodiments, the individual is a human. In some embodiments, the administering is intravenous. In some embodiments, the administering is intrathecal. In some embodiments, the administering results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition; (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) a reduction in demyelination; (ab) a reduction in eosinophilia; (ac) a reduction in C3 deposition on red blood cells (e.g., a reduction of deposition of C3b, iC3b, etc., on RBCs); (ad) a reduction in C3 deposition on platelets (e.g., a reduction of deposition of C3b, iC3b, etc., on platelets); (ae) reduction in anaphylatoxin (e.g., C3a, C4a, C5a) production; (af) a reduction in autoantibody mediated blister formation; (ag) a reduction in autoantibody induced pruritis; (ah) a reduction in autoantibody induced erythematosus; (ai) a reduction in autoantibody mediated skin erosion; (aj) a reduction in red blood cell destruction due to transfusion reactions; (ak) a reduction in red blood cell lysis due to alloantibodies; (al) a reduction in hemolysis due to transfusion reactions; (am) a reduction in allo-antibody mediated platelet lysis; (an) a reduction in platelet lysis due to transfusion reactions; (ao) a reduction in mast cell activation; (ap) a reduction in mast cell histamine release; (aq) a reduction in vascular permeability; (ar) a reduction in edema; (as) a reduction in complement deposition on transplant graft endothelium; (at) a reduction of anaphylatoxin generation in transplant graft endothelium; (au) a reduction in the separation of the dermal-epidermal junction; (av) a reduction in the generation of anaphylatoxins in the dermal-epidermal junction; (aw) a reduction in alloantibody mediated complement activation in transplant graft endothelium; (ax) a reduction in antibody mediated loss of the neuromuscular junction; (ay) a reduction in complement activation at the neuromuscular junction; (az) a reduction in anaphylatoxin generation at the neuromuscular junction; (ba) a reduction in complement deposition at the neuromuscular junction; (bb) a reduction in paralysis; (bc) a reduction in numbness; (bd) increased bladder control; (be) increased bowel control; (bf) a reduction in mortality associated with autoantibodies; and (bg) a reduction in morbidity associated with autoantibodies. In some embodiments, the reduction in glial cell activation comprises reduction in astrocyte activation or reduction in microglia activation.

The present disclosure provides a method to inhibit complement activation in an individual having a complement-mediated disease or disorder, the method comprising administering to the individual an anti-C1s antibody of any of the embodiments disclosed herein or a pharmaceutical composition thereof. In some embodiments, the individual is a mammal. In some embodiments, the individual is a human. In some embodiments, the administering is intravenous. In some embodiments, the administering is intrathecal. In some embodiments, the administering is subcutaneous. In some embodiments, the administering results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition; (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) a reduction in demyelination; (ab) a reduction in eosinophilia; (ac) a reduction in C3 deposition on red blood cells (e.g., a reduction of deposition of C3b, iC3b, etc., on RBCs); (ad) a reduction in C3 deposition on platelets (e.g., a reduction of deposition of C3b, iC3b, etc., on platelets); (ae) reduction in anaphylatoxin production; (af) a reduction in autoantibody mediated blister formation; (ag) a reduction in autoantibody induced pruritis; (ah) a reduction in autoantibody induced erythematosus; (ai) a reduction in autoantibody mediated skin erosion; (aj) a reduction in red blood cell destruction due to transfusion reactions; (ak) a reduction in red blood cell lysis due to alloantibodies; (al) a reduction in hemolysis due to transfusion reactions; (am) a reduction in allo-antibody mediated platelet lysis; (an) a reduction in platelet lysis due to transfusion reactions; (ao) a reduction in mast cell activation; (ap) a reduction in mast cell histamine release; (aq) a reduction in vascular permeability; (ar) a reduction in edema; (as) a reduction in complement deposition on transplant graft endothelium; (at) a reduction of anaphylatoxin generation in transplant graft endothelium; (au) a reduction in the separation of the dermal-epidermal junction; (av) a reduction in the generation of anaphylatoxins in the dermal-epidermal junction; (aw) a reduction in alloantibody mediated complement activation in transplant graft endothelium; (ax) a reduction in antibody mediated loss of the neuromuscular junction; (ay) a reduction in complement activation at the neuromuscular junction; (az) a reduction in anaphylatoxin generation at the neuromuscular junction; (ba) a reduction in complement deposition at the neuromuscular junction; (bb) a reduction in paralysis; (bc) a reduction in numbness; (bd) increased bladder control; (be) increased bowel control; (bf) a reduction in mortality associated with autoantibodies; and (bg) a reduction in morbidity associated with autoantibodies. In some embodiments, the reduction in glial cell activation comprises reduction in astrocyte activation or reduction in microglia activation.

The present disclosure provides use of an anti-C1s antibody of any of the embodiments or a pharmaceutical composition thereof to treat an individual having a complement-mediated disease or disorder.

The present disclosure provides use of an anti-C1s antibody of any of the embodiments in the manufacture of a medicament for the treatment of an individual having a complement-mediated disease or disorder.

The present disclosure provides use of an anti-C1s antibody of any of the embodiments or a pharmaceutical composition thereof for inhibiting complement C1s activity, where "inhibiting complement C1s activity" includes inhibiting complement activation, e.g., inhibiting production of C4b2a (i.e., complement C4b and C2a complex; also known as "C3 convertase"). In some embodiments, the present disclosure provides use of an anti-C1s antibody of any of the embodiments or a pharmaceutical composition thereof for inhibiting complement activation in an individual having a complement-mediated disease or disorder.

The present disclosure provides use of an anti-C1s antibody of any of the embodiments or a pharmaceutical composition thereof in the manufacture of a medicament for inhibiting complement activation. In some embodiments, the present disclosure provides use of an anti-C1s antibody of any of the embodiments or a pharmaceutical composition thereof in the manufacture of a medicament for inhibiting complement activation in an individual having a complement-mediated disease or disorder.

The present disclosure provides an anti-C1s antibody of any of the embodiments or a pharmaceutical composition thereof for use in medical therapy.

The present disclosure provides an anti-C1s antibody of any of the embodiments or a pharmaceutical composition thereof for treating an individual having a complement-mediated disease or disorder.

The present disclosure provides an anti-C1s antibody of any of the embodiments or a pharmaceutical composition thereof for inhibiting complement activation. The present disclosure provides an anti-C1s antibody of any of the embodiments or a pharmaceutical composition thereof for inhibiting complement activation in an individual having a complement-mediated disease or disorder.

The present disclosure provides a method to diagnose a complement-mediated disease or disorder in an individual, the method comprising: (a) determining the amount of a complement C1s protein in a biological sample obtained from the individual, wherein the step of determining comprises: (i) contacting the biological sample with an anti-C1s antibody of any of the embodiments; and (ii) quantitating binding of the antibody to complement C1s protein present in the biological sample; and (b) comparing the amount of the complement C1s protein in the biological sample to a normal control value that indicates the amount of complement C1s protein in a normal control individual, wherein a significant difference between the amount of C1s protein in the biological sample and the normal control value indicates that the individual has a complement-mediated disease or disorder. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample.

The present disclosure provides a method to monitor progression of a complement-mediated disease or disorder in an individual, the method comprising: (a) determining a first amount of a complement C1s protein in a biological sample obtained from the individual at a first time point; (b) determining a second amount of complement a C1s protein in a biological sample obtained from the individual at a second time point; and (c) comparing the second amount of complement C1s protein with the first amount of complement C1s protein. The steps of determining comprise: (i) contacting the biological sample with an anti-C1s antibody of any of the embodiments; and (ii) quantitating binding of the antibody to complement C1s protein present in the biological sample. In some embodiments, the first time point is a time point before initiation of a treatment regimen, and the second time point is a time point after initiation of a treatment regimen. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample.

The present disclosure provides an in vitro method to detect complement C1s protein in a biological sample obtained from an individual, the method comprising: (a) contacting the biological sample with an anti-C1s antibody of any of the embodiments; and (b) detecting binding of the antibody to complement C1s protein present in the biological sample. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample. In some embodiments, the method is quantitative.

The present disclosure provides a method to detect complement C1s protein in a living individual in vivo, the method comprising: (a) administering to the individual an anti-C1s antibody of any of the embodiments; and (b) detecting binding of the antibody to complement C1s protein in the individual using an imaging method. In some embodiments, the binding is detected in the individual at a site altered by a complement-mediated disease or disorder. In some embodiments, the binding is detected in the brain of the individual. In some of the embodiments, the antibody comprises a contrast agent suitable for use in the imaging method. In some embodiments, the imaging method is selected from the group consisting of magnetic resonance imaging, positron emission tomography, and IVIS instrumentation. In some embodiments, the method is quantitative.

In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample.

In some embodiments, the methods of the present disclosure provide that the individual is suspected of having a complement-mediated disease or disorder, has been diagnosed as having a complement-mediated disease or disorder, or has a genetic predisposition to developing a complement-mediated disease or disorder.

The present disclosure provides a composition comprising: (a) an anti-C1s antibody of any of the embodiments; and (b) a solution comprising one or more agents that maintain an organ or a tissue intended for transplantation into a recipient individual. In some embodiments, the solution is an organ preservation solution or a tissue preservation solution. In some embodiments, the solution is an organ perfusion solution or a tissue perfusion solution. In some embodiments, the solution comprises: i) a salt; ii) an agent that reduces edema; iii) an oxygen free-radical scavenger; and iii) an energy supply system component. In some embodiments, the composition comprises potassium lactobionate, $KH_2PO_4$, $MgSO_4$, raffinose, adenosine, glutathione, allopurinol, and hydroxyethyl starch.

The present disclosure provides an organ or tissue preservation solution comprising an anti-C1s antibody of any of the embodiments or a pharmaceutical composition thereof.

The present disclosure provides an organ or tissue perfusion solution comprising an anti-C1s antibody of any of the embodiments or a pharmaceutical composition thereof.

The present disclosure provides a method for maintaining an organ or tissue for transplant, the method comprising contacting the organ or the tissue with a composition comprising: (a) an anti-C1s antibody of any of the embodiments; and (b) an organ or tissue preservation solution of any of the embodiments or an organ or tissue perfusion solution of any of the embodiments.

The present disclosure provides an isolated organ or tissue maintained in a composition comprising: (a) an anti-C1s antibody of any of the embodiments; and (b) an organ or tissue preservation solution of any of the embodiments or an organ or tissue perfusion solution of any of the embodiments. In some embodiments, the organ is selected from the group consisting of an eye, a heart, an intestine, a kidney, a liver, a lung, a pancreas, a stomach, and a thymus. In some embodiments, the tissue is selected from the group consisting of bone, bone marrow, cornea, heart valve, islet of Langerhans, tendon, skin, and vein.

The present disclosure provides an in vitro method for inhibiting complement activation in an organ or a tissue, the method comprising contacting the organ or the tissue with an anti-C1s antibody of any of the embodiments, a solution comprising an anti-C1s antibody of any of the embodiments, or a pharmaceutical composition comprising an anti-C1s antibody of any of the embodiments.

Certain aspects of the invention are defined in the following numbered paragraphs.

1) An antibody that binds a complement C1s protein, wherein the antibody comprises a complementarity-determining region (CDR) having an amino acid sequence selected from the group consisting of SEQ ID NO:1, SEQ ID NO:2, SEQ ID NO:3, SEQ ID NO:4, SEQ ID NO:5, and SEQ ID NO:6.

2) The antibody of paragraph 1, wherein the antibody comprises a light chain variable region comprising amino acid sequences SEQ ID NO:1, SEQ ID NO:2, and SEQ ID NO:3. The antibody of paragraph 1, wherein the antibody comprises a heavy chain variable region comprising amino acid sequences SEQ ID NO:4, SEQ ID NO:5, and SEQ ID NO:6.

3) The antibody of paragraph 1, wherein the antibody comprises a CDR-L1 having amino acid sequence SEQ ID NO:1, a CDR-L2 having amino acid sequence SEQ ID NO:2, a CDR-L3 having amino acid sequence SEQ ID NO:3, a CDR-H1 having amino acid sequence SEQ ID NO:4, a CDR-H2 having amino acid sequence SEQ ID NO:5, and a CDR-H3 having amino acid sequence SEQ ID NO:6.

4) The antibody of paragraph 1, wherein the antibody comprises a light chain variable region comprising an amino acid sequence that is 90% identical to amino acid sequence SEQ ID NO:7. The antibody of paragraph 1, wherein the antibody comprises a heavy chain variable region comprising an amino acid sequence that is 90% identical to amino acid sequence SEQ ID NO:8. The antibody of paragraph 1, wherein the antibody comprises a light chain variable region comprising amino acid sequence SEQ ID NO:7. The antibody of paragraph 1, wherein the antibody comprises a heavy chain variable region comprising amino acid sequence SEQ ID NO:8.

5) The antibody of paragraph 1, wherein the antibody comprises a light chain variable region comprising an amino acid sequence that is 90% identical to amino acid sequence SEQ ID NO:7 and a heavy chain variable region comprising an amino acid sequence that is 90% identical to amino acid sequence SEQ ID NO:8. The antibody of paragraph 1, wherein the antibody comprises a light chain variable region comprising amino acid sequence SEQ ID NO:7 and a heavy chain variable region comprising amino acid sequence SEQ ID NO:8.

6) An antibody that binds a complement C1s protein, wherein the antibody specifically binds an epitope within the complement C1s protein, wherein the antibody competes for binding the epitope with an antibody that comprises light chain CDRs of an antibody light chain variable region comprising amino acid sequence SEQ ID NO:7 and heavy chain CDRs of an antibody heavy chain variable region comprising amino acid sequence SEQ ID NO:8.

7) The antibody of paragraph 6, wherein the antibody comprises light chain CDRs of an antibody light chain variable region comprising amino acid sequence SEQ ID NO:7 and heavy chain CDRs of an antibody heavy chain variable region comprising amino acid sequence SEQ ID NO:8.

8) The antibody of any one of paragraphs 1-7, wherein the antibody binds a human complement C1s protein. The antibody of any one of paragraphs 1-7, wherein the antibody binds a rat complement C1s protein or a monkey complement C1s protein.

9) The antibody of any one of paragraphs 1-8, wherein the antibody inhibits cleavage of at least one substrate cleaved by complement C1s protein.

10) The antibody of paragraph 9, wherein the substrate is selected from the group consisting of complement C2 and complement C4.

11) The antibody of any one of paragraphs 1-10, wherein the antibody comprises a humanized light chain framework region. The antibody of any one of paragraphs 1-10, wherein the antibody comprises a humanized heavy chain framework region.

12) The antibody of any one of paragraphs 1-11, wherein the antibody is selected from the group consisting of an Ig monomer and an antigen-binding fragment thereof that binds complement C1s protein.

13) The antibody of any one of paragraphs 1-11, wherein the antibody is an antigen binding fragment that binds complement C1s protein.

14) The antibody of any one of paragraphs 1-11, wherein the antibody is selected from the group consisting of an Ig monomer, a Fab fragment, a F(ab')$_2$ fragment, a Fd fragment, a scFv, a scAb, a dAb, a Fv, a single domain heavy chain antibody, and a single domain light chain antibody.

15) The antibody of any one of paragraphs 1-11, wherein the antibody is selected from the group consisting of a monospecific antibody, a bi-specific antibody, and a multi-specific antibody. The antibody of any one of paragraphs 1-11, wherein the antibody comprises a light chain region and a heavy chain region that are present in separate polypeptides. The antibody of any one of paragraphs 1-11, wherein the antibody comprises a light chain region and a heavy chain region that are present in a single polypeptide.

16) The antibody of any one of paragraphs 1-11 and 15, wherein the antibody comprises a Fc region.

17) The antibody of any one of paragraphs 1-16, wherein the antibody is encapsulated in a liposome.

18) The antibody of any one of paragraphs 1-16, wherein the antibody comprises a covalently linked non-peptide synthetic polymer.

19) The antibody of paragraph 18, where in the synthetic polymer is a poly(ethylene glycol) polymer.

20) The antibody of any one of paragraphs 1-16, wherein the antibody is formulated with an agent that facilitates crossing the blood-brain barrier.

21) The antibody of any one of paragraphs 1-16, wherein the antibody is fused, directly or through a linker, to a compound that promotes the crossing of the blood-brain barrier, wherein the compound is selected from the group consisting of a carrier molecule, a peptide, or a protein.

BRIEF DESCRIPTION OF THE DRAWINGS

FIG. 1 depicts the amino acid sequence of *Homo sapiens* complement C1s protein (SEQ ID NO:9).

FIG. 2 provides Table 2.

FIG. 9 provides Table 4.

FIG. 12 depicts IPN003 inhibition of rat C1s-mediated cleavage of human C4 and IPN003 inhibition of human C1s-mediated cleavage of human C4.

FIG. 13 depicts the effect of IPN003 on patient serum-mediated hemolysis of human red blood cells.

FIG. 14 depicts the effect of IPN003 on patient serum-mediated C3b deposition on human red blood cells.

FIG. 15 provides amino acid sequences of IPN003 VL and VH regions, IPN003 VL CDRs, and IPN003 VH CDRs.

FIG. 16 depicts an amino acid sequence of humanized IPN003 VH variant 1; and a nucleotide sequence (SEQ ID NO: 46) encoding the amino acid sequence.

FIG. 17 depicts an amino acid sequence of humanized IPN003 VH variant 2; and a nucleotide sequence (SEQ ID NO: 47) encoding the amino acid sequence.

FIG. 18 depicts an amino acid sequence of humanized IPN003 VH variant 3; and a nucleotide sequence (SEQ ID NO: 48) encoding the amino acid sequence.

FIG. 19 depicts an amino acid sequence of humanized IPN003 VH variant 4; and a nucleotide sequence (SEQ ID NO: 49) encoding the amino acid sequence.

FIG. 20 depicts an amino acid sequence of humanized IPN003 Vκ variant 1; and a nucleotide sequence (SEQ ID NO: 50) encoding the amino acid sequence.

FIG. 21 depicts an amino acid sequence of humanized IPN003 Vκ variant 2; and a nucleotide sequence (SEQ ID NO: 51) encoding the amino acid sequence.

FIG. 22 depicts an amino acid sequence of humanized IPN003 Vκ variant 3; and a nucleotide sequence (SEQ ID NO: 52) encoding the amino acid sequence.

FIG. 23 provides Table 7, which shows the amino acid differences between parental IPN003 VH and exemplary VH variants; and Table 8, which shows the amino acid differences between parental IPN003 VL and exemplary VL variants.

FIG. 24 provides Table 9 and 10, which shows binding properties of humanized IPN003 variants to activated C1s and to pro-C1s.

FIG. 25 depicts the IC$_{50}$ of humanized variants of IPN003 for competing with IPN003 for binding to C1s.

FIG. 28 depicts the effect of humanized IPN003 variants on complement-mediated hemolysis and on C3b deposition on antibody-sensitized red blood cells (RBCs).

FIG. 29 depicts inhibition of cold agglutinin disease (CAD) patient plasma-mediated hemolysis by IPN003 or a humanized variant of IPN003 (hu-IPN003).

FIG. 30 depicts inhibition of anaphylatoxin production by IPN003 or hu-IPN003.

FIG. 31 depicts inhibition of CAD patient plasma-mediated C3b deposition on human RBCs by IPN003.

FIG. 32 depicts concentration-dependent inhibition of CAD patient plasma-mediated C3b deposition on human RBCs by IPN003.

DEFINITIONS

Figure 3:
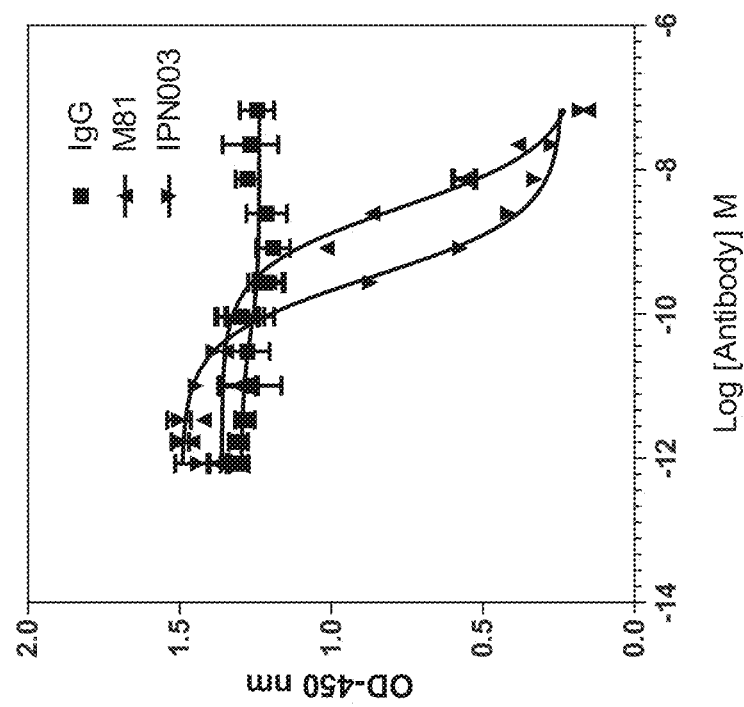
FIG. 3 depicts competition by IPN003 (M34) for binding of M81 to human C1s.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of non-human origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

For example, humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see *Pluckthun in The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A subject anti-C1s antibody binds specifically to an epitope within a complement C1s protein. "Specific binding" refers to binding with an affinity of at least about $10^{-7}$ M or greater, e.g., $5 \times 10^{-7}$ M, $10^{-8}$ M, $5 \times 10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262: 732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs, as defined by each of the above cited references are set forth below in Table 1 as a comparison. The CDRs listed in Table 2 were defined in accordance with Kabat 1991.

TABLE 1

| CDR Definitions | | | |
|---|---|---|---|
| | Kabat[1] | Chothia[2] | MacCallum[3] |
| $V_H$ CDR-1 | 31-35 | 26-32 | 30-35 |
| $V_H$ CDR-2 | 50-65 | 53-55 | 47-58 |
| $V_H$ CDR-3 | 95-102 | 96-101 | 93-101 |
| $V_L$ CDR-1 | 24-34 | 26-32 | 30-36 |
| $V_L$ CDR-2 | 50-56 | 50-52 | 46-55 |
| $V_L$ CDR-3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the terms "CDR-L1", "CDR-L2", and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. Also encompassed by these terms are any animal that has a complement system, such as mammals, fish, and some invertebrates. As such these terms include complement system-containing mammal, fish, and invertebrate companion animals, agricultural animals, work animals, zoo animals, and lab animals.

A "therapeutically effective amount" or "efficacious amount" refers to the amount of an anti-complement C1s antibody that, when administered to a mammal or other subject for treating a disease, is sufficient to effect such treatment for the disease. The "therapeutically effective amount" will vary depending on the anti-complement C1s antibody, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

Before the present invention is further described, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a humanized anti-complement C1s antibody" includes a plurality of such antibodies and reference to "the complement-mediated diseases" includes reference to one or more complement-mediated diseases and equivalents thereof known to those skilled in the art, and so forth. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates, which may need to be independently confirmed.

DETAILED DESCRIPTION

The present disclosure provides an antibody that binds complement C1s protein (i.e., an anti-complement C1s antibody, also referred to herein as an anti-C1s antibody and a C1s antibody) and a nucleic acid molecule that encodes such an antibody. The present disclosure also provides compositions comprising such antibodies, and methods to produce and use such antibodies, nucleic acid molecules, and compositions. The present disclosure provides methods of treating a complement-mediated disease or disorder, involving administering an anti-C1s antibody. The present disclosure further provides in vitro and in vivo detection methods using an anti-C1s antibody described herein.

Anti-Complement C1s Antibodies

The present disclosure provides anti-complement C1s antibodies and pharmaceutical compositions comprising such antibodies. Complement C1s is an attractive target as it is upstream in the complement cascade and has a narrow range of substrate specificity. Furthermore it is possible to obtain antibodies (for example, but not limited to, monoclonal antibodies) that specifically bind the activated form of C1s.

The present disclosure provides an isolated antibody that specifically binds an epitope within a complement C1s protein. As used herein, unless denoted otherwise, a complement C1s protein is an activated C1s protein. In some embodiments, an isolated anti-C1s antibody of the present disclosure binds an activated C1s protein. In some embodiments, an isolated anti-C1s antibody of the present disclosure binds an inactive form of C1s. In other instances, an isolated anti-C1s antibody of the present disclosure binds both an activated C1s protein and an inactive form of C1s. In some instances, the antibody is humanized, e.g., one or more framework regions of the heavy chain variable region and/or the light chain variable region include sequences derived from a human immunoglobulin framework.

The present disclosure provides an isolated monoclonal antibody that inhibits cleavage of C4, where the isolated monoclonal antibody does not inhibit cleavage of C2. In some cases, the isolated monoclonal antibody is humanized. In some cases, the antibody inhibits a component of the classical complement pathway. In some cases, the component of the classical complement pathway that is inhibited by the antibody is C1s. The present disclosure also provides methods of treating a complement-mediated disease or disorder, the method comprising administering to an individual in need thereof an effective amount of an isolated monoclonal antibody that inhibits cleavage of C4, or a pharmaceutical composition comprising the isolated monoclonal antibody, where the isolated monoclonal antibody does not inhibit cleavage of C2.

The present disclosure provides an isolated monoclonal antibody that inhibits cleavage of C4 by C1s, i.e., inhibits C1s-mediated proteolytic cleavage of C4. In some cases, the isolated monoclonal antibody is humanized. In some cases, the antibody inhibits cleavage of C4 by C1s by inhibiting binding of C4 to C1s; for example, in some cases, the antibody inhibits C1s-mediated cleavage of C4 by inhibiting binding of C4 to a C4 binding site of C1s. Thus, in some cases, the antibody functions as a competitive inhibitor. The present disclosure also provides methods of treating a complement-mediated disease or disorder, the method comprising administering to an individual in need thereof an effective amount of an isolated monoclonal antibody that inhibits cleavage of C4 by C1s, i.e., inhibits C1s-mediated proteolytic cleavage of C4.

The present disclosure provides an isolated monoclonal antibody that inhibits cleavage of C4 by C1s, where the antibody does not inhibit cleavage of complement component C2 by C1s; i.e., the antibody inhibits C1s-mediated cleavage of C4, but does not inhibit C1s-mediated cleavage of C2. In some cases, the isolated monoclonal antibody is humanized. In some cases, the monoclonal antibody inhibits binding of C4 to C1s, but does not inhibit binding of C2 to C1s. The present disclosure also provides methods of treating a complement-mediated disease or disorder, the method comprising administering to an individual in need thereof an effective amount of an isolated monoclonal antibody that inhibits cleavage of C4 by C1s, where the antibody does not inhibit cleavage of complement component C2 by C1s; i.e., the antibody inhibits C1s-mediated cleavage of C4, but does not inhibit C1s-mediated cleavage of C2. In some embodiments of the method, the antibody is humanized.

The present disclosure provides an isolated humanized monoclonal antibody that specifically binds an epitope within a region encompassing domains IV and V of C1s. For example, the present disclosure provides an isolated humanized monoclonal antibody that specifically binds an epitope within amino acids 272-422 of the amino acid sequence depicted in FIG. 1 and set forth in SEQ ID NO:9. In some cases, the isolated humanized monoclonal antibody specifically binds an epitope within amino acids 272-422 of the amino acid sequence depicted in FIG. 1 and set forth in SEQ ID NO:9, and inhibits binding of C4 to C1s. The present disclosure also provides methods of treating a complement-mediated disease or disorder, the method comprising administering to an individual in need thereof an effective amount of an isolated humanized monoclonal antibody that specifically binds an epitope within amino acids 272-422 of the amino acid sequence depicted in FIG. 1 and set forth in SEQ ID NO:9, and inhibits binding of C4 to C1s.

The present disclosure provides an isolated humanized monoclonal antibody that specifically binds a conformational epitope within a region encompassing domains IV and V of C1s. For example, the present disclosure provides an isolated humanized monoclonal antibody that specifically binds a conformational epitope within amino acids 272-422 of the amino acid sequence depicted in FIG. 1 and set forth in SEQ ID NO:9. In some cases, the isolated humanized monoclonal antibody specifically binds a conformational epitope within amino acids 272-422 of the amino acid sequence depicted in FIG. 1 and set forth in SEQ ID NO:9, and inhibits binding of C4 to C1s. The present disclosure also provides methods of treating a complement-mediated disease or disorder, the method comprising administering to an individual in need thereof an effective amount of an isolated humanized monoclonal antibody that specifically binds a conformational epitope within amino acids 272-422 of the amino acid sequence depicted in FIG. 1 and set forth in SEQ ID NO:9, and inhibits binding of C4 to C1s.

The present disclosure provides an isolated monoclonal antibody that binds complement component C1s in a C1 complex. The C1 complex is composed of 6 molecules of C1q, 2 molecules of C1r, and 2 molecules of C1s. In some cases, the isolated monoclonal antibody is humanized. Thus, in some cases, the present disclosure provides an isolated humanized monoclonal antibody that binds complement component C1s in a C1 complex. In some cases, the antibody binds C1s present in a C1 complex with high avidity.

Humanization of a framework region(s) reduces the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of the therapy. The HAMA response is measured, for example, by detecting antibodies to the humanized therapeutic reagent, in serum samples from the patient using a method known to one in the art, including surface plasmon resonance technology (BIACORE) and/or solid-phase enzyme-linked immunosorbent assay (ELISA) analysis. In many cases, a subject humanized anti-C1s antibody does not substantially elicit a HAMA response in a human subject.

Certain amino acids from the human variable region framework residues are selected for substitution based on their possible influence on CDR conformation and/or binding antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, e.g., those sharing at least 60%, at least 70%, at least 80%, at least 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody can be selected for substitution into the humanized antibody. Residues that are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids can interact directly with the antigen (Amit et al., Science, 233:747 (1986)) and selecting these amino acids from the donor can be desirable to keep all the antigen contacts that provide affinity in the original antibody.

In some embodiments, an anti-C1s antibody of the present disclosure (e.g., a subject antibody that specifically binds an epitope in a complement C1s protein) comprises: a) a light chain region comprising one, two, or three $V_L$ CDRs of an IPN003 antibody; and b) a heavy chain region comprising one, two, or three $V_H$ CDRs of an IPN003 antibody; where the $V_H$ and $V_L$ CDRs are as defined by Kabat (see, e.g., Table 1, above; and Kabat 1991). In some of these embodiments, the anti-C1s antibody includes a humanized $V_H$ and/or $V_L$ framework region (FR).

In some embodiments, an anti-C1s antibody of the present disclosure (e.g., a subject antibody that specifically binds an epitope in a complement C1s protein) comprises: a) a light chain region comprising one, two, or three $V_L$ CDRs of an IPN003 antibody; and b) a heavy chain region comprising one, two, or three $V_H$ CDRs of an IPN003 antibody; where the $V_H$ and $V_L$ CDRs are as defined by Chothia (see, e.g., Table 1, above; and Chothia 1987). In some of these embodiments, the anti-C1s antibody includes a humanized $V_H$ and/or $V_L$ framework region.

CDR amino acid sequences, and $V_L$ and $V_H$ amino acid sequences, of IPN003 antibody are provided in Table 2 (FIG. 2). Table 2 also provides the SEQ ID NOs assigned to each of the amino acid sequences.

In some embodiments, an anti-C1s antibody of the present disclosure (e.g., a subject antibody that specifically binds an epitope in a complement C1s protein) comprises: a) a light chain region comprising one, two, or three CDRs selected from SEQ ID NO:1, SEQ ID NO:2, and SEQ ID NO:3; and b) a heavy chain region comprising one, two, or three CDRs selected from SEQ ID NO:4, SEQ ID NO:5, and SEQ ID NO:6. In some of these embodiments, the anti-C1s antibody includes a humanized $V_H$ and/or $V_L$ framework region.

```
SEQ ID NO: 1:       SSVSSSYLHWYQ;

SEQ ID NO: 2:       STSNLASGVP;

SEQ ID NO: 3:       HQYYRLPPIT;

SEQ ID NO: 4:       GFTFSNYAMSWV;

SEQ ID NO: 5:       ISSGGSHTYY;

SEQ ID NO: 6:       ARLFTGYAMDY.
```

In some embodiments, an anti-C1s antibody of the present disclosure comprises a CDR having an amino acid sequence selected from the group consisting of SEQ ID NO:1, SEQ ID NO:2, SEQ ID NO:3, SEQ ID NO:4, SEQ ID NO:5, and SEQ ID NO:6.

In some embodiments, an anti-C1s antibody of the present disclosure comprises a light chain variable region comprising amino acid sequences SEQ ID NO:1, SEQ ID NO:2, and SEQ ID NO:3.

In some embodiments, an anti-C1s antibody of the present disclosure comprises a heavy chain variable region comprising amino acid sequences SEQ ID NO:4, SEQ ID NO:5, and SEQ ID NO:6.

In some embodiments, an anti-C1s antibody of the present disclosure comprises a CDR-L1 having amino acid sequence SEQ ID NO:1, a CDR-L2 having amino acid sequence SEQ ID NO:2, a CDR-L3 having amino acid sequence SEQ ID NO:3, a CDR-H1 having amino acid sequence SEQ ID NO:4, a CDR-H2 having amino acid sequence SEQ ID NO:5, and a CDR-H3 having amino acid sequence SEQ ID NO:6.

In some embodiments, an anti-C1s antibody of the present disclosure comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:7.

```
SEQ ID NO: 7: DIVMTQTTAIMSASLGERVTMTCTASSSVSSSYLHWYQQKPGSSPKLWIYSTSNLASGV

PARFSGSGSGTFYSLTISSMEAEDDATYYCHQYYRLPPITFGAGTKLELK.
```

In some embodiments, an anti-C1s antibody of the present disclosure comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:8.

```
SEQ ID NO: 8: QVKLEESGGALVKPGGSLKLSCAASGFTFSNYAMSWVRQIPEKRLEWVATISSGGSHTY

YLDSVKGRFTISRDNARDTLYLQMSSLRSEDTALYYCARLFTGYAMDYWGQGTSVT.
```

In some embodiments, an anti-C1s antibody of the present disclosure comprises a light chain variable region comprising an amino acid sequence that is 90% identical to amino acid sequence SEQ ID NO:7.

In some embodiments, an anti-C1s antibody of the present disclosure comprises a heavy chain variable region comprising an amino acid sequence that is 90% identical to amino acid sequence SEQ ID NO:8.

In some embodiments, an anti-C1s antibody of the present disclosure comprises a light chain variable region comprising amino acid sequence SEQ ID NO:7.

In some embodiments, an anti-C1s antibody of the present disclosure comprises a heavy chain variable region comprising amino acid sequence SEQ ID NO:8.

In some embodiments, an anti-C1s antibody of the present disclosure comprises a light chain variable region comprising an amino acid sequence that is 90% identical to amino acid sequence SEQ ID NO:7 and a heavy chain variable region comprising an amino acid sequence that is 90% identical to amino acid sequence SEQ ID NO:8.

In some embodiments, an anti-C1s antibody of the present disclosure comprises a light chain variable region comprising amino acid sequence SEQ ID NO:7 and a heavy chain variable region comprising amino acid sequence SEQ ID NO:8.

In some embodiments, an anti-C1s antibody of the present disclosure specifically binds an epitope within the complement C1s protein, wherein the antibody competes for binding the epitope with an antibody that comprises light chain CDRs of an antibody light chain variable region comprising amino acid sequence SEQ ID NO:7 and heavy chain CDRs of an antibody heavy chain variable region comprising amino acid sequence SEQ ID NO:8.

In some embodiments, an anti-C1s antibody of the present disclosure comprises light chain CDRs of an antibody light chain variable region comprising amino acid sequence SEQ ID NO:7 and heavy chain CDRs of an antibody heavy chain variable region comprising amino acid sequence SEQ ID NO:8.

In some cases, a humanized $V_H$ framework or $V_L$ framework is a consensus human framework. A consensus humanized framework can represent the most commonly occurring amino acid residue in a selection of human immunoglobulin $V_L$ or $V_H$ framework sequences.

Non-limiting examples of consensus human $V_H$ framework regions suitable for use with $V_H$ CDRs as described herein include (subgroup III consensus):

```
a) V_H FR1: EVQLVESGGGLVQPGGSLRLSCAAS     (SEQ ID NO:
                                          53);
```

-continued

```
b) V_H FR2: WVRQAPGKGLEWV                 (SEQ ID NO:
                                          54);
```

-continued

```
c) V_H FR3: RFTISRDNSKNTLYLQMNSLRAEDTAVYYC (SEQ ID NO:
                                           55); and d) V_H FR4: WGQGTLVTVSS                    (SEQ ID NO:
                                           56).
```

In some cases, $V_H$ FR3 comprises an amino acid substitution at position 71, 73, and/or 78; e.g., where the underlined and bolded R in RFTIS<u>R</u>DNSKNTLYLQMNSLRAEDTAVYYC (SEQ ID NO:55) is amino acid 71 (Kabat numbering); the underlined and bolded N in RFTISRD<u>N</u>SKNTLYLQMNSLRAEDTAVYYC (SEQ ID NO:55) is amino acid 73 (Kabat numbering); and the underlined and bolded L in RFTISRDNSKNT<u>L</u>YLQMNSLRAEDTAVYYC (SEQ ID NO:55) is amino acid 78 (Kabat numbering). For example, in some cases, amino acid 71 is A; and/or amino acid 73 is T; and/or amino acid 78 is A. As an example, in some cases, a suitable consensus humanized $V_H$ FR3 comprises the amino acid sequence: RFTIS<u>A</u>D<u>T</u>SKNT<u>A</u>YLQMNSLRAEDTAVYYC (SEQ ID NO:57).

Non-limiting examples of consensus human $V_H$ framework regions suitable for use with $V_H$ CDRs as described herein include (subgroup I consensus):

```
a) V_H FR1: QVQLVQSGAEVKKPGASVKVSCKAS     (SEQ ID NO:
                                          58);

b) V_H FR2: WVRQAPGQGLEWM                 (SEQ ID NO:
                                          59);

c) V_H FR3: RVTITADTSTSTAYMELSSLRSEDTAVYYC (SEQ ID NO:
                                           60); and d) V_H FR4: WGQGTLVTVSS                    (SEQ ID NO:
                                           56).
```

Non-limiting examples of consensus human $V_H$ framework regions suitable for use with $V_H$ CDRs as described herein include (subgroup II consensus):

a)  $V_H$ FR1: QVQLQESGPGLVKPSQTLSLTCTVS (SEQ ID NO: 61);

b)  $V_H$ FR2: WIRQPPGKGLEWI (SEQ ID NO: 62);

c)  $V_H$ FR3: RVTISVDTSKNQFSLKLSSVTAADTAVYYC (SEQ ID NO: 63); and d)  $V_H$ FR4: WGQGTLVTVSS (SEQ ID NO: 56).

Non-limiting examples of consensus human $V_L$ framework regions suitable for use with $V_L$ CDRs as described herein include (subgroup I consensus):

a)  $V_L$ FR1: DIQMTQSPSSLSASVGDRVTITC (SEQ ID NO: 57);

b)  $V_L$ FR2: WYQQKPGKAPKLLIY (SEQ ID NO: 58);

c)  $V_L$ FR3: GVPSRFSGSGSGTDFTLTISSLQPEDFATYYC (SEQ ID NO: 59); and d)  $V_L$ FR4: FGQGTKVEIK (SEQ ID NO: 60).

Non-limiting examples of consensus human $V_L$ framework regions suitable for use with $V_L$ CDRs as described herein include (subgroup II consensus):

a)  $V_L$ FR1: DIVMTQSPLSLPVTPGEPASISC (SEQ ID NO: 64);

b)  $V_L$ FR2: WYLQKPGQSPQLLIY (SEQ ID NO: 65);

c)  $V_L$ FR3: GVPDRFSGSGSGTDFTLKISRVEAEDVGVYYC (SEQ ID NO: 66); and d)  $V_L$ FR4: FGQGTKVEIK (SEQ ID NO: 60).

Non-limiting examples of consensus human $V_L$ framework regions suitable for use with $V_L$ CDRs as described herein include (subgroup III consensus):

a)  $V_L$ FR1: DIVMTQSPDSLAVSLGERATINC (SEQ ID NO: 67);

b)  $V_L$ FR2: WYQQKPGQPPKLLIY (SEQ ID NO: 68);

c)  $V_L$ FR3: GVPDRFSGSGSGTDFTLTISSLQAEDFAVYYC (SEQ ID NO: 69); and d)  $V_L$ FR4: FGQGTKVEIK (SEQ ID NO: 60).

Non-limiting examples of consensus human $V_L$ framework regions suitable for use with $V_L$ CDRs as described herein include (subgroup IV consensus):

a)  $V_L$ FR1: DIVMTQSPDSLAVSLGERATINC (SEQ ID NO: 67);

b)  $V_L$ FR2: WYQQKPGQPPKLLIY (SEQ ID NO: 68);

c)  $V_L$ FR3: GVPDRFSGSGSGTDFTLTISSLQAEDFAVYYC (SEQ ID NO: 69); and d)  $V_L$ FR4: FGQGTKVEIK (SEQ ID NO: 60).

In some embodiments, an anti-C1s antibody of the present disclosure binds a complement C1s protein from an individual that has a complement system. In some embodiments, an anti-C1s antibody of the present disclosure binds a complement C1s protein from a mammal, fish, or invertebrate that has a complement system. In some embodiments, an anti-C1s antibody of the present disclosure binds a mammalian complement C1s protein. In some embodiments, an anti-C1s antibody of the present disclosure binds a human complement C1s protein. In some embodiments, an anti-C1s antibody of the present disclosure binds a rat complement C1s protein. In some embodiments, an anti-C1s antibody of the present disclosure binds a complement C1s protein having SEQ ID NO:9). Amino acid sequence SEQ ID NO:9 represents *Homo sapiens* complement C1s protein, which has the amino acid sequence set forth in FIG. 1.

In some embodiments, an anti-C1s antibody of the present disclosure binds a complement C1s protein with a dissociation constant ($K_D$) of no more than 2.5 nM. In some embodiments, an anti-C1s antibody of the present disclosure binds a complement C1s protein with a $K_D$ of no more than 2 nM. In some embodiments, an anti-C1s antibody of the present disclosure binds a complement C1s protein with a $K_D$ of no more than 1 nM. In some embodiments, an anti-C1s antibody of the present disclosure binds a complement C1s protein with a $K_D$ of no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM. In some embodiments, an anti-C1s antibody of the present disclosure binds a complement C1s protein with a $K_D$ of no more than 0.3 nM. In some embodiments, an anti-C1s antibody of the present disclosure binds a complement C1s protein with a $K_D$ of no more than 0.2 nM. In some embodiments, an anti-C1s antibody of the present disclosure binds a complement C1s protein with a $K_D$ of no more than 0.1 nM. Methods to measure binding of an antibody to C1s protein can be determined by one skilled in the art.

In some embodiments, an anti-C1s antibody of the present disclosure binds a complement C1s protein with a $K_D$ of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, no more than 1 pM.

In some embodiments, an anti-C1s antibody of the present disclosure binds a human complement C1s protein with a dissociation constant ($K_D$) of no more than 2.5 nM. In some embodiments, an anti-C1s antibody of the present disclosure binds a human complement C1s protein with a $K_D$ of no more than 2 nM. In some embodiments, an anti-C1s antibody of the present disclosure binds a human complement C1s protein with a $K_D$ of no more than 1 nM. In some embodiments, an anti-C1s antibody of the present disclosure binds a human complement C1s protein with a $K_D$ of no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM. In some embodiments, an anti-C1s antibody of the present disclosure binds a human complement C1s protein with a $K_D$ of no more than 0.3 nM. In some embodiments, an anti-C1s antibody of the present disclosure binds a human complement C1s protein with a $K_D$ of no more than 0.2 nM. In some embodiments, an anti-C1s antibody of the present disclosure binds a human complement C1s protein with a $K_D$ of no more than 0.1 nM. Methods to measure binding of an antibody to human C1s protein can be determined by one skilled in the art. In some embodiments, a binding assay as described in the Examples is used to determine the $K_D$ between an antibody and a human C1s protein.

In some embodiments, an anti-C1s antibody of the present disclosure binds a human complement C1s protein with a $K_D$ of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, no more than 1 pM.

In some embodiments, an anti-C1s antibody of the present disclosure that binds human complement C1s protein also binds a complement C1s protein of another species. In some embodiments, an anti-C1s antibody of the present disclosure that binds human complement C1s protein also binds a rodent complement C1s protein. Examples of rodent complement C1s proteins include, but are not limited to, guinea pig C1s proteins, hamster C1s proteins, mouse C1s proteins, and rat C1s proteins. In some embodiments, an anti-C1s antibody of the present disclosure that binds human complement C1s protein also binds a lagomorph complement C1s protein, e.g., a rabbit C1s protein. In some embodiments, an anti-C1s antibody of the present disclosure that binds human complement C1s protein also binds a non-human primate complement C1s protein, where exemplary non-human primates include monkeys such as *Macaca mulatta*, and *Macaca fascicularis*. In some embodiments, such a cross-reactive antibody binds the complement C1s protein of another (non-human) species with a $K_D$ of a similar order of magnitude as the antibody binds a human complement C1s protein. In some embodiments an anti-C1s antibody of the present disclosure binds a rat complement C1s protein. In some embodiments an anti-C1s antibody of the present disclosure that binds human complement C1s protein also binds a rat complement C1s protein.

In some embodiments, an anti-C1s antibody of the present disclosure binds a rat complement C1s protein with a dissociation constant ($K_D$) of no more than 2.5 nM. In some embodiments, an anti-C1s antibody of the present disclosure binds a rat complement C1s protein with a $K_D$ of no more than 2 nM. In some embodiments, an anti-C1s antibody of the present disclosure binds a rat complement C1s protein with a $K_D$ of no more than 1 nM. In some embodiments, an anti-C1s antibody of the present disclosure binds a rat complement C1s protein with a $K_D$ of no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM. In some embodiments, an anti-C1s antibody of the present disclosure binds a rat complement C1s protein with a $K_D$ of no more than 0.3 nM. In some embodiments, an anti-C1s antibody of the present disclosure binds a rat complement C1s protein with a $K_D$ of no more than 0.2 nM. In some embodiments, an anti-C1s antibody of the present disclosure binds a rat complement C1s protein with a $K_D$ of no more than 0.1 nM. Methods to measure binding of an antibody to rat C1s protein can be determined by one skilled in the art. In some embodiments, a binding assay as described in the Examples is used to determine the $K_D$ between an antibody and a rat C1s protein.

In some embodiments, an anti-C1s antibody of the present disclosure binds a rat complement C1s protein with a $K_D$ of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, no more than 1 pM.

In some embodiments, an anti-C1s antibody of the present disclosure binds both native complement C1s protein and denatured complement C1s protein. "Native protein" as used herein refers to protein as folded in its naturally-occurring physiological state, and thus excludes denatured protein. Detection of binding can be conducted by western blot. In such embodiments, an anti-C1s antibody of the present disclosure binds C1s protein applied to a native gel and also binds C1s protein applied to a denatured (e.g., sodium dodecyl sulfate (SDS)) gel. In some embodiments, a subject anti-C1s antibody of the present disclosure binds a linear epitope in C1s. Methods to determine if an antibody binds a native C1s protein or a denatured C1s protein are known to those skilled in the art. In some embodiments, gel electrophoresis is used to determine if an antibody binds a native and/or a denatured C1s protein.

In some embodiments, an anti-C1s antibody of the present disclosure reduces production of C4b2a (i.e., complement C4b and C2a complex; also known as "C3 convertase") by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C4b2a produced in the absence of a subject anti-C1s antibody. Methods to measure production of C4b2a are known in the art.

In some embodiments, an anti-C1s antibody of the present disclosure inhibits cleavage of at least one substrate cleaved by complement C1s protein. In some embodiments, the substrate is selected from the group consisting of complement C2 and complement C4. In some embodiments, the substrate is complement C2. In some embodiments the substrate is complement C4. In some embodiments, an anti-C1s antibody of the present disclosure inhibits cleavage of complement C2. In some embodiments, an anti-C1s antibody of the present disclosure inhibits cleavage of complement C4. In some embodiments, an anti-C1s antibody of the present disclosure inhibits cleavage of complement C2 and complement C4.

In some embodiments, an anti-C1s antibody of the present disclosure inhibits cleavage of at least one substrate cleaved by human complement C1s protein. In some embodiments, the substrate is selected from the group consisting of human complement C2 and human complement C4. In some embodiments, the substrate is human complement C2. In some embodiments the substrate is human complement C4. In some embodiments, an anti-C1s antibody of the present disclosure inhibits cleavage of human complement C2. In some embodiments, an anti-C1s antibody of the present disclosure inhibits cleavage of human complement C4. In some embodiments, an anti-C1s antibody of the present disclosure inhibits cleavage of human complement C2 and human complement C4. In some embodiments, an anti-C1s antibody of the present disclosure inhibits rat C1s-mediated cleavage of human complement C4. In some embodiments, an anti-C1s antibody of the present disclosure inhibits human C1s-mediated cleavage of human complement C4.

In some embodiments, an anti-C1s antibody of the present disclosure inhibits cleavage of at least one substrate cleaved by rat complement C1s protein. In some embodiments, the substrate is selected from the group consisting of rat complement C2 and rat complement C4. In some embodiments, the substrate is rat complement C2. In some embodiments the substrate is rat complement C4. In some embodiments, an anti-C1s antibody of the present disclosure inhibits cleavage of rat complement C2. In some embodiments, an anti-C1s antibody of the present disclosure inhibits cleavage of rat complement C4. In some embodiments, an anti-C1s antibody of the present disclosure inhibits cleavage of rat complement C2 and rat complement C4.

In some embodiments, an anti-C1s antibody of the present disclosure inhibits C1s by sterically blocking access to the C1s active site or by sterically blocking access to the substrate.

In some embodiments, an anti-C1s antibody of the present disclosure inhibits C1s-mediated activation of complement C4. For example, in some cases, an anti-C1s antibody of the present disclosure inhibits C1s-mediated activation of complement C4 with an $IC_{50}$ less than $50 \times 10^{-9}$ M, less than $25 \times 10^{-9}$ M, less than $10 \times 10^{-9}$ M, less than $5 \times 10^{-9}$ M, less than $1 \times 10^{-9}$ M, less than $0.5 \times 10^{-9}$ M, less than $0.1 \times 10^{-9}$ M, or less than $0.1 \times 10^{-10}$ M.

In some instances, an anti-C1s antibody of the present disclosure inhibits complement-mediated cell lysis, e.g., in an in vitro cell lysis assay. For example, in some instances, an anti-C1s antibody of the present disclosure inhibits complement-mediated cell lysis with an $IC_{50}$ of less than $10 \times 10^{-9}$ M, less than $5 \times 10^{-9}$ M, less than $1 \times 10^{-9}$ M, less than $0.5 \times 10^{-9}$ M, less than $0.1 \times 10^{-9}$ M, or less than $0.1 \times 10^{-10}$ M.

In some embodiments, an anti-C1s antibody of the present disclosure competes for binding the epitope bound by IPN003.

In some embodiments, an anti-C1s antibody of the present disclosure comprises a variable domain of an IPN003 antibody.

In some embodiments, an anti-C1s antibody of the present disclosure is an IPN003 antibody.

The present disclosure provides for any anti-C1s antibody of the embodiments to be humanized. In some embodiments, an anti-C1s antibody of the present disclosure comprises a humanized framework region. In some embodiments, an anti-C1s antibody of the present disclosure comprises a humanized light chain framework region. In some embodiments, an anti-C1s antibody of the present disclosure comprises a humanized heavy chain framework region.

In some embodiments, a subject anti-C1s antibody comprises one or more humanized framework regions (FRs). In some embodiments, a subject anti-C1s antibody comprises a light chain variable region comprising one, two, three, or four light chain FRs that have been humanized. In some embodiments, a subject antibody comprises a light chain variable region comprising, in order from N-terminus to C-terminus: a humanized light chain FR1; a CDR-L1 as set forth herein; a humanized light chain FR2; a CDR-L2 as set forth herein; a humanized light chain FR3; a CDR-L3 as set forth herein; and a humanized light chain FR4. In some embodiments, the respective amino acid sequences of CDR-L1, CDR-L2, and CDR-L3 are: SEQ ID NO:1, SEQ ID NO:2, and SEQ ID NO:3.

For example, a subject antibody can comprise a light chain variable region that comprises, in order from N-terminus to C-terminus: a humanized light chain FR1; a CDR-L1 comprising amino acid sequence SEQ ID NO:1; a humanized light chain FR2; a CDR-L2 comprising amino acid sequence SEQ ID NO:2; a humanized light chain FR3; a CDR-L3 comprising amino acid sequence SEQ ID NO:3; and a humanized light chain FR4.

In some embodiments, a subject anti-C1s antibody comprises a heavy chain variable region comprising one, two, three, or four heavy chain FRs that have been humanized. In some embodiments, a subject antibody comprises a heavy chain variable region comprising, in order from N-terminus to C-terminus: a humanized heavy chain FR1; a CDR-H1 as set forth herein; a humanized heavy chain FR2; a CDR-H2 as set forth herein; a humanized heavy chain FR3; a CDR-H3 as set forth herein; and a humanized heavy chain FR4.

For example, a subject antibody can comprise a heavy chain variable region that comprises, in order from N-terminus to C-terminus: a humanized heavy chain FR1; a CDR-H1 comprising amino acid sequence SEQ ID NO:4; a humanized heavy chain FR2; a CDR-H2 comprising amino acid sequence SEQ ID NO:5; a humanized heavy chain FR3; a CDR-H3 comprising amino acid sequence SEQ ID NO:6; and a humanized heavy chain FR4.

In some embodiments, an anti-C1s antibody of the present disclosure (e.g., a subject antibody that specifically binds an epitope in a complement C1s protein) comprises: a) a light chain region comprising one, two, or three CDRs selected from SEQ ID NO:32, SEQ ID NO:33, and SEQ ID NO:3; and b) a heavy chain region comprising one, two, or three CDRs selected from SEQ ID NO:34, SEQ ID NO:35, and SEQ ID NO:36. In some of these embodiments, the anti-C1s antibody includes a humanized $V_H$ and/or $V_L$ framework region.

```
SEQ ID NO: 32:      TASSSVSSSYLH;

SEQ ID NO: 33:      STSNLAS;

SEQ ID NO: 3:       HQYYRLPPIT;

SEQ ID NO: 34:      NYAMS;

SEQ ID NO: 35:      TISSGGSHTYYLDSVKG;

SEQ ID NO: 36:      LFTGYAMDY.
```

In some embodiments, an anti-C1s antibody of the present disclosure comprises a CDR having an amino acid sequence selected from the group consisting of SEQ ID NO:32, SEQ ID NO:33, SEQ ID NO:3, SEQ ID NO:34, SEQ ID NO:35, and SEQ ID NO:36.

In some embodiments, an anti-C1s antibody of the present disclosure comprises a light chain variable region comprising amino acid sequences SEQ ID NO:32, SEQ ID NO:33, and SEQ ID NO:3.

In some embodiments, an anti-C1s antibody of the present disclosure comprises a heavy chain variable region comprising amino acid sequences SEQ ID NO:34, SEQ ID NO:35, and SEQ ID NO:36.

In some embodiments, an anti-C1s antibody of the present disclosure comprises a CDR-L1 having amino acid sequence SEQ ID NO:32, a CDR-L2 having amino acid sequence SEQ ID NO:33, a CDR-L3 having amino acid sequence SEQ ID NO:3, a CDR-H1 having amino acid sequence SEQ ID NO:34, a CDR-H2 having amino acid sequence SEQ ID NO:35, and a CDR-H3 having amino acid sequence SEQ ID NO:36.

In some embodiments, an anti-C1s antibody of the present disclosure comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:37.

In some embodiments, an anti-C1s antibody of the present disclosure comprises a light chain variable region comprising amino acid sequence SEQ ID NO:37 and a heavy chain variable region comprising amino acid sequence SEQ ID NO:38.

In some embodiments, an anti-C1s antibody of the present disclosure specifically binds an epitope within the complement C1s protein, wherein the antibody competes for binding the epitope with an antibody that comprises light chain CDRs of an antibody light chain variable region comprising amino acid sequence SEQ ID NO:37 and heavy chain CDRs of an antibody heavy chain variable region comprising amino acid sequence SEQ ID NO:38.

In some embodiments, an anti-C1s antibody of the present disclosure comprises light chain CDRs of an antibody light chain variable region comprising amino acid sequence SEQ ID NO:37 and heavy chain CDRs of an antibody heavy chain variable region comprising amino acid sequence SEQ ID NO:38.

In some embodiments, a subject anti-C1s antibody comprises one or more humanized framework regions (FRs). In some embodiments, a subject anti-C1s antibody comprises a light chain variable region comprising one, two, three, or four

```
SEQ ID NO: 37: QIVLTQSPAIMSASLGERVTMTCTASSSVSSSYLHWYQQKPGSSPKLWIYSTSNLASGVP

ARFSGSGSGTFYSLTISSMEAEDDATYYCHQYYRLPPITFGAGTKLELK.
```

In some embodiments, an anti-C1s antibody of the present disclosure comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:38.

light chain FRs that have been humanized. In some embodiments, a subject antibody comprises a light chain variable region comprising, in order from N-terminus to C-terminus: a humanized light chain FR1; a CDR-L1 as set forth herein; a humanized light chain FR2; a CDR-L2 as set forth herein; a humanized light chain FR3; a CDR-L3 as set forth herein; and

```
SEQ ID NO: 38: EVMLVESGGALVKPGGSLKLSCAASGFTFSNYAMSWVRQIPEKRLEWVATISSGGSHT

YYLDSVKGRFTISRDNARDTLYLQMSSLRSEDTALYYCARLFTGYAMDYWGQGTSVT

VSS.
```

In some embodiments, an anti-C1s antibody of the present disclosure comprises a light chain variable region comprising an amino acid sequence that is 90% identical to amino acid sequence SEQ ID NO:37.

In some embodiments, an anti-C1s antibody of the present disclosure comprises a heavy chain variable region comprising an amino acid sequence that is 90% identical to amino acid sequence SEQ ID NO:38.

In some embodiments, an anti-C1s antibody of the present disclosure comprises a light chain variable region comprising amino acid sequence SEQ ID NO:37.

In some embodiments, an anti-C1s antibody of the present disclosure comprises a heavy chain variable region comprising amino acid sequence SEQ ID NO:38.

In some embodiments, an anti-C1s antibody of the present disclosure comprises a light chain variable region comprising an amino acid sequence that is 90% identical to amino acid sequence SEQ ID NO:37 and a heavy chain variable region comprising an amino acid sequence that is 90% identical to amino acid sequence SEQ ID NO:38.

In some embodiments, an anti-C1s antibody of the present disclosure comprises a light chain variable region comprising an amino acid sequence that is 95% identical to amino acid sequence SEQ ID NO:37 and a heavy chain variable region comprising an amino acid sequence that is 95% identical to amino acid sequence SEQ ID NO:38.

a humanized light chain FR4. In some embodiments, the respective amino acid sequences of CDR-L1, CDR-L2, and CDR-L3 are: SEQ ID NO:32, SEQ ID NO:33, and SEQ ID NO:3.

For example, a subject antibody can comprise a light chain variable region that comprises, in order from N-terminus to C-terminus: a humanized light chain FR1; a CDR-L1 comprising amino acid sequence SEQ ID NO:32; a humanized light chain FR2; a CDR-L2 comprising amino acid sequence SEQ ID NO:33; a humanized light chain FR3; a CDR-L3 comprising amino acid sequence SEQ ID NO:3; and a humanized light chain FR4.

In some embodiments, a subject anti-C1s antibody comprises a heavy chain variable region comprising one, two, three, or four heavy chain FRs that have been humanized. In some embodiments, a subject antibody comprises a heavy chain variable region comprising, in order from N-terminus to C-terminus: a humanized heavy chain FR1; a CDR-H1 as set forth herein; a humanized heavy chain FR2; a CDR-H2 as set forth herein; a humanized heavy chain FR3; a CDR-H3 as set forth herein; and a humanized heavy chain FR4.

For example, a subject antibody can comprise a heavy chain variable region that comprises, in order from N-terminus to C-terminus: a humanized heavy chain FR1; a CDR-H1 comprising amino acid sequence SEQ ID NO:34; a humanized heavy chain FR2; a CDR-H2 comprising amino acid sequence SEQ ID NO:35; a humanized heavy chain FR3; a CDR-H3 comprising amino acid sequence SEQ ID NO:36; and a humanized heavy chain FR4.

In some embodiments, an anti-C1s antibody of the present disclosure comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:37.

In some embodiments, an anti-C1s antibody of the present disclosure comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:38.

A subject anti-C1s antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:39 and depicted in FIG. 16 (VH variant 1).

A subject anti-C1s antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:40 and depicted in FIG. 17 (VH variant 2).

A subject anti-C1s antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:41 and depicted in FIG. 18 (VH variant 3).

A subject anti-C1s antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:42 and depicted in FIG. 19 (VH variant 4).

A subject anti-C1s antibody can comprise a light chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:43 and depicted in FIG. 20 (VK variant 1).

A subject anti-C1s antibody can comprise a light chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:44 and depicted in FIG. 21 (VK variant 2).

A subject anti-C1s antibody can comprise a light chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:45 and depicted in FIG. 22 (VK variant 3).

A subject anti-C1s antibody can comprise a heavy chain variable region comprising 1, 2, 3, 4, 5, 6, 7, 8, 9, 10, 11, or 12 of the framework (FR) amino acid substitutions, relative to the IPN003 parental antibody FR amino acid sequences, depicted in Table 7 (FIG. 23).

For example, a subject anti-C1s antibody can comprise a heavy chain variable region comprising an M→Q substitution at amino acid position 3 in VH FR1 and/or an A→G substitution at amino acid position 10 in VH FR1 and/or a K→R substitution at amino acid position 19 in VH FR1.

As another example, a subject anti-C1s antibody can comprise a heavy chain variable region comprising an I→A substitution at amino acid position 40 in VH FR2 and/or an E→G substitution at amino acid position 42 in VH FR2 and/or an R→G substitution at amino acid position 44 in VH FR2.

As another example, a subject anti-C1s antibody can comprise a heavy chain variable region comprising an A→S substitution at amino acid position 74 in VH FR3 and/or an R→K substitution at amino acid position 75 in VH FR3 and/or a D→N substitution at amino acid position 76 in VH FR3 and/or an S→N amino acid substitution at amino acid position 82A in VH FR3 and/or an S→A amino acid substitution at amino acid position 84 in VH FR3.

As another example, a subject anti-C1s antibody can comprise a heavy chain variable region comprising an S→L, substitution at amino acid position 108 in VH FR4.

A subject anti-C1s antibody can comprise a light chain variable region comprising 1, 2, 3, 4, 5, 6, 7, 8, 9, 10, 11, 12, 13, 14, 15, 16, 17, or 18 of the framework (FR) amino acid substitutions, relative to the IPN003 parental antibody FR amino acid sequence depicted in Table 8 (FIG. 23).

For example, a subject anti-C1s antibody can comprise a light chain variable region comprising an I→T substitution at position 10 in VL FR1 and/or an M→L substitution at amino acid position 11 in VL FR1 and/or an A→L substitution at position 13 of VL FR1 and/or an L→P substitution at position 15 in VL FR1 and/or a V→A substitution at amino acid position 19 in VL FR1 and/or an M→L substitution at amino acid position 21 in VL FR1 and/or a T→S substitution at amino acid position 22 in VL FR1.

As another example, a subject anti-C1s antibody can comprise a light chain variable region comprising an S→K substitution at amino acid position 42 in VL FR2 and/or an S→A substitution at amino acid position 43 in VL FR2.

As another example, a subject anti-C1s antibody can comprise a light chain variable region comprising an A→S substitution at amino acid position 60 in VL FR3 and/or an F→D substitution at amino acid position 70 in VL FR3 and/or an S→T substitution at amino acid position 72 in VL FR3 and/or an M→L substitution at amino acid position 78 in VL FR3 and/or an E→Q substitution at amino acid position 79 in VL FR3 and/or an A→P substitution at amino acid position 80 in VL FR3 and/or a D→F substitution at amino acid position 83 in VL FR3.

As another example, a subject anti-C1s antibody can comprise a light chain variable region comprising an A→Q substitution at amino acid position 100 in VL FR4 and/or an L→I substitution at amino acid position 106 in VL FR4.

In some cases, an anti-C1s antibody of the present disclosure comprises:

i) a VH variant 1 comprising the amino acid sequence depicted in FIG. 16 and set forth in SEQ ID NO:39; and a Vk variant 1 comprising the amino acid sequence depicted in FIG. 20 and set forth in SEQ ID NO:43;

ii) a VH variant 1 comprising the amino acid sequence depicted in FIG. 16 and set forth in SEQ ID NO:39; and a Vk variant 2 comprising the amino acid sequence depicted in FIG. 21 and set forth in SEQ ID NO:44;

iii) a VH variant 1 comprising the amino acid sequence depicted in FIG. 16 and set forth in SEQ ID NO:39; and a Vk variant 3 comprising the amino acid sequence depicted in FIG. 22 and set forth in SEQ ID NO:45;

iv) a VH variant 2 comprising the amino acid sequence depicted in FIG. 17 and set forth in SEQ ID NO:40; and a Vk variant 1 comprising the amino acid sequence depicted in FIG. 20 and set forth in SEQ ID NO:43;

v) a VH variant 2 comprising the amino acid sequence depicted in FIG. 17 and set forth in SEQ ID NO:40; and a Vk variant 2 comprising the amino acid sequence depicted in FIG. 21 and set forth in SEQ ID NO:44;

vi) a VH variant 2 comprising the amino acid sequence depicted in FIG. 17 and set forth in SEQ ID NO:40; and a Vk variant 3 comprising the amino acid sequence depicted in FIG. 22 and set forth in SEQ ID NO:45;

vii) a VH variant 3 comprising the amino acid sequence depicted in FIG. 18 and set forth in SEQ ID NO:41; and a Vk variant 1 comprising the amino acid sequence depicted in FIG. 20 and set forth in SEQ ID NO:43;

viii) a VH variant 3 comprising the amino acid sequence depicted in FIG. 18 and set forth in SEQ ID NO:41; and a Vk variant 2 comprising the amino acid sequence depicted in FIG. 21 and set forth in SEQ ID NO:44;

ix) a VH variant 3 comprising the amino acid sequence depicted in FIG. 18 and set forth in SEQ ID NO:41; and a Vk variant 3 comprising the amino acid sequence depicted in FIG. 22 and set forth in SEQ ID NO:45;

x) a VH variant 4 comprising the amino acid sequence depicted in FIG. 19 and set forth in SEQ ID NO:42; and a Vk variant 1 comprising the amino acid sequence depicted in FIG. 20 and set forth in SEQ ID NO:43;

xi) a VH variant 4 comprising the amino acid sequence depicted in FIG. 19 and set forth in SEQ ID NO:42; and a Vk variant 2 comprising the amino acid sequence depicted in FIG. 21 and set forth in SEQ ID NO:44; or xii) a VH variant 4 comprising the amino acid sequence depicted in FIG. 19 and set forth in SEQ ID NO:42; and a Vk variant 3 comprising the amino acid sequence depicted in FIG. 22 and set forth in SEQ ID NO:45.

In some embodiments, an anti-C1s antibody of the present disclosure is an Ig monomer or an antigen-binding fragment thereof that binds a complement C1s protein. In some embodiments, an anti-C1s antibody of the present disclosure is an Ig monomer. In some embodiments, an anti-C1s antibody of the present disclosure is an antigen-binding fragment of an Ig monomer that binds a complement C1s protein.

In some embodiments, an anti-C1s antibody of the present disclosure is selected from the group consisting of an Ig monomer, a Fab fragment, a F(ab')$_2$ fragment, a Fd fragment, a scFv, a scAb, a dAb, a Fv, a single domain heavy chain antibody, and a single domain light chain antibody.

In some embodiments, an anti-C1s antibody of the present disclosure is selected the group consisting of a mono-specific antibody, a bi-specific antibody, and a multi-specific antibody.

In some embodiments, an anti-C1s antibody of the present disclosure comprises a light chain region and a heavy chain region that are present in separate polypeptides.

In some embodiments, an anti-C1s antibody of the present disclosure comprises a light chain region and a heavy chain region that are present in a single polypeptide.

In some embodiments, a subject antibody comprises anti-C1s heavy chain CDRs and anti-C1s light chain CDRs in a single polypeptide chain, e.g., in some embodiments, a subject antibody is a scFv.

In some embodiments, a subject antibody comprises, in order from N-terminus to C-terminus: a first amino acid sequence of from about 5 amino acids to about 25 amino acids in length; a CDR-L1; a second amino acid sequence of from about 5 amino acids to about 25 amino acids in length; a CDR-L2; a third amino acid sequence of from about 5 amino acids to about 25 amino acids in length; a CDR-L3; a fourth amino acid sequence of from about 5 amino acids to about 25 amino acids in length; a CDR-H1; a fifth amino acid sequence of from about 5 amino acids to about 25 amino acids in length; a CDR-H2; a sixth amino acid sequence of from about 5 amino acids to about 25 amino acids in length; a CDR-H3; and a seventh amino acid sequence of from about 5 amino acids to about 25 amino acids in length. In some embodiments, the respective amino acid sequences of CDR-L1, CDR-L2, CDR-L3, CDR-H1, CDR-H2, and CDR-H3 are: SEQ ID NO:32, SEQ ID NO:33, SEQ ID NO:3, SEQ ID NO:34, SEQ ID NO:35, and SEQ ID NO:36. For example, in some embodiments, a subject antibody comprises, in order from N-terminus to C-terminus: a first amino acid sequence of from about 5 amino acids to about 25 amino acids in length; a CDR-L1 comprising the amino acid sequence set forth in SEQ ID NO:32; a second amino acid sequence of from about 5 amino acids to about 25 amino acids in length; a CDR-L2 comprising the amino acid sequence set forth in SEQ ID NO:33; a third amino acid sequence of from about 5 amino acids to about 25 amino acids in length; a CDR-L3 comprising the amino acid sequence set forth in SEQ ID NO:3; a fourth amino acid sequence of from about 5 amino acids to about 25 amino acids in length; a CDR-H1 comprising the amino acid sequence set forth in SEQ ID NO:34; a fifth amino acid sequence of from about 5 amino acids to about 25 amino acids in length; a CDR-H2 comprising the amino acid sequence set forth in SEQ ID NO:35; a sixth amino acid sequence of from about 5 amino acids to about 25 amino acids in length; a CDR-H3 comprising the amino acid sequence set forth in SEQ ID NO:36; and a seventh amino acid sequence of from about 5 amino acids to about 25 amino acids in length.

In some embodiments, a subject antibody comprises, in order from N-terminus to C-terminus: a light chain FR1 region; a CDR-L1; a light chain FR2 region; a CDR-L2; a light chain FR3 region; a CDR-L3; optionally a light chain FR4 region; a linker region; optionally a heavy chain FR1 region; a CDR-H1; a heavy chain FR2 region; a CDR-H2; a heavy chain FR3 region; a CDR-H3; and a heavy chain FR4 region. In some embodiments, the respective amino acid sequences of CDR-L1, CDR-L2, CDR-L3, CDR-H1, CDR-H2, and CDR-H3 are: SEQ ID NO:32, SEQ ID NO:33, SEQ ID NO:3, SEQ ID NO:34, SEQ ID NO:35, and SEQ ID NO:36. In some of these embodiments, one or more of the FR regions is a humanized FR region. In some of these embodiments, each of the FR regions is a humanized FR region. The linker region can be from about 5 amino acids (aa) to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a first amino acid sequence of from about 5 amino acids to about 25 amino acids in length; a CDR-H1; a second amino acid sequence of from about 5 amino acids to about 25 amino acids in length; a CDR-H2; a third amino acid sequence of from about 5 amino acids to about 25 amino acids in length; a CDR-H3; a fourth amino acid sequence of from about 5 amino acids to about 25 amino acids in length; a CDR-L1; a fifth amino acid sequence of from about 5 amino acids to about 25 amino acids in length; a CDR-L2; a sixth amino acid sequence of from about 5 amino acids to about 25 amino acids in length; a CDR-L3; and a seventh amino acid sequence of from about 5 amino acids to about 25 amino acids in length. In some embodiments, the respective amino acid sequences of CDR-L1, CDR-L2, CDR-L3, CDR-H1, CDR-H2, and CDR-H3 are: SEQ ID NO:32, SEQ ID NO:33, SEQ ID NO:3, SEQ ID NO:34, SEQ ID NO:35, and SEQ ID NO:36. For example, in some embodiments, a subject antibody comprises, in order from N-terminus to C-terminus: a first amino acid sequence of from about 5 amino acids to about 25 amino acids in length; a CDR-H1 comprising the amino acid sequence set forth in SEQ ID NO:34; a second amino acid sequence of from about 5 amino acids to about 25 amino acids in length; a CDR-H2 comprising the amino acid sequence set forth in SEQ ID NO:35; a third amino acid sequence of from about 5 amino acids to about 25 amino acids in length; a CDR-H3 comprising the amino acid sequence set forth in SEQ ID NO:36; a fourth amino acid sequence of from about 5 amino acids to about 25 amino acids in length; a CDR-L1 comprising the amino acid sequence set forth in SEQ ID NO:32; a fifth amino acid sequence of from about 5 amino acids to about 25 amino acids in length; a CDR-L2 comprising the amino acid sequence set forth in SEQ ID NO:33; a sixth amino acid sequence of from about 5 amino acids to about 25 amino acids in length; a CDR-L3 comprising the amino acid sequence set forth in SEQ ID NO:3; and a seventh amino acid sequence of from about 5 amino acids to about 25 amino acids in length.

In some embodiments, a subject antibody comprises, in order from N-terminus to C-terminus: a heavy chain FR1 region; a CDR-H1; a heavy chain FR2 region; a CDR-H2; a heavy chain FR3 region; a CDR-H3; optionally a heavy chain FR4 region; a linker; optionally a light chain FR1 region; a CDR-L1; a light chain FR2 region; a CDR-L2; a light chain FR3 region; a CDR-L3; and a light chain FR4 region. In some embodiments, the respective amino acid sequences of CDR-L1, CDR-L2, CDR-L3, CDR-H1, CDR-H2, and CDR-H3 are: SEQ ID NO:1, SEQ ID NO:2, SEQ ID NO:3, SEQ ID NO:34, SEQ ID NO:35, and SEQ ID NO:36. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a first amino acid sequence of from about 5 amino acids to about 25 amino acids in length; a CDR-L1; a second amino acid sequence of from about 5 amino acids to about 25 amino acids in length; a CDR-L2; a third amino acid sequence of from about 5 amino acids to about 25 amino acids in length; a CDR-L3; a fourth amino acid sequence of from about 5 amino acids to about 25 amino acids in length; a CDR-H1; a fifth amino acid sequence of from about 5 amino acids to about 25 amino acids in length; a CDR-H2; a sixth amino acid sequence of from about 5 amino acids to about 25 amino acids in length; a CDR-H3; and a seventh amino acid sequence of from about 5 amino acids to about 25 amino acids in length. In some embodiments, the respective amino acid sequences of CDR-L1, CDR-L2, CDR-L3, CDR-H1, CDR-H2, and CDR-H3 are: SEQ ID NO:1, SEQ ID NO:2, SEQ ID NO:3, SEQ ID NO:4, SEQ ID NO:5, and SEQ ID NO:6. For example, in some embodiments, a subject antibody comprises, in order from N-terminus to C-terminus: a first amino acid sequence of from about 5 amino acids to about 25 amino acids in length; a CDR-L1 comprising the amino acid sequence set forth in SEQ ID NO:1; a second amino acid sequence of from about 5 amino acids to about 25 amino acids in length; a CDR-L2 comprising the amino acid sequence set forth in SEQ ID NO:2; a third amino acid sequence of from about 5 amino acids to about 25 amino acids in length; a CDR-L3 comprising the amino acid sequence set forth in SEQ ID NO:3; a fourth amino acid sequence of from about 5 amino acids to about 25 amino acids in length; a CDR-H1 comprising the amino acid sequence set forth in SEQ ID NO:4; a fifth amino acid sequence of from about 5 amino acids to about 25 amino acids in length; a CDR-H2 comprising the amino acid sequence set forth in SEQ ID NO:5; a sixth amino acid sequence of from about 5 amino acids to about 25 amino acids in length; a CDR-H3 comprising the amino acid sequence set forth in SEQ ID NO:6; and a seventh amino acid sequence of from about 5 amino acids to about 25 amino acids in length.

In some embodiments, a subject antibody comprises, in order from N-terminus to C-terminus: a light chain FR1 region; a CDR-L1; a light chain FR2 region; a CDR-L2; a light chain FR3 region; a CDR-L3; optionally a light chain FR4 region; a linker region; optionally a heavy chain FR1 region; a CDR-H1; a heavy chain FR2 region; a CDR-H2; a heavy chain FR3 region; a CDR-H3; and a heavy chain FR4 region. In some embodiments, the respective amino acid sequences of CDR-L1, CDR-L2, CDR-L3, CDR-H1, CDR-H2, and CDR-H3 are: SEQ ID NO:1, SEQ ID NO:2, SEQ ID NO:3, SEQ ID NO:4, SEQ ID NO:5, and SEQ ID NO:6. In some of these embodiments, one or more of the FR regions is a humanized FR region. In some of these embodiments, each of the FR regions is a humanized FR region. The linker region can be from about 5 amino acids (aa) to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a first amino acid sequence of from about 5 amino acids to about 25 amino acids in length; a CDR-H1; a second amino acid sequence of from about 5 amino acids to about 25 amino acids in length; a CDR-H2; a third amino acid sequence of from about 5 amino acids to about 25 amino acids in length; a CDR-H3; a fourth amino acid sequence of from about 5 amino acids to about 25 amino acids in length; a CDR-L1; a fifth amino acid sequence of from about 5 amino acids to about 25 amino acids in length; a CDR-L2; a sixth amino acid sequence of from about 5 amino acids to about 25 amino acids in length; a CDR-L3; and a seventh amino acid sequence of from about 5 amino acids to about 25 amino acids in length. In some embodiments, the respective amino acid sequences of CDR-L1, CDR-L2, CDR-L3, CDR-H1, CDR-H2, and CDR-H3 are: SEQ ID NO:1, SEQ ID NO:2, SEQ ID NO:3, SEQ ID NO:4, SEQ ID NO:5, and SEQ ID NO:6. For example, in some embodiments, a subject antibody comprises, in order from N-terminus to C-terminus: a first amino acid sequence of from about 5 amino acids to about 25 amino acids in length; a CDR-H1 comprising the amino acid sequence set forth in SEQ ID NO:4; a second amino acid sequence of from about 5 amino acids to about 25 amino acids in length; a CDR-H2 comprising the amino acid sequence set forth in SEQ ID NO:5; a third amino acid sequence of from about 5 amino acids to about 25 amino acids in length; a CDR-H3 comprising the amino acid sequence set forth in SEQ ID NO:6; a fourth amino acid sequence of from about 5 amino acids to about 25 amino acids in length; a CDR-L1 comprising the amino acid sequence set forth in SEQ ID NO:1; a fifth amino acid sequence of from about 5 amino acids to about 25 amino acids in length; a CDR-L2 comprising the amino acid sequence set forth in SEQ ID NO:2; a sixth amino acid sequence of from about 5 amino acids to about 25 amino acids in length; a CDR-L3 comprising the amino acid sequence set forth in SEQ ID NO:3; and a seventh amino acid sequence of from about 5 amino acids to about 25 amino acids in length.

In some embodiments, a subject antibody comprises, in order from N-terminus to C-terminus: a heavy chain FR1 region; a CDR-H1; a heavy chain FR2 region; a CDR-H2; a heavy chain FR3 region; a CDR-H3; optionally a heavy chain FR4 region; a linker; optionally a light chain FR1 region; a CDR-L1; a light chain FR2 region; a CDR-L2; a light chain FR3 region; a CDR-L3; and a light chain FR4 region. In some embodiments, the respective amino acid sequences of CDR-L1, CDR-L2, CDR-L3, CDR-H1, CDR-H2, and CDR-H3 are: SEQ ID NO:1, SEQ ID NO:2, SEQ ID NO:3, SEQ ID NO:4, SEQ ID NO:5, and SEQ ID NO:6. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

Linkers suitable for use a subject antibody include "flexible linkers". If present, the linker molecules are generally of sufficient length to permit some flexible movement between linked regions. In some embodiments, the linker molecules are generally about 6-50 atoms long. The linker molecules can also be, for example, aryl acetylene, ethylene glycol oligomers containing 2-10 monomer units, diamines, diacids, amino acids, or combinations thereof. Other linker molecules that can bind polypeptides can be used in light of this disclosure.

Suitable linkers can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ (SEQ ID NO:10) and $(GGGS)_n$ (SEQ ID NO:11), where n is an integer of at least one), glycine-alanine polymers, alanine-serine polymers, and other flexible linkers known in the art. Glycine and glycine-serine polymers are of interest since both of these amino acids are relatively unstructured, and therefore can serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited GGSG (SEQ ID NO:12), GGSGG (SEQ ID NO:13), GSGSG (SEQ ID NO:14), GSGGG (SEQ ID NO:15), GGGSG (SEQ ID NO:16), GSSSG (SEQ ID NO:17), and the like. The ordinarily skilled artisan will recognize that design of a peptide conjugated to any elements described above can include linkers that are all or partially flexible, such that the linker can include a flexible linker as well as one or more portions that confer less flexible structure.

In some embodiments, an anti-C1s antibody of the present disclosure comprises scFv multimers. For example, in some embodiments, a subject antibody is an scFv dimer (e.g., comprises two tandem scFv (scFv$_2$)), an scFv trimer (e.g., comprises three tandem scFv (scFv$_3$)), an scFv tetramer (e.g., comprises four tandem scFv (scFv$_4$)), or is a multimer of more than four scFv (e.g., in tandem). The scFv monomers can be linked in tandem via linkers of from about 2 amino acids to about 10 amino acids (aa) in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFv multimer is humanized, as described above.

In some cases, a subject antibody comprises a constant region of an immunoglobulin (e.g., an Fc region). The Fc region, if present, can be a human Fc region or an Fc region from any animal that has a complement system. In some embodiments, the Fc region, if present, is a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Another example of a suitable heavy chain Fc region is a human isotype IgG2 Fc. Yet another example of a suitable heavy chain Fc region is a human isotype IgG3 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab', F(ab')$_2$, and Fv, or as single chain antibodies in which heavy and light chain variable domains are linked through a spacer.

In some cases, the heavy chain region is of the isotype IgG4. In some of these embodiments, the hinge region comprises an S241P substitution. See, e.g., Angal et al. (1993) Mol. Immunol. 30:105. In some of these embodiments, the hinge region comprises an L236E (or L235E, using EU numbering; Kabat et al. (1991) Sequences of Proteins of Immunological Interest, 5$^{th}$ Ed. U.S. Dept. Health and Human Services, Bethesda, Md., NIH Publication No. 91-3242) substitution. See, e.g., Reddy et al. (2000) J. Immunol. 164:1925; and Klechevsky et al. (2010) Blood 116:1685. In some of these embodiments, the hinge region comprises an S241P substitution and an L236E substitution.

A subject antibody can comprise a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to the antibody, where the antibody comprises a non-naturally encoded amino acid that comprises an aminooxy, hydrazine, hydrazide or semiexample ecarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrrolysine or selenocysteine. Other terms that can be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50,000 Da, e.g., from 5,000 Da to 40,000 Da, or from 25,000 to 40,000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a non-peptide synthetic polymer. In some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and can be found in, e.g., U.S. Pat. No. 5,849,860. PEG suitable for conjugation to a protein is generally soluble in water at room temperature, and has the general formula $R(O-CH_2-CH_2)_nO-R$, where R is hydrogen or a protective group such as an alkyl or an alkanol group, and where n is an integer from 1 to 1,000. Where R is a protective group, it generally has from 1 to 8 carbons.

In some embodiments, the PEG conjugated to the subject antibody is linear. In some embodiments, the PEG conjugated to the subject antibody is branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., a subject antibody can comprise a covalently linked carbohydrate or polysaccharide moiety. Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine can also be used.

Addition of glycosylation sites to an antibody is conveniently accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S.

Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers include bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-diphenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2): 209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

In some embodiments, a subject antibody is conjugated to a therapeutic. Any of the subject antibodies disclosed herein can be used to form an antibody-agent conjugate. The agent can be attached to the N terminus of the light chain, the C terminus of the light chain, the N terminus of the heavy chain, or the C terminus of the heavy chain. In some embodiments, the agent is attached to the hinge of the antibody or to one or more other sites on the antibody. For a single chain antibody, the agent can be attached to the N or C terminus of the single chain antibody. The agent can be conjugated to the antibody directly or via a linker using techniques known to those skilled in the art. The linker can be cleavable or non-cleavable. Examples of such therapeutic agents (e.g., for use in therapy) are known to those skilled in the art.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., YPYDVPDYA; SEQ ID NO:18), FLAG (e.g., DYKDDDDK; SEQ ID NO:19), c-myc (e.g., EQKLISEEDL; SEQ ID NO:20), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion can also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:21), His X6 (HHHHHH) (SEQ ID NO:22), c-myc (EQKLISEEDL) (SEQ ID NO:20), Flag (DYKDDDDK) (SEQ ID NO:19), StrepTag (WSHPQFEK) (SEQ ID NO:23), hemagglutinin, e.g., HA Tag (YPYDVPDYA; SEQ ID NO:18), glutathinone-S-transferase (GST), thioredoxin, cellulose binding domain, RYIRS (SEQ ID NO:24), Phe-His-His-Thr (SEQ ID NO:25), chitin binding domain, S-peptide, T7 peptide, SH2 domain, C-end RNA tag, WEAAAREACCRECCARA (SEQ ID NO:26), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

In some embodiments, an anti-C1s antibody of the present disclosure is formulated with an agent that facilitates crossing the blood-brain barrier (BBB). In some embodiments, the antibody is fused, directly or through a linker, to a compound that promotes the crossing of the BBB. Examples of such a compound include, but are not limited to, a carrier molecule, a peptide, or a protein. A subject antibody will in some embodiments be fused to a polypeptide that binds an endogenous BBB receptor. Linking a subject antibody to a polypeptide that binds an endogenous BBB receptor facilitates crossing the BBB, e.g., in a subject treatment method (see below) involving administration of a subject antibody to an individual in need thereof. Suitable polypeptides that bind an endogenous BBB receptor include antibodies, e.g., monoclonal antibodies, or antigen-binding fragments thereof, that specifically bind an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

As an example, a subject anti-C1s antibody can be a bi-specific antibody comprising a first antigen-binding portion that specifically binds an epitope in a complement C1s protein; and a second antigen-binding portion that binds an endogenous BBB receptor. For example, in some instances, a subject anti-C1s antibody is a bi-specific antibody comprising a first antigen-binding portion that specifically binds an epitope in a C1s protein; and a second antigen-binding portion that binds a transferrin receptor.

For example, an anti-C1s antibody of the present disclosure can be fused to a peptide that facilitates crossing the BBB, the peptide having a length of from about 15 amino acids to about 25 amino acids, and comprising an amino acid sequence that is at least about 85% amino acid sequence identical to one of the following peptides: Angiopep-1 (TFFYGGCRGKRNNFKTEEY) (SEQ ID NO:27); Angiopep-2 (TFFYGGSRGKRNNFKTEEY) (SEQ ID NO:28); cys-Angiopep-2 (CTFFYGGSRGKRNNFKTEEY) (SEQ ID NO:29); Angiopep-2-cys (TFFYGGSRGKRNNFKTEEYC) (SEQ ID NO:30); and an aprotinin fragment (TFVYGGCRAKRNNFKS) (SEQ ID NO:31). See, e.g., U.S. Patent Publication Nos. 2011/0288011; and 2009/0016959. A peptide that facilitates crossing the BBB can be fused to the N-terminus of an anti-C1s light chain region, to the C-terminus of an anti-C1s light chain region, to the N-terminus of an anti-C1s heavy chain region, to the C-terminus of an anti-C1s heavy chain region, to the N-terminus of a subject anti-C1s single-chain antibody, to the C-terminus of a subject anti-C1s single-chain antibody, etc.

In some embodiments, a subject antibody comprises a polyamine modification. Polyamine modification of a subject antibody enhances permeability of the modified antibody at the BBB. A subject antibody can be modified with polyamines that are either naturally occurring or synthetic. See, for example, U.S. Pat. No. 5,670,477. Useful naturally occurring polyamines include putrescine, spermidine, spermine, 1,3-diaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or $N(R)_2$ moieties, wherein R is H, $(C_1-C_4)$ alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated (e.g., encapsulated) into a liposome.

Methods of Producing a Subject Antibody

A subject antibody can be produced by any known method, e.g., conventional synthetic methods for protein synthesis; recombinant DNA methods; etc. In some embodiments, the subject antibody is produced by a method selected from the group consisting of recombinant production and chemical synthesis.

Where a subject antibody is a single chain polypeptide, it can be synthesized using standard chemical peptide synthesis techniques. Where a polypeptide is chemically synthesized, the synthesis can proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med Chem.* 6:3-10 and Camarero J A et al. 2005 *Protein Pept Lett.* 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid can be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, repressor elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce an anti-C1s antibody of the present disclosure (e.g., polynucleotides encoding a subject anti-C1s antibody). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148:1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acid Molecules, Expression Vectors, and Host Cells

The present disclosure provides nucleic acid molecules comprising nucleotide sequences encoding a subject anti-C1s antibody.

In some embodiments, a nucleic acid molecule of the present disclosure encodes a subject anti-C1s antibody comprising a light chain variable region that is at least 85%, 86%, 87%, 88%, 89%, 90%, 91%, 92%, 93%, 94%, 95%, 96%, 97%, 98% or 99% amino acid sequence identical to the amino acid sequence set forth in SEQ ID NO:7. In some embodiments, a nucleic acid molecule of the present disclosure encodes a subject anti-C1s antibody comprising a light chain variable region comprising the amino acid sequence set forth in SEQ ID NO:7.

In some embodiments, a nucleic acid molecule of the present disclosure encodes a subject anti-C1s antibody comprising a heavy chain variable region that is at least 85%, 86%, 87%, 88%, 89%, 90%, 91%, 92%, 93%, 94%, 95%, 96%, 97%, 98% or 99% amino acid sequence identical to the amino acid sequence set forth in SEQ ID NO:8. In some embodiments, a nucleic acid molecule of the present disclosure encodes a subject anti-C1s antibody comprising a heavy chain variable region comprising the amino acid sequence set forth in SEQ ID NO:8.

In some embodiments, a nucleic acid molecule of the present disclosure encodes a subject anti-C1s antibody comprising a light chain variable region comprising a CDR-L1, a CDR-L2, and a CDR-L3 of SEQ ID NO:1, SEQ ID NO:2, and SEQ ID NO:3, respectively.

In some embodiments, a nucleic acid molecule of the present disclosure encodes a subject anti-C1s antibody comprising a heavy chain variable region comprising a CDR-H1, a CDR-H2, and a CDR-H3 of SEQ ID NO:4, SEQ ID NO:5, and SEQ ID NO:6, respectively.

In some embodiments, a nucleic acid molecule of the present disclosure encodes a subject anti-C1s antibody comprising a light chain variable region that is at least 85%, 86%, 87%, 88%, 89%, 90%, 91%, 92%, 93%, 94%, 95%, 96%, 97%, 98% or 99% amino acid sequence identical to the amino acid sequence set forth in SEQ ID NO:37. In some embodiments, a nucleic acid molecule of the present disclosure encodes a subject anti-C1s antibody comprising a light chain variable region comprising the amino acid sequence set forth in SEQ ID NO:37.

In some embodiments, a nucleic acid molecule of the present disclosure encodes a subject anti-C1s antibody comprising a heavy chain variable region that is at least 85%, 86%, 87%, 88%, 89%, 90%, 91%, 92%, 93%, 94%, 95%, 96%, 97%, 98% or 99% amino acid sequence identical to the amino acid sequence set forth in SEQ ID NO:38. In some embodiments, a nucleic acid molecule of the present disclosure encodes a subject anti-C1s antibody comprising a heavy chain variable region comprising the amino acid sequence set forth in SEQ ID NO:38.

In some embodiments, a nucleic acid molecule of the present disclosure encodes a subject anti-C1s antibody comprising a light chain variable region comprising a CDR-L1, a CDR-L2, and a CDR-L3 of SEQ ID NO:32, SEQ ID NO:33, and SEQ ID NO:3, respectively.

In some embodiments, a nucleic acid molecule of the present disclosure encodes a subject anti-C1s antibody comprising a heavy chain variable region comprising a CDR-H1, a CDR-H2, and a CDR-H3 of SEQ ID NO:34, SEQ ID NO:35, and SEQ ID NO:36, respectively.

In some embodiments, a nucleic acid molecule of the present disclosure encodes a subject anti-C1s antibody comprising a light chain variable region and a heavy chain variable region.

A nucleic acid molecule encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. Suitable promoters for use in prokaryotic host cells include, but are not limited to, a bacteriophage T7 RNA polymerase promoter; a T3 promoter; a T5 promoter; a lambda P promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; a gpt promoter; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein—Nucleic Acid Interaction.* Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding the operator), a tryptophan promoter operator (when complexed with tryptophan, TrpR repressor protein has a conformation that binds the operator; in the absence of tryptophan, the TrpR repressor protein has a conformation that does not bind the operator), and a tac promoter operator (see, for example, deBoer et al. (1983) Proc. Natl. Acad. Sci. U.S.A. 80:21-25).

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*).

For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Selection of the appropriate vector and promoter is well within the level of ordinary skill in the art.

A nucleic acid molecule encoding a subject antibody can be present in an expression vector and/or a cloning vector. The present disclosure provides a recombinant vector, which comprises a nucleic acid molecule encoding a subject antibody in a cloning vector. The present disclosure also provides a recombinant molecule, which comprises a nucleic acid molecule encoding a subject antibody operatively linked to appropriate regulatory sequence(s) in an expression vector to ensure expression of the encoded antibody. Where a subject antibody comprises two separate polypeptides, nucleic acid molecules encoding the two polypeptides can be cloned in the same or separate vectors to form one or more recombinant molecules. A recombinant molecule can include a selectable marker, an origin of replication, and other features that provide for replication and/or maintenance of the recombinant molecule.

Large numbers of suitable vectors and promoters are known to those of skill in the art; many are commercially available for generating a subject recombinant molecule. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host can be present. Suitable expression vectors include, but are not limited to, viral vectors. Examples of viral vectors include, but are not limited to, viral vectors based on: vaccinia virus; poliovirus; adenovirus (see, e.g., Li et al., Invest Opthalmol V is Sci 35:2543 2549, 1994; Borras et al., Gene Ther 6:515 524, 1999; L1 and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol V is Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus (see, e.g., Miyoshi et al., PNAS 94:10319 23, 1997; Takahashi et al., J Virol 73:7812 7816, 1999), myeloproliferative sarcoma virus, and mammary tumor virus); and the like.

As noted above, a subject nucleic acid molecule comprises a nucleotide sequence encoding an anti-C1s antibody of the present disclosure. In some embodiments, a subject nucleic acid molecule comprises a nucleotide sequence encoding heavy- and light-chain CDRs of a subject IPN003 antibody. In some embodiments, a subject nucleic acid molecule comprises a nucleotide sequence encoding heavy- and light-chain CDRs of a subject antibody, where the CDR-encoding sequences are interspersed with FR-encoding nucleotide sequences. In some embodiments, the FR-encoding nucleotide sequences are human FR-encoding nucleotide sequences.

Host Cells

The present disclosure provides isolated genetically modified host cells (e.g., in vitro cells) that are genetically modified with a subject nucleic acid molecule. In some embodiments, a subject isolated genetically modified host cell can produce a subject antibody. Such a cell is referred to as a recombinant cell. A recombinant cell comprises a recombinant molecule encoding a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. In some cases, the cells are HEK cells. In some cases, the cells are CHO cells, e.g., CHO-K1 cells (ATCC No. CCL-61), CHO-M cells, CHO-DG44 cells (ATCC No. PTA-3356), and the like. In some embodiments, the host cell is a COS cell. In some embodiments, the host cell is a 293 cell. In some embodiments, the host cell is a CHO cell.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia ptjperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a *Saccharomyces*. In some embodiments, the host cell is a *Pichia*.

Suitable prokaryotic cells include, but are not limited to, any of a variety of laboratory strains of *Escherichia coli, Bacillus* (e.g., *B. subtilis*), *Lactobacillus* sp., and the like. See, e.g., Carrier et al. (1992) *J. Immunol.* 148:1176-1181; U.S. Pat. No. 6,447,784; and Sizemore et al. (1995) *Science* 270: 299-302. Typically, the laboratory strain is one that is non-pathogenic. In some embodiments, the host cell is *Escherichia coli*. In some embodiments, the host cell is *Bacillus subtilis*.

Pharmaceutical Compositions

The present disclosure provides compositions, including pharmaceutical compositions comprising a subject antibody. In general, a pharmaceutical composition, also referred to herein as a formulation, comprises an effective amount of a subject antibody. An "effective amount" means a dosage sufficient to produce a desired result, e.g., reduction in an adverse symptom associated with a complement-mediated disease or disorder, amelioration of a symptom of a complement-mediated disease or disorder, slowing progression of a complement-mediated disease or disorder, etc. Generally, the desired result is at least a reduction in a symptom of a complement-mediated disease or disorder, as compared to a control. In some embodiments, a subject antibody is formulated and/or modified to enable the antibody to cross the blood-brain barrier. In some embodiments, a subject antibody is delivered in such a manner as to avoid the blood-brain barrier. In some embodiments, an anti-C1s antibody of the present disclosure is formulated with an agent that facilitates crossing the blood-brain barrier. In some embodiments, the subject antibody is fused, directly or through a linker, to a compound that promotes the crossing of the blood-brain barrier.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers, pharmaceutically acceptable diluents, or other pharmaceutically acceptable excipients and can be formulated into preparations in solid, semi-solid, liquid or gaseous forms, such as tablets, capsules, powders, granules, ointments, solutions, suppositories, injections, inhalants and aerosols. In some embodiments, a pharmaceutical composition comprises a subject antibody and a pharmaceutically acceptable excipient.

In pharmaceutical dosage forms, a subject antibody can be administered in the form of their pharmaceutically acceptable salts, or they can also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying the antibody in an aqueous or nonaqueous solvent, such as vegetable or other similar oils, propylene glycol, synthetic aliphatic acid glycerides, injectable organic esters (e.g., ethyl oleate), esters of higher aliphatic acids or propylene glycol; and if desired, with conventional additives such as solubilizers, isotonic agents, suspending agents, emulsifying agents, stabilizers and preservatives. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Furthermore, the pharmaceutical composition of the present disclosure can comprise further agents such as dopamine or psychopharmacologic drugs, depending on the intended use of the pharmaceutical composition.

Pharmaceutical compositions comprising a subject antibody are prepared by mixing a subject antibody having the desired degree of purity with optional physiologically acceptable carriers, other excipients, stabilizers, surfactants, buffers and/or tonicity agents. Acceptable carriers, other excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition can be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents can be used for the production of pharmaceutical compositions for parenteral administration; see also Chen (1992) Drug Dev Ind Pharm 18, 1311-54.

Exemplary antibody concentrations in a subject pharmaceutical composition can range from about 1 mg/mL to about 200 mg/mL or from about 50 mg/mL to about 200 mg/mL, or from about 150 mg/mL to about 200 mg/mL.

An aqueous formulation of the antibody can be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent can be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions can be suitable. The term "isotonic" denotes a solution having the same tonicity as some other solution with which it is compared, such as a physiological salt solution or serum. Tonicity agents can be used in an amount of about 5 mM to about 350 mM, e.g., in an amount of 100 mM to 350 nM.

A surfactant can also be added to the antibody formulation to reduce aggregation of the formulated antibody and/or minimize the formation of particulates in the formulation and/or reduce adsorption. Exemplary surfactants include polyoxyethylenesorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant can range from about 0.001% to about 1% w/v.

A lyoprotectant can also be added in order to protect the labile active ingredient (e.g. a protein) against destabilizing conditions during the lyophilization process. For example, known lyoprotectants include sugars (including glucose and sucrose); polyols (including mannitol, sorbitol and glycerol);

and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM sucrose; and has a pH of 5.5; or 4) 75 mg/mL of a subject antibody; 0.04% Tween 20 w/v; 20 mM L-histidine; and 250 mM trehalose; and has a pH of 5.5; or 5) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.02% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like. Aerosol formulations such as nasal spray formulations include purified aqueous or other solutions of the active agent with preservative agents and isotonic agents. Such formulations are adjusted to a pH and isotonic state compatible with the nasal mucous membranes.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions can be provided wherein each dosage unit, for example, teaspoonful, tablespoonful, tablet or suppository, contains a predetermined amount of the composition. Similarly, unit dosage forms for injection or intravenous administration can comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an anti-C1s antibody of the present disclosure, calculated in an amount sufficient to produce the desired effect in association with a pharmaceutically acceptable diluent, carrier or vehicle. The specifications for a subject antibody can depend on the particular antibody employed and the effect to be achieved, and the pharmacodynamics associated with each antibody in the host.

Other modes of administration will also find use with a method of the present disclosure. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories can be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations can also contain preservatives such as, but not limited to, chlorobutanol and benzalkonium chloride. A surfactant can be present to enhance absorption of the subject antibody by the nasal mucosa.

A subject antibody can be administered as an injectable formulation. Typically, injectable compositions are prepared as liquid solutions or suspensions; solid forms suitable for solution in, or suspension in, liquid vehicles prior to injection can also be prepared. The preparation can also be emulsified or the antibody encapsulated in liposome vehicles.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations can be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations can be prevented by using appropriate additives, by controlling moisture content and by developing specific polymer matrix compositions.

Controlled release within the scope of the present disclosure can be taken to mean any one of a number of extended release dosage forms. The following terms can be considered to be substantially equivalent to controlled release, for the purposes of the present disclosure: continuous release, controlled release, delayed release, depot, extended release, gradual release, immediate release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, and sustained-action medications. Further discussions of these terms can be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release can be found in Agis F. Kydonieus, *Controlled Release Technologies: Methods, Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems can be found in Yie W. Chien, *Novel Drug Delivery Systems*, 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody can be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

In some embodiments, a dose of a subject anti-C1s antibody is in the range of 0.001 µg to 1000 µg; however, doses below or above this exemplary range are envisioned, especially considering the aforementioned factors. In some embodiments, the dosage can range, e.g., from about 0.0001 to 100 mg/kg, or from about 0.01 to 5 mg/kg (e.g., 0.02 mg/kg, 0.25 mg/kg, 0.5 mg/kg, 0.75 mg/kg, 1 mg/kg, 2 mg/kg, etc.) body weight. For example dosages can be 1 mg/kg body weight or 10 mg/kg body weight or within the range of 1-10 mg/kg, or at least 1 mg/kg. Doses intermediate in the above ranges are also intended to be within the scope of the invention.

In some embodiments, a subject anti-C1s antibody is administered in an amount that provides for a peak serum concentration of from about 1 µg/ml to about 1 mg/ml, e.g., from about 1 µg/ml to about 2.5 µg/ml, from about 2.5 µg/ml to about 5 µg/ml, from about 5 µg/ml to about 7.5 µg/ml, from about 7.5 µg/ml to about 10 µg/ml, from about 10 µg/ml to about 25 Kg/ml, from about 25 µg/ml to about 50 µg/ml, from about 50 µg/ml to about 100 µg/ml, from about 100 µg/ml to about 250 µg/ml, from about 250 µg/ml to about 500 µg/ml, from about 500 Kg/ml to about 750 µg/ml, or from about 750 µg/ml to about 1000 µg/ml. In some embodiments, a subject anti-C1s antibody is administered in an amount that provides for a peak serum concentration of greater than 1 mg/ml, e.g., from about 1 mg/ml to about 2 mg/ml, from about 2 mg/ml to about 5 mg/ml, or from about 5 mg/ml to about 10 mg/ml.

Individuals can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment.

Those of skill will readily appreciate that dose levels and administration schedules can vary as a function of the specific antibody, the severity of the symptoms and the susceptibility of the subject to side effects. Preferred dosages and administration schedules for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intrathecal, intracranial, subcutaneous, intradermal, topical, intravenous, intraperitoneal, intraarterial (e.g., via the carotid artery), spinal or brain delivery, rectal, nasal, oral, and other enteral and parenteral routes of administration. Routes of administration can be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously. In some embodiments, a subject antibody composition is administered intrathecally.

An antibody of the present disclosure can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrathecal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a complement-mediated disease or disorder. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection and/or delivery, e.g., to a site in a brain artery or directly into brain tissue. A subject antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., cats), herbivores (e.g., cattle, horses, and sheep), omnivores (e.g., dogs, goats, and pigs), rodentia (e.g., mice, guinea pigs, and rats), and primates (e.g., humans, chimpanzees, and monkeys). In some embodiments, the host is an individual that has a complement system, such as a mammal, fish, or invertebrate. In some embodiments, the host is a complement system-containing mammal, fish, or invertebrate companion animal, agricultural animal, work animal, zoo animal, or lab animal. In some embodiments, the host is human.

The embodiments include compositions comprising a container suitable for containing a composition comprising a subject anti-C1s antibody for administration to an individual. For example, a subject antibody can be disposed within a container suitable for containing a pharmaceutical composition. The container can be, for example, a bottle (e.g., with a closure device, such as a cap), a blister pack (e.g., which can provide for enclosure of one or more doses per blister), a vial, flexible packaging (e.g., sealed Mylar or plastic bags), an ampule (for single doses in solution), a dropper, a syringe, thin film, a tube and the like. In some embodiments, a container, such as a sterile container, comprises a subject pharmaceutical composition. In some embodiments the container is a bottle or a syringe. In some embodiments the container is a bottle. In some embodiments the container is a syringe.

Kits with unit doses of a subject antibody, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Methods of Treating a Complement-Mediated Disease or Disorder

The present disclosure provides methods of treating a complement-mediated disease or disorder. The methods generally involve administering an effective amount of an anti-C1s antibody of the present disclosure, or a pharmaceutical composition comprising such an antibody, to an individual in need thereof. In some cases, administration of a subject anti-C1s antibody modulates the activity of complement C1s in a cell, a tissue, or a fluid of an individual, and treats the complement-mediated disease or disorder. The present disclosure provides methods of inhibiting activation of complement component C4 in an individual, the methods comprising administering to the individual an effective amount of an anti-C1s antibody of the present disclosure or a pharmaceutical composition comprising such an antibody. The present disclosure provides methods of inhibiting complement C1s activity in an individual the methods comprising administering to the individual an effective amount of an anti-C1s antibody of the present disclosure or a pharmaceutical composition comprising such an antibody.

In some embodiments, a method of the present disclosure to treat an individual having a complement-mediated disease or disorder comprises administering to the individual an effective amount of an anti-C1s antibody of the present disclosure or an effective amount of a pharmaceutical composition comprising: a) an anti-C1s antibody of the present disclosure; and a pharmaceutically acceptable excipient suitable for administration to such individual. In some embodiments, the individual is a mammal. In some embodiments, the individual is a human. Administering can be by any route known to those skilled in the art, including those disclosed herein. In some embodiments, administering is intravenous. In some embodiments, administering is intrathecal. In some embodiments, administering is subcutaneous.

In some embodiments, an "effective amount" of an anti-C1s antibody of the present disclosure, or an "effective amount" of a subject pharmaceutical composition comprising an anti-C1s antibody of the present disclosure, is an amount that, when administered in one or more doses to an individual in need thereof, reduces production of C4b2a (i.e., complement C4b and C2a complex; also known as "C3 convertase") in the individual (or in a tissue or organ of the individual) by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C4b2a produced in the individual, or the tissue or organ, in the absence of a subject anti-C1s antibody. In some embodiments, the individual is a mammal. In some embodiments, the individual is a human. Administering can be by any route known to those skilled in the art, including those disclosed herein. In some embodiments, administering is intravenous. In some embodiments, the route of administration is intrathecal. In some embodiments, the route of administration is intravenous. In some embodiments, the route of administration is subcutaneous.

The present disclosure provides a method to modulate complement activation. In some embodiments the method inhibits complement activation, for example to reduce production of C4b2a. In some embodiments, the present disclosure provides a method to modulate complement activation in an individual having a complement-mediated disease or disorder, the method comprising administering to the individual an anti-C1s antibody of the present disclosure or a pharmaceutical composition of the present disclosure, wherein the pharmaceutical composition comprises an anti-C1s antibody of the present disclosure. In some embodiments such a method inhibits complement activation. In some embodiments, the individual is a mammal. In some embodiments, the individual is a human. Administering can be by any route known to those skilled in the art, including those disclosed herein. In some embodiments, administering is intravenous. In some embodiments, administering is intrathecal.

A complement-mediated disease or disorder is a disorder characterized by an abnormal amount of complement C1s or an abnormal level of complement C1s proteolytic activity in a cell, a tissue, or a fluid of an individual.

In some cases, a complement-mediated disease or disorder is characterized by the presence in a cell, a tissue, or a fluid of an elevated (higher than normal) amount of C1s or of an elevated level of complement C1s activity. For example, in some cases, a complement-mediated disease or disorder is characterized by the presence in brain tissue and/or cerebrospinal fluid of an elevated amount and/or an elevated activity of C1s. A "higher than normal" amount of C1s in a cell, a tissue, or a fluid indicates that the amount of C1s in the cell, tissue or fluid is higher than a normal, control level, e.g., higher than a normal, control level for an individual or population of individuals of the same age group. A "higher than normal" level of C1s activity in a cell, a tissue, or a fluid indicates that the proteolytic cleavage effected by C1s in the cell, tissue or fluid is higher than a normal, control level, e.g., higher than a normal, control level for an individual or population of individuals of the same age group. In some cases, an individual having a complement-mediated disease or disorder exhibits one or more additional symptoms of such a disease or disorder.

In other cases, a complement-mediated disease or disorder is characterized by the presence in a cell, a tissue, or a fluid of a lower than normal amount of C1s or of a lower level of complement C1s activity. For example, in some cases, a complement-mediated disease or disorder is characterized by the presence in brain tissue and/or cerebrospinal fluid of a lower amount and/or a lower activity of C1s. A "lower than normal" amount of C1s in a cell, a tissue, or a fluid indicates that the amount of C1s in the cell, tissue or fluid is lower than a normal, control level, e.g., lower than a normal, control level for an individual or population of individuals of the same age group. A "lower than normal" level of C1s activity in a cell, a tissue, or a fluid indicates that the proteolytic cleavage effected by C1s in the cell, tissue or fluid is lower than a normal, control level, e.g., lower than a normal, control level for an individual or population of individuals of the same age group. In some cases, an individual having a complement-mediated disease or disorder exhibits one or more additional symptoms of such a disease or disorder.

A complement-mediated disease or disorder is a disease or disorder in which the amount or activity of complement C1s is such as to cause disease or disorder in an individual. In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In some embodiments, the complement-mediated disease or disorder is an autoimmune disease. In some embodiments, the complement-mediated disease or disorder is cancer. In some embodiments, the complement-mediated disease or disorder is an infectious disease. In some embodiments, the complement-mediated disease or disorder is an inflammatory disease. In some embodiments, the complement-mediated disease or disorder is a hematological disease. In some embodiments, the complement-mediated disease or disorder is an ischemia-reperfusion injury. In some embodiments, the complement-mediated disease or disorder is ocular disease. In some embodiments, the complement-mediated disease or disorder is a renal disease. In some embodiments, the complement-mediated disease or disorder is transplant rejection. In some embodiments, the complement-mediated disease or disorder is antibody-mediated transplant rejection. In some embodiments, the complement-mediated disease or disorder is a vascular disease. In some embodiments, the complement-mediated disease or disorder is a vasculitis disorder. In some embodiments, the complement-mediated disease or disorder is a neurodegenerative disease or disorder. In some embodiments, the complement-mediated disease is a neurodegenerative disease. In some embodiments, the complement-mediated disorder is a neurodegenerative disorder. In some embodiments, the complement-mediated disease or disorder is a tauopathy.

Examples of a complement-mediated disease or disorder include, but are not limited to, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases, Barraquer-Simons syndrome, Behçet's disease, British type amyloid angiopathy, bullous pemphigoid, Buerger's disease, C1q nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barré syndrome, Hallervorden-Spatz disease, hemolytic-uremic syndrome, hereditary angioedema, hypophosphastasis, idiopathic pneumonia syndrome, immune complex diseases, inclusion body myositis, infectious disease (e.g., disease caused by bacterial (e.g., *Neisseria meningitidis* or *Streptococcus*) viral (e.g., human immunodeficiency virus (HIV)), or other infectious agents), inflammatory disease, ischemia/reperfusion injury, mild cognitive impairment, immunothrombocytopenic purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin E coli (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, bullous pemphigoid, *Epidermolysis bullosa acquisita*, delayed hemolytic transfusion reaction, hypocomplementemic urticarial vasculitis syndrome, pseudophakic bullous keratopathy, and platelet refractoriness.

Alzheimer's disease and certain forms of Frontotemporal dementia (Pick's disease, sporadic Frontotemporal dementia and Frontotemporal dementia with Parkinsonism linked to chromosome 17) are the most common forms of tauopathy. In accordance, the present invention relates to any method as described above, wherein the tauopathy is Alzheimer's, Pick's disease, sporadic Frontotemporal dementia and Frontotemporal dementia with Parkinsonism linked to chromosome 17. Other tauopathies include but are not limited to Progressive supranuclear palsy (PSP), Corticobasal degeneration (CBD) and Subacute sclerosing panencephalitis.

A neurodegenerative tauopathy includes Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, ischemic stroke, chronic traumatic encephalopathy (CTE), traumatic brain injury (TBI), and stroke.

The present disclosure also provides methods of treating a synucleinopathy, e.g., Parkinson's disease (PD); dementia with Lewy Bodies (DLB); multiple system atrophy (MSA); etc. For example, PD with dementia (PDD) can be treated with a subject method.

In some embodiments, the complement-mediated disease or disorder comprises Alzheimer's disease. In some embodiments, the complement-mediated disease or disorder comprises Parkinson's disease. In some embodiments, the complement-mediated disease or disorder comprises transplant rejection. In some embodiments, the complement-mediated disease or disorder is antibody-mediated transplant rejection.

In some embodiments, an anti-C1s antibody of the present disclosure prevents or delays the onset of at least one symptom of a complement-mediated disease or disorder in an individual. In some embodiment, an anti-C1s antibody of the present disclosure reduces or eliminates at least one symptom of a complement-mediated disease or disorder in an individual. Examples of symptoms include, but are not limited to, symptoms associated with autoimmune disease, cancer, hematological disease, infectious disease, inflammatory disease, ischemia-reperfusion injury, neurodegenerative disease, neurodegenerative disorder, renal disease, transplant rejection, ocular disease, vascular disease, or a vasculitis disorder. The symptom can be a neurological symptom, for example, impaired cognitive function, memory impairment, loss of motor function, etc. The symptom can also be the activity of C1s protein in a cell, tissue, or fluid of an individual. The symptom can also be the extent of complement activation in a cell, tissue, or fluid of an individual.

In some embodiments, administering an anti-C1s antibody of the present disclosure to an individual modulates complement activation in a cell, tissue, or fluid of an individual. In some embodiments, administration of a subject anti-C1s antibody to an individual inhibits complement activation in a cell, tissue, or fluid of an individual. For example, in some embodiments, a subject anti-C1s antibody, when administered in one or more doses as monotherapy or in combination therapy to an individual having a complement-mediated disease or disorder, inhibits complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the anti-C1s antibody.

In some embodiments, an anti-C1s antibody of the present disclosure reduces C3 deposition onto red blood cells; for example, in some embodiments, an anti-C1s antibody of the present disclosure reduces deposition of C3b, iC3b, etc., onto RBCs). In some embodiments, an anti-C1s antibody of the present disclosure inhibits complement-mediated red blood cell lysis.

In some embodiments, an anti-C1s antibody of the present disclosure reduces C3 deposition onto platelets; for example, in some embodiments, an anti-C1s antibody of the present disclosure reduces deposition of C3b, iC3b, etc., onto platelets).

In some embodiments, administering an anti-C1s antibody of the present disclosure results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition, (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) reduction of demyelination; (ab) reduction of eosinophilia; (ac) a reduction of C3 deposition on red blood cells (e.g., a reduction of deposition of C3b, iC3b, etc., onto RBCs); and (ad) a reduction in C3 deposition on platelets (e.g., a reduction of deposition of C3b, iC3b, etc., onto platelets); and (ae) a reduction of anaphylatoxin toxin production; (af) a reduction in autoantibody mediated blister formation; (ag) a reduction in autoantibody induced pruritis; (ah) a reduction in autoantibody induced erythematosus; (ai) a reduction in autoantibody mediated skin erosion; (aj) a reduction in red blood cell destruction due to transfusion reactions; (ak) a reduction in red blood cell lysis due to alloantibodies; (al) a reduction in hemolysis due to transfusion reactions; (am) a reduction in allo-antibody mediated platelet lysis; (an) a reduction in platelet lysis due to transfusion reactions; (ao) a reduction in mast cell activation; (ap) a reduction in mast cell histamine release; (aq) a reduction in vascular permeability; (ar) a reduction in edema; (as) a reduction in complement deposition on transplant graft endothelium; (at) a reduction of anaphylatoxin generation in transplant graft endothelium; (au) a reduction in the separation of the dermal-epidermal junction; (av) a reduction in the generation of anaphylatoxins in the dermal-epidermal junction; (aw) a reduction in alloantibody mediated complement activation in transplant graft endothelium; (ax) a reduction in antibody mediated loss of the neuromuscular junction; (ay) a reduction in complement activation at the neuromuscular junction; (az) a reduction in anaphylatoxin generation at the neuromuscular junction; (ba) a reduction in complement deposition at the neuromuscular junction; (bb) a reduction in paralysis; (bc) a reduction in numbness; (bd) increased bladder control; (be) increased bowel control; (bf) a reduction in mortality associated with autoantibodies; and (bg) a reduction in morbidity associated with autoantibodies.

In some embodiments, a subject anti-C1s antibody, when administered in one or more doses as monotherapy or in combination therapy to an individual having a complement-mediated disease or disorder, is effect to achieve a reduction of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: (a) complement activation; (b) decline in cognitive function; (c) neuron loss; (d) phospho-Tau levels in neurons; (e) glial cell activation; (f) lymphocyte infiltration; (g) macrophage infiltration; (h) antibody deposition, (i) glial cell loss; (j) oligodendrocyte loss; (k) dendritic cell infiltration; (l) neutrophil infiltration; (m) red blood cell lysis; (n) red blood cell phagocytosis; (o) platelet phagocytosis; (p) platelet lysis; (q) transplant graft rejection; (r) macrophage mediated phagocytosis; (s) vision loss; (t) antibody mediated complement activation; (u) autoantibody mediated complement activation; (v) demyelination; (w) eosinophilia; compared to the level or degree of the outcome in the individual before treatment with the anti-C1s antibody.

In some embodiments, a subject anti-C1s antibody, when administered in one or more doses as monotherapy or in combination therapy to an individual having a complement-mediated disease or disorder, is effect to achieve an improvement of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: a) cognitive function; b) transplant graft survival; c) vision; d) motor control; e) thrombus formation; f) clotting; g) kidney function; and h) hematocrit (red blood cell count), compared to the level or degree of the outcome in the individual before treatment with the anti-C1s antibody.

In some embodiments, administering an anti-C1s antibody of the present disclosure to an individual reduces complement activation in the individual. For example, in some embodiments, a subject anti-C1s antibody, when administered in one or more doses as monotherapy or in combination therapy to an individual having a complement-mediated disease or disorder, reduces complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the anti-C1s antibody.

In some embodiments, administering an anti-C1s antibody of the present disclosure improves cognitive function in the individual. For example, in some embodiments, a subject anti-C1s antibody, when administered in one or more doses as monotherapy or in combination therapy to an individual having a complement-mediated disease or disorder, improves cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the cognitive function in the individual before treatment with the anti-C1s antibody.

In some embodiments, administering an anti-C1s antibody of the present disclosure reduces the rate of decline in cognitive function in the individual. For example, in some embodiments, a subject anti-C1s antibody, when administered in one or more doses as monotherapy or in combination therapy to an individual having a complement-mediated disease or disorder, reduces the rate of decline of cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the rate of decline in cognitive function in the individual before treatment with the anti-C1s antibody.

In some embodiments, administering an anti-C1s antibody of the present disclosure to an individual reduces neuron loss in the individual. For example, in some embodiments, a subject anti-C1s antibody, when administered in one or more doses as monotherapy or in combination therapy to an individual having a complement-mediated disease or disorder, reduces neuron loss in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to neuron loss in the individual before treatment with the anti-C1s antibody.

In some embodiments, administering an anti-C1s antibody of the present disclosure to an individual reduces phospho-Tau levels in the individual. For example, in some embodiments, a subject anti-C1s antibody, when administered in one or more doses as monotherapy or in combination therapy to an individual having a complement-mediated disease or disorder, reduces phospho-Tau in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the phospho-Tau level in the individual before treatment with the anti-C1s antibody.

In some embodiments, administering an anti-C1s antibody of the present disclosure to an individual reduces glial cell activation in the individual. For example, in some embodiments, a subject anti-C1s antibody, when administered in one or more doses as monotherapy or in combination therapy to an individual having a complement-mediated disease or disorder, reduces glial activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to glial cell activation in the individual before treatment with the anti-C1s antibody. In some embodiments, the glial cells are astrocytes or microglia.

In some embodiments, administering an anti-C1s antibody of the present disclosure to an individual reduces lymphocyte infiltration in the individual. For example, in some embodiments, a subject anti-C1s antibody, when administered in one or more doses as monotherapy or in combination therapy to an individual having a complement-mediated disease or disorder, reduces lymphocyte infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to lymphocyte infiltration in the individual before treatment with the anti-C1s antibody.

In some embodiments, administering an anti-C1s antibody of the present disclosure to an individual reduces macrophage infiltration in the individual. For example, in some embodiments, a subject anti-C1s antibody, when administered in one or more doses as monotherapy or in combination therapy to an individual having a complement-mediated disease or disorder, reduces macrophage infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to macrophage infiltration in the individual before treatment with the anti-C1s antibody.

In some embodiments, administering an anti-C1s antibody of the present disclosure to an individual reduces antibody deposition in the individual. For example, in some embodiments, a subject anti-C1s antibody, when administered in one or more doses as monotherapy or in combination therapy to an individual having a complement-mediated disease or disorder, reduces antibody deposition in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to antibody deposition in the individual before treatment with the anti-C1s antibody.

In some embodiments, administering an anti-C1s antibody of the present disclosure to an individual reduces anaphylatoxin (e.g., C3a, C4a, C5a) production in an individual. For example, in some embodiments, a subject anti-C1s antibody, when administered in one or more doses as monotherapy or in combination therapy to an individual having a complement-mediated disease or disorder, reduces anaphylatoxin production in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the level of anaphylatoxin production in the individual before treatment with the anti-C1s antibody.

The present disclosure provides for use of an anti-C1s antibody of the present disclosure or a pharmaceutical composition comprising an anti-C1s antibody of the present disclosure and a pharmaceutically acceptable excipient to treat an individual having a complement-mediated disease or disorder. In some embodiments, the present disclosure provides for use of an anti-C1s antibody of the present disclosure to treat an individual having a complement-mediated disease or disorder. In some embodiments, the present disclosure provides for use of a pharmaceutical composition comprising an anti-C1s antibody of the present disclosure and a pharmaceutically acceptable excipient to treat an individual having a complement-mediated disease or disorder.

The present disclosure provides for use of an anti-C1s antibody of the present disclosure in the manufacture of a medicament for the treatment of an individual having a complement-mediated disease or disorder.

The present disclosure provides for use of an anti-C1s antibody of the present disclosure or a pharmaceutical composition comprising an anti-C1s antibody of the present disclosure and a pharmaceutically acceptable excipient to inhibit complement activation. In some embodiments, the present disclosure provides for use of an anti-C1s antibody of the present disclosure or a pharmaceutical composition comprising an anti-C1s antibody of the present disclosure and a pharmaceutically acceptable excipient to inhibit complement activation in an individual having a complement-mediated disease or disorder. In some embodiments, the present disclosure provides for use of an anti-C1s antibody of the present disclosure to inhibit complement activation in an individual having a complement-mediated disease or disorder. In some embodiments, the present disclosure provides for use of a pharmaceutical composition comprising an anti-C1s antibody of the present disclosure and a pharmaceutically acceptable excipient to inhibit complement activation in an individual having a complement-mediated disease or disorder.

The present disclosure provides for use of an anti-C1s antibody of the present disclosure in the manufacture of a medicament for modulating complement activation. In some embodiments, the medicament inhibits complement activation. In some embodiments, the medicament inhibits complement activation in an individual having a complement-mediated disease or disorder.

The present disclosure provides for an anti-C1s antibody of the present disclosure or a pharmaceutical composition comprising an anti-C1s antibody of the present disclosure and a pharmaceutically acceptable excipient for use in medical therapy. In some embodiments, the present disclosure provides for an anti-C1s antibody of the present disclosure for use in medical therapy. In some embodiments, the present disclosure provides for a pharmaceutical composition comprising an anti-C1s antibody of the present disclosure and a pharmaceutically acceptable excipient for use in medical therapy.

The present disclosure provides for an anti-C1s antibody of the present disclosure or a pharmaceutical composition comprising an anti-C1s antibody of the present disclosure and a pharmaceutically acceptable excipient for treating an individual having a complement-mediated disease or disorder. In some embodiments, the present disclosure provides for an anti-C1s antibody of the present disclosure for treating an individual having a complement-mediated disease or disorder. In some embodiments, the present disclosure provides for a pharmaceutical composition comprising an anti-C1s antibody of the present disclosure and a pharmaceutically acceptable excipient for treating an individual having a complement-mediated disease or disorder.

The present disclosure provides for an anti-C1s antibody of the present disclosure or a pharmaceutical composition comprising an anti-C1s antibody of the present disclosure and a pharmaceutically acceptable excipient for modulating complement activation. In some embodiments, the present disclosure provides for an anti-C1s antibody of the present disclosure for modulating complement activation. In some embodiments, the present disclosure provides for a pharmaceutical composition comprising an anti-C1s antibody of the present disclosure and a pharmaceutically acceptable excipient for modulating complement activation. In some embodiments, the anti-C1s antibody inhibits complement activation.

Combination Therapy

An anti-C1s antibody of the present disclosure can be administered to an individual in need thereof alone (e.g., as monotherapy); or in combination therapy with one or more additional therapeutic agents.

For the treatment of AD, suitable additional therapeutic agents include, but are not limited to, acetylcholinesterase inhibitors, including, but not limited to, Aricept (donepezil), Exelon (rivastigmine), metrifonate, and tacrine (Cognex); an anti-Aβ antibody; non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art.

Another suitable additional therapeutic agent in the treatment of AD is an agent that inhibits tau aggregation, e.g., a napthoquinone derivative that inhibits tau aggregation, as described in U.S. Pat. No. 7,605,179. Another suitable additional therapeutic agent is an agent that inhibits phosphorylation of tau, e.g., a 3-substituted-4-pyrimidone derivative that inhibits tau protein kinase 1, as described in U.S. Pat. No. 7,572,793.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds that can be administered in the same or different formulations, by the same of different routes, and in the same or different dosage form type.

Individuals to be Treated

Individuals suitable for treatment with a subject anti-C1s antibody include individuals who have been diagnosed as having a complement-mediated disease or disorder; individuals at greater risk than the general population for developing a complement-mediated disease or disorder (e.g., individuals having a genetic predisposition to developing a complement-mediated disease or disorder); individuals with Parkinson's disease with dementia (PDD); individuals with Alzheimer's disease; and the like. In some cases, the individual is an adult human. In some cases, the adult human is 20 years or older, 30 years of age or older; 40 years of age or older, 50 years of age or older, 60 years of age or older, 70 years of age or older, or 80 years of age or older. For example, the adult human can be from 20 years old to 30 years old, from 30 years old to 40 years old, 40 years old to 50 years old, from 50 years old to 60 years old, from 60 years old to 70 years old, or older than 70 years. In some cases, the individual is a human child. In some cases, the human child is less than 20 years old, less than 10 years old, or less than 5 years old.

In Vitro Testing and Animal Models

The present disclosure provides a method to test the efficacy of a subject antibody in vitro or in vivo. In vitro testing includes methods to assay the binding of a subject antibody to a complement C1s protein, methods to assay the ability of a subject antibody to inhibit production of C4b2a complex, methods to identify the epitope, or characteristics of the epitope, to which an anti-C1s antibody of the present disclosure binds. Non-human animal models to test the efficacy of a subject antibody include experimental autoimmune encephalomyelitis (see, e.g., Weerth et al., Am J Path. 163: 1069-1080 (2003); Theien et al., J. Clin. Invest. 107:995-1006 (2001)), myasthenia gravis (see, e.g., Morgan et al., Clin. Exp. Immun. 146:294-302 (2006)), myocardial ischemia and reperfusion (see, e.g., Busche et al., GMS Ger. Med. Sci. 8:Doc20 (2010)), and Streptococcus pneumonia (see, e.g., Brown et al., Proc. Natl. Acad. Sci. 99:16969-16974)) models. Also suitable are non-human animal models of transplant rejection (see, e.g., Racki et al. (2010) *Transplantation* 89:527; and Baldwin et al. (2010) *Am. J. Transplantation* 10:1135). In some embodiments, the models are murine (e.g., rat or mouse) models. Such models are known to those skilled in the art.

Detection Methods

The present disclosure provides in vitro methods of detecting a complement C1s protein in a biological sample obtained from an individual; and methods of detecting a C1s protein in a living individual in vivo. A subject in vitro detection method can be quantitative. C1s protein or can thus serve as a biomarker for progression of a complement-mediated disease or disorder, or response to treatment for a complement-mediated disease or disorder.

The Complement C1s protein that is detected/quantitated can be full-length C1s protein or any fragment thereof that comprises the epitope to which an anti-C1s antibody of the present disclosure binds.

Suitable biological samples include, but are not limited to, blood, serum, plasma, urine, saliva, cerebrospinal fluid, interstitial fluid, ocular fluid, synovial fluid, solid tissue sample, tissue culture sample, cellular sample, and other biological samples known to those skilled in the art.

An in vitro method of the present disclosure of detecting a complement C1s protein in a biological sample obtained from an individual generally involves: a) contacting the biological sample with an anti-C1s antibody of the present disclosure; and b) detecting binding of the antibody to C1s protein present in the sample.

A detection method of the present disclosure can be used to determine whether an individual has, or is at risk of developing, complement-mediated disease or disorder. A detection method of the present disclosure can be used to determine the stage (severity) of a complement-mediated disease or disorder. A detection method of the present disclosure can be used to monitor progression of a complement-mediated disease or disorder in an individual. A detection method of the present disclosure can be used to determine an individual's response to a treatment regimen for treating a complement-mediated disease or disorder. A biological sample can be tested using a subject detection method, where the biological sample is obtained from an individual suspected of having a complement-mediated disease or disorder, an individual who has been diagnosed as having a complement-mediated disease or disorder, an individual who has a genetic predisposition to developing a complement-mediated disease or disorder, etc.

The present disclosure provides a method of diagnosing a complement-mediated disease or disorder in an individual. The method generally involves (a) determining the amount of a complement C1s protein in a biological sample obtained from the individual; and (b) comparing the amount of the complement C1s protein in the biological sample to a reference, a standard, or a normal control value that indicates the amount of Complement C1s protein in normal control subjects. A significant difference between the amount of C1s protein in the biological sample and the normal control value indicates that the individual has a complement-mediated disease or disorder. In some embodiments, the step of determining comprises contacting the biological sample with an anti-C1s antibody of the present disclosure and quantitating binding of the antibody to complement C1s protein present in the sample.

The present disclosure provides a method of monitoring the progression of a complement-mediated disease or disorder in an individual. The method generally involves comparing the amount of a complement C1s protein in a biological sample obtained from the individual at a first time point with the amount of a complement C1s protein in a biological sample obtained from the individual at a second time point. A difference in the amount of complement C1s protein in a biological sample obtained from the individual at a second time point, compared to the amount of complement C1s protein in a biological sample obtained from the individual at a first time point, can provide an indication as to: i) whether the complement-mediated disease or disorder is progressing or whether progression of the disease has been reduced or halted; and/or ii) how quickly the complement-mediated disease or disorder is progressing; and/or iii) whether the individual is exhibiting a beneficial clinical response to treatment with a drug or other treatment regimen for treating the complement-mediated disease or disorder. In some embodiments, the steps of determining comprise contacting the biological sample with an anti-C1s antibody of the present disclosure and quantitating binding of the antibody to complement C1s protein present in the sample. In some embodiments, the step of comparing indicates if the disease or disorder is progressing.

The present disclosure provides a method of monitoring response to treatment of a complement-mediated disease or disorder in an individual. The method generally involves comparing the amount of a complement C1s protein in a biological sample obtained from the individual at a first time point with the amount of a complement C1s protein in a biological sample obtained from the individual at a second time point. A difference in the amount of complement C1s protein in a biological sample obtained from the individual at a second time point, compared to the amount of complement C1s protein in a biological sample obtained from the individual at a first time point, can provide an indication as to whether the individual is exhibiting a beneficial clinical response to treatment with a drug or other treatment regimen for treating the complement-mediated disease or disorder. In some embodiments, the steps of determining comprise contacting the biological sample with an anti-C1s antibody of the present disclosure and quantitating binding of the antibody to complement C1s protein present in the sample. In some embodiments, the step of comparing indicates if progression of the disease is reduced or halted.

The present disclosure provides a method of staging a complement-mediated disease or disorder. For example, a subject method can provide for staging Alzheimer's disease. For example, the amount of a complement C1s protein in a biological sample from a living individual can provide an indication as to the Braak stage of AD. Braak and Braak (1995) *Neurobiol. Aging* 16:271. For example, the amount of a complement C1s protein in a biological sample from a living individual can provide an indication as to whether the individual is in transentorhinal stages I-II of AD; limbic stages III-IV of AD; or neocortical stages V-VI of AD.

The amount of a complement C1s protein in a biological sample can be assessed by any suitable method known in the art. Suitable methods include, but are not limited to, a protein ("Western") blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry.

The present disclosure provides a method of monitoring progression of a complement-mediated disease or disorder in an individual, where the method generally involves: a) determining a first amount of a complement C1s protein in a biological sample obtained from the individual at a first time point; b) determining a second amount of a complement C1s protein in a biological sample obtained from the individual at a second time point; and c) comparing the second amount of complement C1s protein with the first amount of complement C1s protein. In some embodiments, the determining steps comprise: i) contacting the biological sample with a subject anti-C1s antibody; and ii) quantitating binding of the antibody to complement C1s protein present in the sample. In some embodiments, the comparison indicates if the disease has progressed.

In some cases, the first time point is a time point before initiation of a treatment regimen, and the second time point is a time point after initiation of a treatment regimen. Thus, the instant disclosure provides a method of monitoring response to treatment with an agent that treats a complement-mediated disease or disorder, where the method involves: a) determining a first amount of a complement C1s protein in a biological sample obtained from the individual at a first time point that is before treatment with an agent to treat a complement-mediated disease or disorder is initiated; b) determining a second amount of a complement C1s protein in a biological sample obtained from the individual at a second time point that is after initiation of treatment with an agent to treat a complement-mediated disease or disorder; and c) comparing the second amount of complement C1s protein with the first amount of complement C1s protein.

A subject method of monitoring progression of a complement-mediated disease or disorder can also be applied to methods of monitoring progression of a tauopathy or synucleinopathy, e.g., Parkinson's disease (PD); dementia with Lewy Bodies (DLB); etc. For example, progression of PD with dementia (PDD) can be monitored with a subject method.

A subject method can involve use of a kit or an assay device comprising a subject anti-C1s antibody. The present disclosure provides kits and assay devices for carrying out a method as described herein. A subject kit includes an anti-C1s antibody of the present disclosure.

An anti-C1s antibody can be immobilized on an insoluble support (e.g., a test strip, a well of a multi-well plate, a bead (e.g., a magnetic bead), etc.). Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

An anti-C1s antibody of the present disclosure can comprise a detectable label. Where the antibody comprises a detectable label, a subject kit can include one or more reagents for developing the detectable label. A labeled antibody can comprise a label such as a chemiluminescent agent, a particulate label, a colorimetric agent, an energy transfer agent, an enzyme, a fluorescent agent, or a radioisotope. Suitable detectable labels include any composition detectable by spectroscopic, photochemical, biochemical, immunochemical, electrical, optical, or chemical means. Suitable detectable labels include, but are not limited to, fluorescent labels (e.g., fluorescein isothiocyanate, texas red, rhodamine, a green fluorescent protein, a red fluorescent protein, a yellow fluorescent protein, and the like); radiolabels (e.g., $^3$H, $^{125}$I, $^{35}$S, $^{14}$C, or $^{32}$P); and enzymes (e.g., horse radish peroxidase, alkaline phosphatase, luciferase, and other enzymes that act on a substrate to produce a product that can be detected by fluorometric, colorimetric, or spectrophotometric means).

In some cases, a method of the present disclosure for detecting/quantitating C1s in a biological sample obtained from an individual comprises treating the sample with a chelating agent, e.g., a calcium chelating agent, e.g., ethylenediaminetetraacetic acid (EDTA). The chelating agent disrupts a C1 complex, such that polypeptides that form the C1 complex are separated from one another, generating monomeric C1 complex components.

In some cases, a method of the present disclosure for detecting/quantitating C1s in a biological sample obtained from an individual comprises: a) contacting a biological sample with an immobilized first antibody that binds C1s but that does not compete with a subject anti-C1s antibody for binding to C1s (e.g., a rabbit polyclonal antibody that binds C1s), forming an immobilized first antibody/C1s complex; b) contacting the immobilized first antibody/C1s complex with a chelating agent (e.g., EDTA), forming an immobilized first antibody/C1s monomer complex; c) contacting the immobilized first antibody/C1s monomer complex with a monoclonal anti-C1s antibody of the present disclosure; and d) detecting binding of the monoclonal anti-C1s antibody to the immobilized C1s monomers. In some cases, a method of the present disclosure for detecting/quantitating C1s in a biological sample obtained from an individual comprises: a) treating the biological sample with a chelating agent (e.g., EDTA), forming C1s monomers; b) contacting the chelating agent-treated biological sample with an immobilized first antibody that binds C1s but that does not compete with a subject anti-C1s antibody for binding to C1s (e.g., a rabbit polyclonal antibody that binds C1s), forming an immobilized first antibody/C1s monomer complex; c) contacting the immobilized first antibody/C1s monomer complex with a monoclonal anti-C1s antibody of the present disclosure; and d) detecting binding of the monoclonal anti-C1s antibody to the immobilized C1s monomers. Detection of binding of the monoclonal anti-C1s antibody to the immobilized C1s monomers can be accomplished in various ways. For example, where the monoclonal anti-C1s antibody comprises a detectable label, the detectable label is detected using methods appropriate to the label. Alternatively, the monoclonal anti-C1s antibody can be detected using a detectably-labeled secondary antibody that binds the monoclonal anti-C1s antibody. A subject kit can comprise a subject monoclonal anti-C1s antibody; and can further comprise one or more of: 1) a chelating agent (e.g., EDTA); and 2) an anti-C1s antibody that does not compete with a subject anti-C1s antibody for binding to C1s (e.g., a polyclonal anti-C1s antibody, such as a rabbit polyclonal antibody).

A subject kit can further include one or more additional components, where suitable additional components include: 1) a positive control; 2) a buffer (e.g., a binding buffer; a wash buffer; etc.); 3) reagents for use in generating a detectable signal; and the like. Other optional components of the kit include: a protease inhibitor; a detectable label; etc. The various components of the kit can be present in separate containers or certain compatible components can be pre-combined into a single container, as desired.

In addition to above-mentioned components, a subject kit can include instructions for using the components of the kit to practice a subject method. The instructions for practicing a subject method are generally recorded on a suitable recording medium. For example, the instructions can be printed on a substrate, such as paper or plastic, etc. As such, the instructions can be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

An assay device can include a subject anti-C1s antibody immobilized on a solid substrate. The assay device can be in any of a variety of formats, e.g., a test strip, a dipstick; etc.

In Vivo Imaging

As discussed above, the present disclosure provides a method of detecting a complement C1s protein in a living individual, e.g., by an in vivo imaging technique. For example, in one embodiment, in vivo imaging of a C1s protein can be accomplished by positron emission tomography (PET), single photon emission tomography (SPECT), near infrared (NIR) optical imaging, or magnetic resonance imaging (MRI). In some embodiments, in vivo imaging is conducted using an IVIS® instrument, such as an IVIS® Spectrum. A subject anti-C1s antibody is administered to an individual, and the presence and/or amount of the complement C1s protein is detected. The anti-C1s antibody can comprise a label suitable for use in PET, SPECT, NIR, MRI, or IVIS. Such labels include a contrast agent or a radioisotope, where the contrast agent or radioisotope is one that is suitable for use in imaging, e.g., imaging procedures carried out on humans, as described above.

Generating a Report

In some instances, a subject detection method comprises detecting a complement C1s protein in a biological sample obtained from an individual; and, based on the amount of detected complement C1s protein, generating a report and/or directing therapy or management of the individual from whom the biological sample was obtained.

A report can include one or more of: an indication as to whether the individual likely has a complement-mediated disease or disorder; an indication of the severity of the complement-mediated disease or disorder; an indication as to whether the individual exhibits a beneficial clinical response to treatment for the complement-mediated disease or disorder; and the like.

Thus, a report can include information such as a predicted likelihood that the individual has, or will develop, a complement-mediated disease or disorder; a recommendation regarding further evaluation; a recommendation regarding therapeutic drug and/or other health management intervention; and the like.

For example, the methods disclosed herein can further include a step of generating or outputting a report providing the results of a subject assessment, which report can be provided in the form of an electronic medium (e.g., an electronic display on a computer monitor), or in the form of a tangible medium (e.g., a report printed on paper or other tangible medium). An assessment as to the likelihood that a person has, or is at risk of developing, a complement-mediated disease or disorder can be referred to as a "risk report," "a risk score," or "a likelihood score." A person or entity that prepares a report ("report generator") can also perform steps such as sample gathering, sample processing, and the like. Alternatively, an entity other than the report generator can perform steps such as sample gathering, sample processing, and the like. A risk assessment report can be provided to a user. A "user" can be a health professional (e.g., a clinician, a laboratory technician, or a physician).

Directing Health Management

In some instances, a subject detection method comprises detecting a complement C1s protein in a biological sample obtained from an individual; and, based on the amount of detected complement C1s protein, generating a report and/or directing therapy or management of the individual from whom the biological sample was obtained.

Thus, e.g., depending on the outcome of a subject detection method, a recommendation can be made that the individual undergo therapeutic intervention (treatment) for the complement-mediated disease or disorder and/or that the individual be considered for special health management. Therapeutic intervention can include, e.g., drug therapy for the treatment of Alzheimer's disease. Examples of drug therapy for the treatment of Alzheimer's disease include, but are not limited to, acetylcholinesterase inhibitors, including, but not limited to, Aricept (donepezil), Exelon (rivastigmine), metrifonate, and tacrine (Cognex); an anti-Aβ antibody (e.g., solanezumab); an anti-C1s antibody; non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept can be administered at 50 mg orally per day for 6 weeks, and, if well tolerated by the individual, at 10 mg per day thereafter.

Organ Preservation and Perfusion

The present disclosure provides compositions and methods for organ preservation and perfusion.

Compositions

The present disclosure provides a composition comprising an anti-C1s antibody of the present disclosure. Such compositions can include pharmaceutically acceptable excipients.

The composition can include one or more agents for perfusion into an organ or tissue. A perfusion composition can be used, e.g., for in situ or ex vivo perfusion of a tissue or organ. Where perfusion is performed in situ, the donor individual is usually not an alive and healthy individual.

The composition can include one or more agents that maintain an organ or a tissue intended for transplantation into a recipient individual. A preservation composition can be used, e.g., for ex vivo preservation of a tissue or organ.

For example, a tissue or organ obtained or to be obtained from a donor individual is perfused with a perfusion solution in situ or ex vivo at the time of or after removal from a donor individual. The tissue or organ can be stored in a preservation solution ex vivo for a period of time before the tissue or organ is transplanted into a recipient individual. In some cases, the perfusion composition and the preservation composition are the same.

In some cases, a subject composition is an aqueous solution that comprises: (a) an anti-C1s antibody of the present disclosure; and (b) one or more of: (i) a salt; (ii) an agent that reduces edema; (iii) an agent that scavenges free radicals (an "oxygen free radical inhibitor" or an "oxygen free radical scavenger"); and (iv) an energy supply system component. In some cases, a subject composition is an aqueous solution that comprises: (a) an anti-C1s antibody of the present disclosure; and (b) one or more of: (i) a saccharide (e.g., a monosaccharide, a disaccharide, a trisaccharide, a polysaccharide); and (ii) an agent having pH buffering properties; and, optionally, (c) one or more of: (iii) a calcium transport blocker; (iv) a thromboxane inhibitor; (v) a calcium chelating agent; and (vi) an iron chelating agent.

Suitable saccharides include, but are not limited to, sucrose, raffinose, and mannitol. Suitable pH buffer agents include a sodium phosphate buffer, a potassium phosphate buffer, and the like; e.g., $Na_2PO_4$, $NaH_2PO_4$, $K_2PO_4$, $KH_2PO_4$, and the like.

Suitable oxygen free radical scavengers include, but are not limited to, allopurinol and reduced glutathione. A suitable energy supply system component includes adenosine (or adenosine triphosphate (ATP)).

Examples of suitable calcium chelators include citrate and ethylene glycol tetraacetic acid (EGTA). An example of a suitable iron chelator is ethylenediaminetetraacetic acid (EDTA).

Agents that reduce edema include impermeant anions and colloidal osmotic agents.

As used herein, the term "impermeant anion" refers to compounds that counteract swelling in organs that have been exposed to hypothermic temperatures. Examples of impermeant anions include, but are not limited to, gluconate and lactobionic acid.

Agents that reduce edema include a colloidal osmotic agent, e.g., poly(ethylene glycol) (PEG), succinylated gelatin, Ficoll (a polysaccharide), or a starch product (e.g., hydroxyethyl starch).

In some cases, a subject composition also includes an amino acid, e.g., glutamine, glycine, or N-acetylcysteine.

In some cases, a subject composition also includes an antimicrobial agent, e.g., an antibiotic, an anti-fungal agent, and the like.

A subject composition can include inorganic or organic solutes. A suitable inorganic solute is an electrolyte including cations and/or anions, for example selected from $Na^+$, $K^+$, $Cl^-$, $OH^-$, $Ca^{2+}$, $Mg^{2+}$, and the like. Electrolytes can be present at a concentration of, e.g.: (i) $Na^+$, from about 50 mmol/L to about 150 mmol/L; (ii) $K^+$, from about 0 mmol/L to about 25 mmol/L; (iii) $Cl^-$ from about 0 mmol/L to about 100 mmol/L; (iv) $OH^-$, from about 0 mmol/L to about 75 mmol/L; (v) $Ca^{2+}$, from about 0 mmol/L to about 2 mmol/L; (vi) $Mg^{2+}$, from about 0 mmol/L to about 10 mmol/L.

The osmolality of a subject composition can range from about 300 mosmol/l to about 450 mosmol/l, e.g., from about 300 mosmol/l to about 325 mosmol/l, from about 325 mosmol/l to about 350 mosmol/l, from about 350 mosmol/l to about 375 mosmol/l, from about 375 mosmol/l to about 400 mosmol/l, from about 400 mosmol/l to about 425 mosmol/l, or from about 425 mosmol/l to about 450 mosmol/l.

The pH of a subject composition can range from about 6.9 to about 7.8, e.g., a subject composition can have a pH of 6.9, 7.0, 7.1, 7.2, 7.3, 7.4, 7.5, 7.6, 7.7, 7.8, or 7.9.

In some cases, a subject composition is an aqueous solution that comprises: (a) an anti-C1s antibody of the present disclosure; and (b) one or more of: (i) hydroxyethyl starch; (ii) lactobionic acid; and (iii) raffinose.

In some cases, a subject composition is an aqueous solution that comprises: (a) an anti-C1s antibody of the present disclosure; (b) potassium lactobionate (100 mmol); (c) $KH_2PO_4$ (25 mmol); (d) $MgSO_4$ (4 5 mmol); (e) raffinose (30 mmol); (f) adenosine (5 mmol); (g) glutathione (3 mmol); (h) insulin (100 Units); (i) a broad-spectrum antibiotic such as trimethoprim (16 mg/mL); j) dexamethasone (8 mg/L); k) allopurinol (1 mM); and 1) hydroxyethyl starch (e.g., hydroxyethyl starch) having a molecular weight of about 200,000 daltons to about 300,000 daltons and a degree of substitution of from about 0.4 to 0) (50 g/L).

In some cases, a subject composition is an aqueous solution that comprises: (a) an anti-C1s antibody of the present disclosure; and one or more of: (i) hydroxyethyl starch (30 g/L to 100 g/L); (ii) NaCl (85 mM to 145 mM); (iii) KCl (3 mM to 6 mM); (iv) $CaCl_2$ (1.0 mM to 1.6 mM); (v) $KH_2PO_4$ (0.7 mM to 1.3 mM); (vi) $MgSO_4$ (0.9 mM to 1.5 mM); (vii) allopurinol (0.05 mM to 5.0 mM); (viii) desferrioxamine (0.02 mM to 2.0 mM); (ix) glutathione (0.5 mM to 10.0 mM); (x) nicardipene (0.1 μM to 5.0 μM); (xi) adenosine (0.1 mM to 5.0 mM); (xii) fructose (1.0 mM to 50.0 mM); (xiii) glucose (1.0 mM to 50.0 mM); (xiv) insulin (5 U/L to 250 U/L); (xv) 3-(N-morpholino)propanesulfonic acid (MOPS) (2 mM to 40 mM).

In some cases, a subject composition comprises:
(a) an anti-C1s antibody of the present disclosure;
(b) potassium lactobionate (e.g., 100 mM);
(c) $KH_2PO_4$ (e.g., 5 mM);
(d) raffinose (e.g., 30 mM);
(e) adenosine (e.g., 5 mM);
(f) glutathione (e.g., 3 mM);
(g) allopurinol (e.g., 1 mM); and
(h) hydroxyethyl starch (e.g., 50 g/L).

A subject anti-C1s antibody is present in a subject tissue/organ preservation or perfusion solution in an effective amount. An "effective amount" of a subject anti-C1s antibody is an amount that inhibits production of C4b2a complex by at least 10%, at least 20%, at least 30%, at least 40%, at least 50%, at least 60%, at least 65%, at least 70%, at least 75%, at least 80%, at least 85%, at least 90%, at least 95%, or 100%, compared to the level of C4b2a in the absence of the anti-C1s antibody. The concentration of the anti-C1s antibody in the composition can range from about 1 mg/mL to about 200 mg/mL, e.g., from about 1 mg/mL to about 5 mg/mL, from about 5 mg/mL to about 10 mg/mL, from about 10 mg/mL to about 25 mg/mL, from about 25 mg/mL to about 50 mg/mL, from about 50 mg/mL to about 100 mg/mL, or from about 100 mg/mL to about 150 mg/mL.

The present disclosure provides an isolated (e.g., ex vivo) organ or tissue present in a preservation/perfusion solution as described above.

Methods of Organ Perfusion and Methods of Organ Preservation

The present disclosure provides methods of tissue or organ perfusion, as well as methods of ex vivo tissue or organ preservation using a composition comprising an anti-C1s antibody as described herein.

Perfusion methods generally involve introducing a perfusion solution comprising an anti-C1s antibody of the present disclosure into and/or around a donor tissue or donor organ in situ or ex vivo in an amount sufficient to perfuse the tissue or organ with the perfusion solution. Where perfusion is performed in situ, the donor individual is usually not an alive and healthy individual. Perfusion can be accomplished by, for example, introducing a perfusion solution of the present disclosure into a vascular bed of the tissue or organ. Perfusion can be performed so as to flush the tissue or organ with the perfusion solution, e.g., to at least partially displace blood present in the vasculature.

Preservation methods generally involve introducing a preservation solution comprising an anti-C1s antibody of the present disclosure into and/or around a donor tissue or organ ex vivo in an amount sufficient to maintain the tissue or organ for later use, e.g., for use in transplant.

Perfusion and preservation methods described herein in general provide for inhibition of complement activation in the tissue or organ. Thus, the present disclosure provides a method for inhibiting complement activation in a tissue or organ, the method involving introducing a perfusion or preservation solution as described herein into or around a tissue or organ in situ or ex vivo, where the perfusion or preservation solution is introduced in an amount sufficient to inhibit complement activation in the tissue or organ.

Organs and tissues that can be preserved using a subject method include, but are not limited to, a kidney, a liver, a pancreas, a heart, a lung, skin, blood tissue (including whole blood; red blood cells; white blood cells; cord blood; and the like, where the blood tissue may comprise an isolated population of blood cells (buffy coat; red blood cells; platelets; lymphocytes; T cells; B cells; or some other population), or where the blood tissue comprises a mixed population of cells), small intestine, an endothelial tissue, a vascular tissue (e.g., a blood vessel), an eye, a stomach, a thymus, bone, bone marrow, cornea, a heart valve, an islet of Langerhans, or a tendon. As used herein, "organ" encompasses a whole organ or a part of an organ. As used herein, "tissue" encompasses a whole tissue or part of a tissue.

The organ or tissue can be of human origin. The organ or tissue can be of non-human animal (e.g., porcine) origin. In some cases, the tissue or organ is an allograft, i.e., the tissue or organ is allogeneic to a prospective recipient. In some cases, the tissue or organ is a xenograft, i.e., the tissue or organ is from a xenogeneic source relative to a prospective recipient. The organ or tissue can be obtained from a living individual, or from a recently deceased individual (e.g., where the organ or tissue is obtained from an individual within about 1 minute or a few hours following death of the individual).

An organ or tissue can be stored in a subject preservation or perfusion solution at a hypothermic temperature, or at a normothermic temperature. For example, an organ or tissue can be stored in a subject preservation or perfusion solution at a hypothermic temperature of from about 1° C. to about 10° C. As another example, an organ or tissue can be stored in a subject preservation or perfusion solution at a normothermic temperature of from about 12° C. to about 24° C.

An organ or tissue can be stored in a subject preservation or perfusion solution for a period of time of from about 1 minute to about 24 hours, e.g., from about 1 minute to about 15 minutes, from about 15 minutes to about 30 minutes, from about 30 minutes to about 1 hour, from about 1 hour to about 4 hours, from about 4 hours to about 8 hours, from about 8 hours to about 12 hours, or from about 12 hours to about 24 hours. In some cases, an organ or tissue can be stored in a subject preservation or perfusion solution for a period of time of longer than 24 hours. An organ or tissue can be perfused with a subject preservation or perfusion solution for a period of time of from about 1 minute to about 24 hours, e.g., from about 1 minute to about 15 minutes, from about 15 minutes to about 30 minutes, from about 30 minutes to about 1 hour, from about 1 hour to about 4 hours, from about 4 hours to about 8 hours, from about 8 hours to about 12 hours, or from about 12 hours to about 24 hours.

Tables 2 and 3 provide a listing of the SEQ ID NOs disclosed in the application. FIG. 2 provides Table 2. Table 3 is provided below. It is to be appreciated that since nucleic acid sequencing technology is not entirely error-free, the nucleic acid sequences and amino acid sequences presented herein represent, respectively, apparent nucleic acid sequences of nucleic acid molecules of the embodiments and apparent amino acid sequences of proteins of the embodiments.

TABLE 3

Listing of non-antibody amino acid sequences disclosed herein.

| SEQ ID NO: | Source | Description/Sequence |
|---|---|---|
| 9 | Homo sapiens | Human complement C1s protein; sequence depicted in FIG. 1 |
| 10 | Synthetic | $(GSGGS)_n$ |
| 11 | Synthetic | $(GGGS)_n$ |
| 12 | Synthetic | GGSG |
| 13 | Synthetic | GGSGG |
| 14 | Synthetic | GSGSG |
| 15 | Synthetic | GSGGG |
| 16 | Synthetic | GGGSG |
| 17 | Synthetic | GSSSG |
| 18 | Synthetic | YPYDVPDYA |
| 19 | Synthetic | DYKDDDDK |
| 20 | Synthetic | EQKLISEEDL |
| 21 | Synthetic | HHHHH |
| 22 | Synthetic | HHHHHH |
| 23 | Synthetic | WSHPQFEK |
| 24 | Synthetic | RYIRS |
| 25 | Synthetic | FHHT |
| 26 | Synthetic | WEAAAREACCRECCARA |

TABLE 3-continued

Listing of non-antibody amino acid sequences disclosed herein.

| SEQ ID NO: | Source | Description/Sequence |
|---|---|---|
| 27 | Synthetic | TFFYGGCRGKRNNFKTEEY |
| 28 | Synthetic | TFFYGGSRGKRNNFKTEEY |
| 29 | Synthetic | CTFFYGGSRGKRNNFKTEEY |
| 30 | Synthetic | TFFYGGSRGKRNNFKTEEYC |
| 31 | Synthetic | TFVYGGCRAKRNNFKS |

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second (s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Production and Characterization of Anti-Complement C1s IPN003 Antibody

Anti-C1s monoclonal antibody IPN003 (also referred to as "IPN-M34" or "M34") was produced as follows: Immunization of BALB/c and NZBW mice with purified human activated C1s protein, two-chain form (EMD Millipore, Billerica, Mass.) (SEQ ID NO:9) generated two independent hybridoma libraries which were screened with C1s protein using techniques known to those skilled in the art (see, e.g., Galfre et al., Methods in Enzymology 73:346 (1981). Flow cytometry was used to generate single cell clones, and supernatants from these individual clones were screened for binding to biotin-labeled activated C1s using a solution phase monoclonal antibody capture assay, such as that disclosed, e.g., in Nix et al., in Immunoassays, A Practical Approach, editor J. P. Gosling, pp. 239-261, Oxford University Press (2000). One hundred seventy-one clones bound activated C1s with high affinity. One of the clones isolated from NZBW mice that bound activated C1s produced an antibody denoted IPN003 (or IPN-M34; or M34; or TNT003).

Amino acid sequencing of the VH and VL regions of IPN003 anti-C1s antibody was conducted using techniques known to those skilled in the art (MCLAB, South San Francisco, Calif.). Specifically, cell pellets were prepared from the hydridoma cell line expressing the IPN003 monoclonal antibody, and RNA was extracted using an RNAqueous®-4PCR kit (Life Technologies Inc., Grand Island, N.Y.). V-regions were amplified by reverse transcription-polymerase chain reaction (RT-PCR) using degenerate primer pools for murine antibody signal sequences together with constant region primers for IgMVH, IgGVH, IgKVL and IgλVL. The polymerase chain reaction (PCR) products obtained from each of the successful amplifications were purified and cloned into a 'TA' cloning vector (pGEM-T® Easy, Promega, Madison, Wis.) from which sequences were obtained. The deduced amino acid sequences of the VH and VL regions of the IPN-M34 antibody are provided in Table 2. Also provided in Table 2 (FIG. 2) are the CDRs of IPN003.

Example 2

Binding Characteristics of IPN003

IPN003 binding characteristics were compared to those of M81. For M81, see, e.g., Matsumoto et al. (1986) *J. Immunol.* 137:2907; Matsumoto et al. (1989) *J. Immunol.* 142:2743; and Nakagawa et al. (1999) *Ann. Rheum. Dis.* 58:175.

IPN003 Competes with M81 for Binding to Human C1s.

To determine if IPN003 could compete binding of M81 to human C1s, competition assays were performed, in which biotin-labeled M81 (final concentration 0.5E-9 M) was incubated with increasing concentrations of unlabeled antibodies in wells coated with human C1s. The data are shown in FIG. 3.

Unlabeled M81 competed binding of labeled M81 with an $IC_{50}$ of 3E-9 M, whereas a control antibody did not compete. As shown in FIG. 3, IPN003 (M34) competed binding of M81 to human C1s. IPN003 was a more potent inhibitor of M81 binding ($IC_{50}$ of 0.33E-9 M) than M81, suggesting that the epitope of IPN003 is distinct from, but overlapping with, the epitope recognized by M81.

IPN003 Inhibits Human C1s Activation of Human C4.

Figure 4:
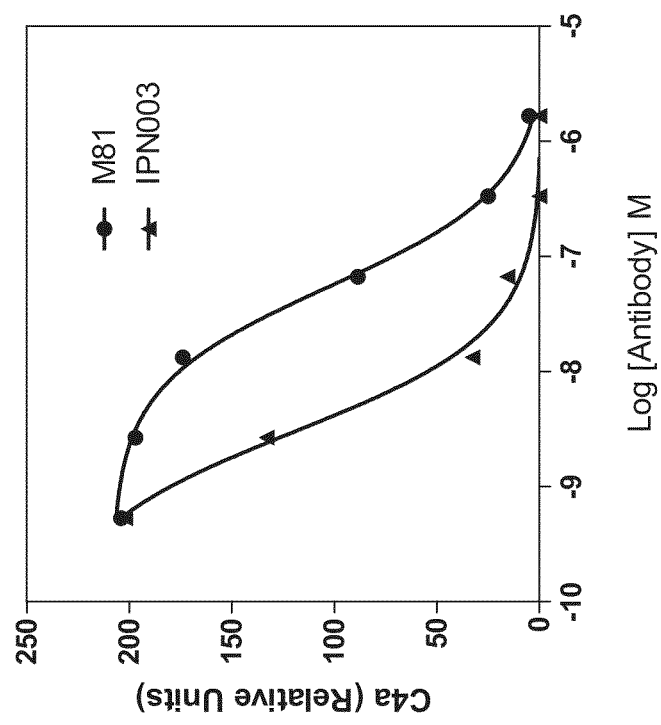
FIG. 4 depicts IPN003 inhibition of C1s-mediated activation of human complement protein C4.

Human complement protein C4 was incubated with activated human C1s in the presence of increasing concentrations of monoclonal antibodies M81 or IPN003. As shown in FIG. 4, the data demonstrate that IPN003 inhibits C1s mediated activation of human complement protein C4. IPN003 inhibited activation of C4 with an $IC_{50}$ of 3E-9 M. In contrast, M81 was a much less potent inhibitor and inhibited C4 activation with an $IC_{50}$ of 55E-9 M.

IPN003 Inhibits Human Complement Mediated Cell Lysis.

Figure 5:
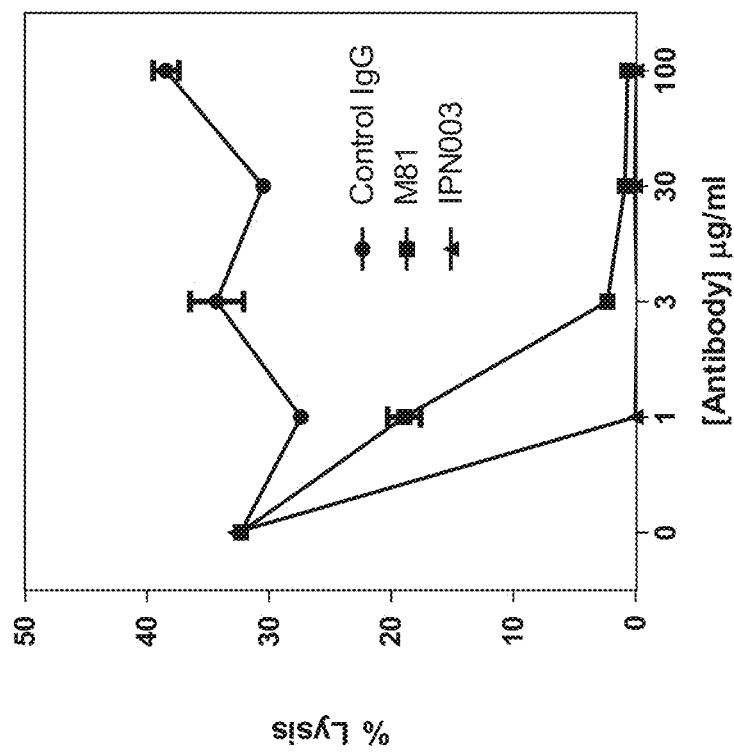
FIG. 5 depicts the effect of IPN003 on activation of the intact classical complement cascade using a standard hemolysis assay.

The ability of IPN003 to inhibit complement-mediated cell lysis was measured in a standard sheep red blood cell (sRBC) hemolysis assay using human serum as a source of complement proteins. The data are shown in FIG. 5.

A control IgG had no effect on cell lysis, whereas IPN003 inhibited cell lysis with an $IC_{50}$ of 1.1E-9 M. In contrast, M81 was a much less potent inhibitor than IPN003, and inhibited sRBC lysis with an $IC_{50}$ of 11.3E-9 M. Thus, the data presented in FIG. 5 show that IPN003 can inhibit activation of the intact classical complement cascade using a standard hemolysis assay; and that IPN003 is significantly more active than M81, consistent with the data presented in FIGS. 3 and 4.
IPN003 Inhibits Cell Lysis Mediated by *Macaca fascicularis* Complement and by *Macaca mulatta* Complement.

To determine whether IPN003 could inhibit complement-mediated cell lysis in a species suitable for toxicology studies, hemolysis assays were performed in which complement proteins were provided by serum from *Macaca fascicularis* and from *Macaca mulatta*, two monkey species that are considered suitable for toxicology studies. The data are shown in FIGS. 6 and 7.

Figure 6:
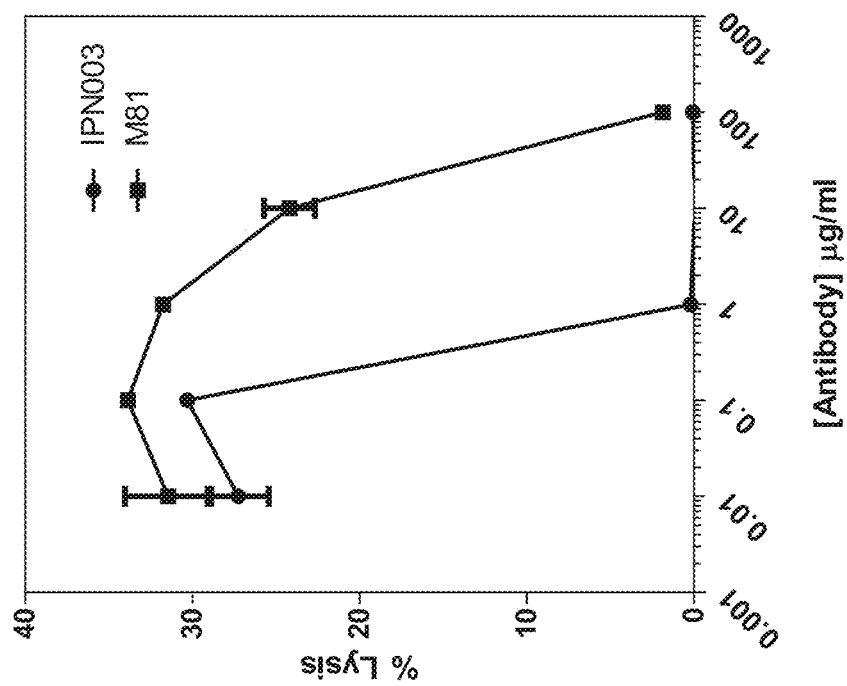
FIGS. 6 and 7 depict inhibition by IPN003 of complement in serum from two species of monkey.

As shown in FIG. 6, IPN003 inhibited cell lysis, mediated by serum from *Macaca fascicularis*, with an $IC_{50}$ of 4.6E-9 M. In contrast M81 was a much less potent inhibitor and inhibited sRBC lysis with an $IC_{50}$ of 189E-9 M.

Figure 7:
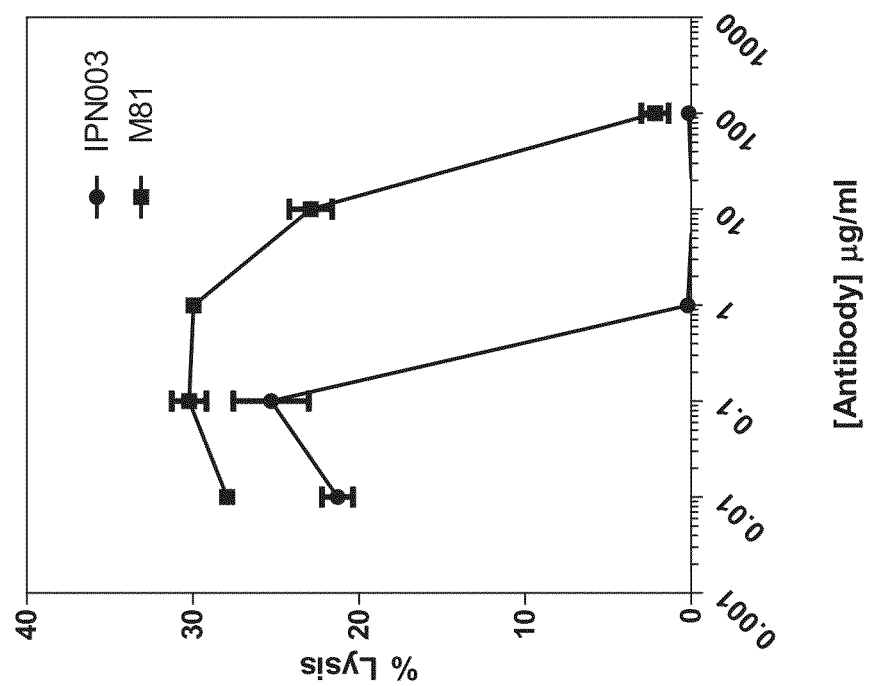

As shown in FIG. 7, IPN003 inhibited cell lysis, mediated by serum from *Macaca mulatta*, with an $IC_{50}$ of 4.5E-9 M. In contrast M81 was a much less potent inhibitor and inhibited sRBC lysis with an $IC_{50}$ of 83E-9 M.

The data presented in FIGS. 6 and 7 also strongly suggest that IPN003 cross-reacts with C1s from at least two monkey species. The data also indicate that IPN003 is a more potent inhibitor of complement activation than M81.
IPN003 is Specific for the C1s Component of the Complement Cascade.

Figure 8:
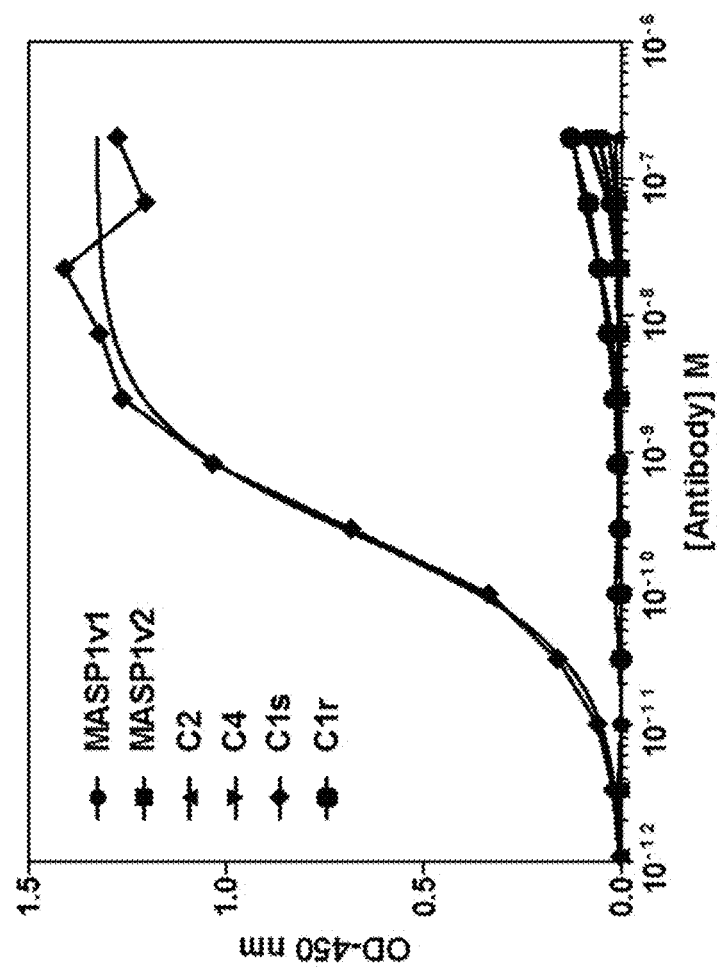
FIG. 8 depicts the specificity of IPN003 for C1s.

To determine whether IPN003 could bind other components of the complement cascade, ELISA assays were performed with target proteins immobilized on micro-titer plates. The data, shown in FIG. 8, demonstrate that IPN003 is specific for C1s and does not bind to other components of the complement pathway.

Figure 10:
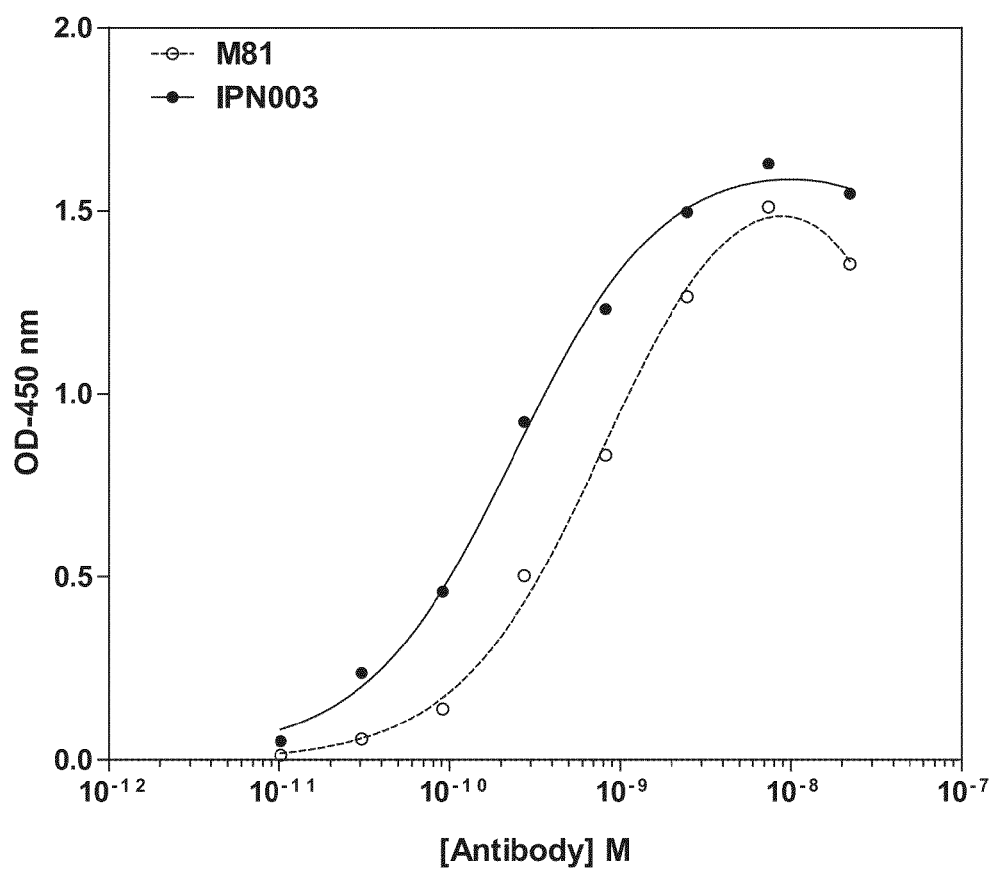
FIG. 10 depicts binding of IPN003 and M81 to rat C1s.

Table 4 (provided in FIG. 9) summarizes the binding characteristics of IPN003.
IPN003 Binds Rat C1s ELISA assays were performed with purified rat C1s immobilized on micro-titer plates and increasing dilutions of IPN003 or M81. The data, presented in FIG. 10, show that IPN003 bound rat C1s with a $K_D$ of 0.2E-9 M whereas M81 bound rat C1s with a $K_D$ of 0.8E-9 M.

Example 3

Inhibition by IPN003 of Rat C1s-Mediated Cleavage of Human C4

Figure 11:
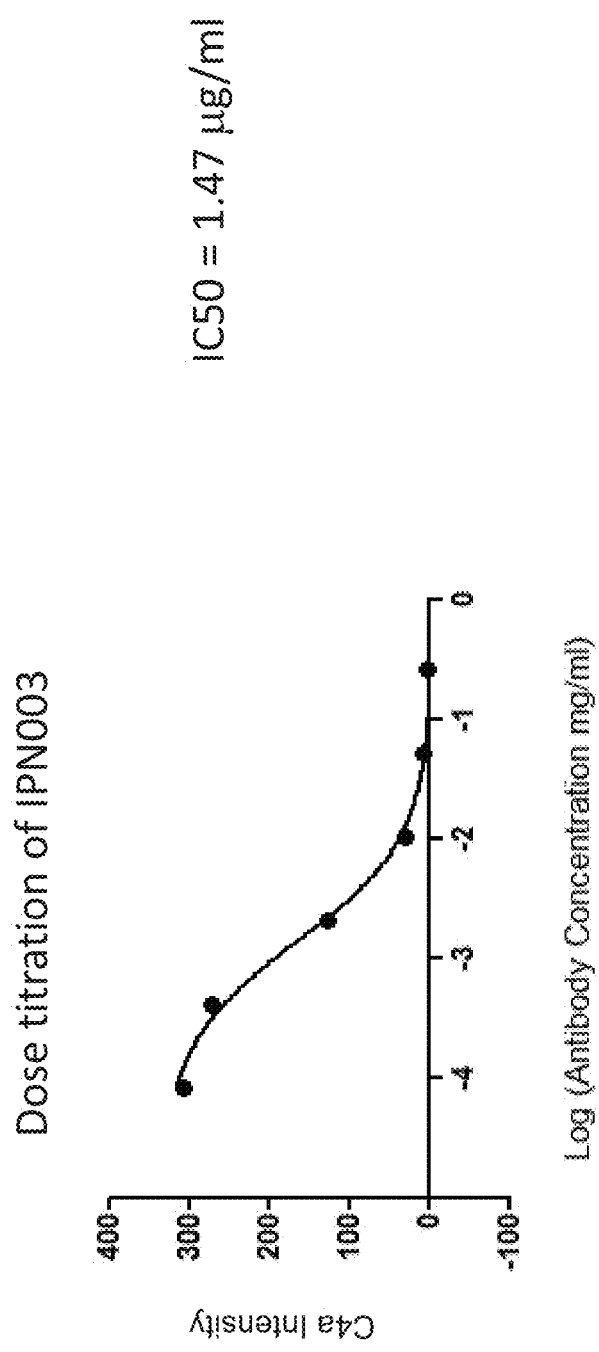
FIG. 11 depicts IPN003 inhibition of rat C1s-mediated cleavage of human C4.

Human C4 (0.25 mg/ml) was incubated at 37° C. with rat C1s (0.64 µg/ml), with various concentrations of IPN003. Samples containing the reaction products were reduced; the reduced samples were separated on a 4-12% NuPAGE gel; and the gel was stained with Coomassie blue. The C4a cleavage product band on the Coomassie gel was quantitated on a Licor scanner. The results are shown in FIG. 11. As shown in FIG. 11, IPN003 inhibits rat C1s-mediated cleavage of human C4 in a concentration-dependent manner, with an $IC_{50}$ of 1.47 µg/ml.

A comparison of IPN003 inhibition of rat C1s-mediated and human C1s-mediated cleavage of human C4 was carried out. 5 µl rat C1s (0.64 µg/ml) or 5 µl human C1s (0.2 µg/ml) was added to 5 µl of 1 mg/ml IPN003 or an irrelevant control IgG; and the mixture kept for 30 minutes at room temperature. Following incubation, 10 µl of 1 mg/ml human C4 was added; this mixture was incubated at 37° C. for 80 minutes. Samples containing the reaction products were analyzed by Coomassie-stained gels, and by ELISA. The results are shown in FIG. 12. As shown in FIG. 12, IPN003 inhibits rat C1s-mediated cleavage of human C4 to a similar degree as IPN003 inhibits human C1s-mediated cleavage of human C4.

Example 4

IPN003 Inhibition of Patient Serum-Induced Human RBC Lysis and C3b Deposition

Assays were carried out to determine whether IPN003 inhibits autoimmune hemolytic anemia (AIHA) patient serum-induced human RBC lysis and C3b deposition.

A sample containing 10 µl packed human RBC (hRBC) and 50 µl patient serum was incubated for 30 minutes at 30° C. Normal human serum served as a control. After the 30-minute incubation, the sample was centrifuged and washed once. Then, complement competent human serum (12.5%) with or without IPN003 (100 µg/ml) was add to sensitized hRBC; and samples were incubated for 1 hr at 37° C. After the one-hour incubation period, the supernatants were collected, and absorbance at 540 nm measured. The results are shown in FIG. 13. The data presented in FIG. 13 show that IPN003 inhibits hemolysis of hRBC pre-incubated in AIHA serum from Patient P3-1. The background hemolysis mediated by human normal serum is mediated by a mechanism that is independent of complement.

Assays were carried out to determine whether IPN003 inhibits AIHA patient serum-induced C3b deposition on human RBCs. As shown in FIG. 14, IPN003 completely inhibits C3b deposition on hRBCs that were incubated with an AIHA serum sample (patient P3-1).

Example 5

Humanized IPN003 Variants

Humanized variants of IPN003 were generated. Amino acid sequences of the heavy chain VH domains of humanized variants 1-4, and nucleotide sequences encoding the heavy chain VH domain of the humanized variants, are shown in FIGS. 16-19. Amino acid sequences of the light chain VL domain of humanized variants 1-3, and nucleotide sequences encoding the light chain VL domain of the humanized variants, are shown in FIGS. 20-22. Amino acid differences relative to the amino acid sequence of IPN003 (VL SEQ ID NO:37; VH SEQ ID NO:38) are summarized in Tables 7 and 8 (FIG. 23).

Single letter amino acid codes are as follows (with 3-letter amino acid codes in parentheses):
G—Glycine (Gly)
P—Proline (Pro)
A—Alanine (Ala)
V—Valine (Val)
L—Leucine (Leu)
I—Isoleucine (Ile)
M—Methionine (Met)
C—Cysteine (Cys)
F—Phenylalanine (Phe)
Y—Tyrosine (Tyr)
W—Tryptophan (Trp)
H—Histidine (His)
K—Lysine (Lys)
R—Arginine (Arg)
Q—Glutamine (Gln)
N—Asparagine (Asn)
E—Glutamic Acid (Glu)
D—Aspartic Acid (Asp)
S—Serine (Ser)
T—Threonine (Thr)

Example 6

Characterization of Humanized IPN003 Variants

The relative binding affinities for various humanized IPN003 variants to activated C1s are shown in Table 9, which is presented in FIG. 24. The relative binding affinities for various humanized IPN003 variants to pro-C1s are shown in Table 10, which is presented in FIG. 24. Humanized variants bind active C1s with an approximately 2-fold higher affinity than the parental IPN003 antibody. For comparison, the $K_D$ (M) of IPN003 to human C1s is 1.58E-9 to 2.04E-9; the $K_{on}$ (1/Ms) is 3.56E+05; and the $K_{dis}$ (1/s) is 5.53E-04.

Humanized variants were generated, having an IgG4 constant region that is hinge-stabilized (having an S241P substitution) and that has reduced effector function (having an L235E substitution). A1124 combinations (VH variant 1+Vk variant 1; VH variant 1+Vk variant 2; VH variant 1+Vk variant 3; VH variant 2+Vk variant 1; VH variant 2+Vk variant 2; VH variant 2+Vk variant 3; VH variant 3+Vk variant 1; VH variant 3+Vk variant 2; VH variant 3+Vk variant 3; VH variant 4+Vk variant 1; VH variant 4+Vk variant 2; VH variant 4+Vk variant 3) were transiently expressed in HEK cells. Each humanized variant was tested for the ability to compete with IPN003 for binding to C1s. The data are shown in FIG. 25.

Figure 26:
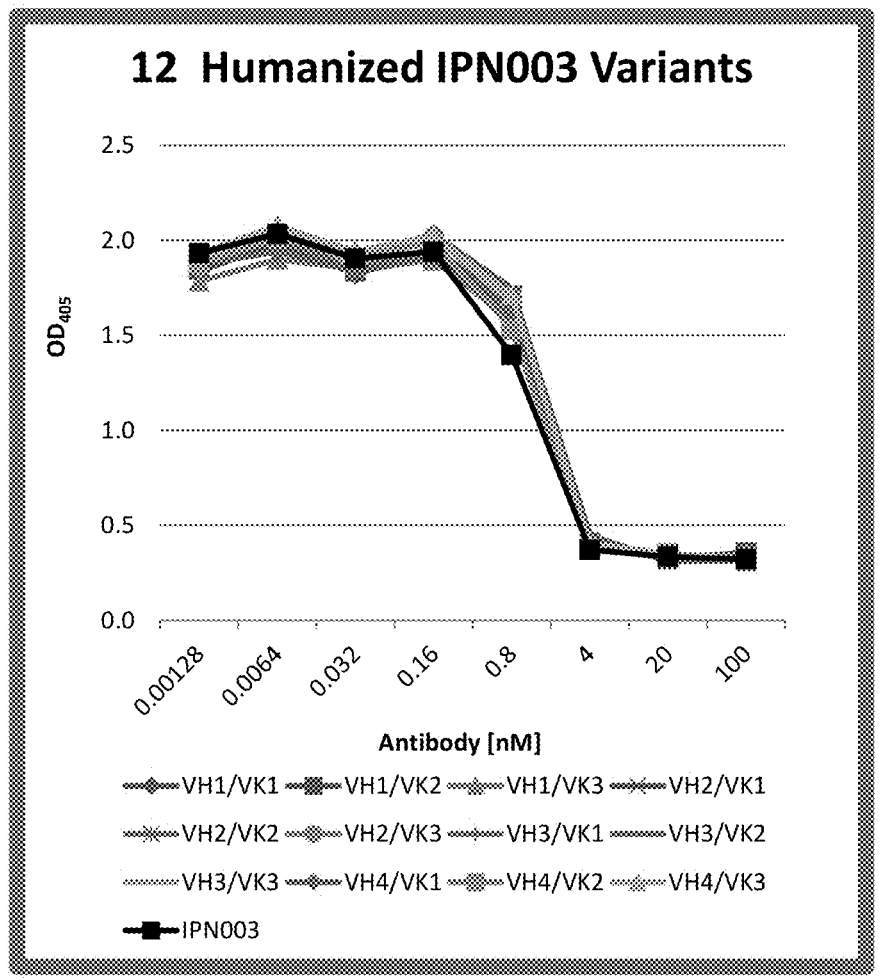
FIG. 26 depicts inhibition of the complement classical pathway by humanized variants of IPN003.

Each humanized variant was tested in a commercially available assay that measures complement classical pathway (CP) activation. The results are shown in FIG. 26. The data show that all 12 humanized variants inhibit CP activation with an $IC_{50}$ similar to that of IPN003.

Figure 27A:
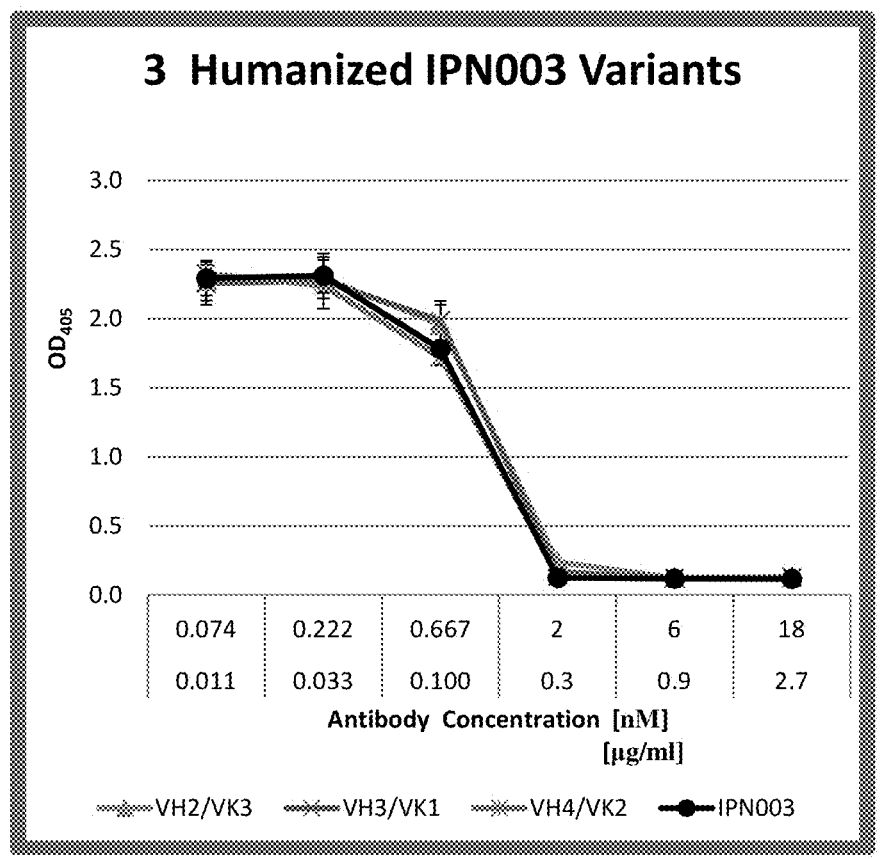
FIGS. 27A and 27B depict the effects of 3 humanized IPN003 variants on activation of the classical complement pathway (FIG. 27A) and the alternative complement pathway (FIG. 27B).
Figure 27B:
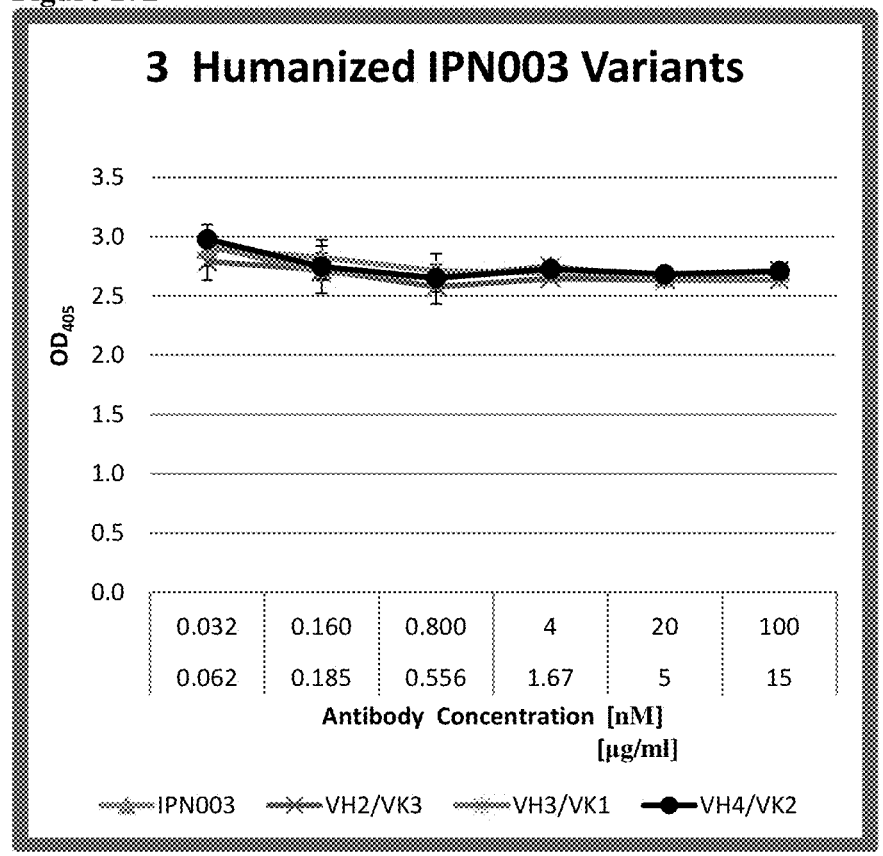

As shown in FIGS. 27A and 27B, of the 3 humanized variants tested, all were specific for the classical pathway. FIG. 27A shows concentration-dependent inhibition of CP by humanized variants VH2/VK3, VH3/VK1, and VH4/VK2. IPN003 is shown for comparison. FIG. 27B shows the effect of humanized variants VH2/VK3, VH3/VK1, and VH4/VK2 on the alternative pathway (AP).

Humanized variants were tested for inhibition of red blood cell (RBC) lysis, and inhibition of the deposition of C3b on RBCs. The data are shown in FIG. 28.

Example 7

Inhibition of Complement-Dependent Hemolysis

Assays were carried out to determine whether IPN003, or a humanized variant of IPN003, can inhibit cold agglutinin disease (CAD) patient plasma-induced human RBC lysis. Assays were also conducted to determine whether IPN003, or a humanized variant of IPN003, can inhibit anaphylatoxin production.

Hemolysis assays were conducted essentially as described in Example 4. Type O⁻ normal human red blood cells were incubated in the presence of cold agglutinin disease (CAD) patient plasma (CAD patient 5; "CAD P5") at 4° C., allowing autoantibodies in the plasma to bind the RBC, thereby generating sensitized hRBCs. 10 mM EDTA was added during sensitization to prevent complement activation. After ~½ hour, plasma was washed away, and 25% normal human serum containing active complement and antibody (IPN003, humanized variant of IPN003, or control IgG2a) was added. After addition of the human serum and antibody to the sensitized hRBCs, samples were incubated for 1 hr at ~18° C. After the one-hour incubation period, the supernatants were collected, and absorbance at 540 nm measured. The results are shown in FIG. 29.

As shown in FIG. 29, plasma of CAD patient P5 induced hRBC lysis. IPN003 and a humanized variant of IPN003, but not control IgG2a, inhibited complement-dependent CAD patient plasma-mediated hRBC hemolysis. Complement-dependent lysis was inhibited in a concentration-dependent manner.

Anaphylatoxins C3a, C4a, and C5a generation was tested using the CAD P5 supernatant from the above-described hemolysis experiment. The data are shown in FIG. 30. As shown in FIG. 30, IPN003 and a humanized variant of IPN003 (hu-IPN003), but not control IgG2a, inhibited generation of all three anaphylatoxins with similar efficacy (complete inhibition) and potency (~4.5-5.5 µg/mL) compared to hemolysis.

Example 8

Inhibition of C3b Deposition on Red Blood Cells

Four CAD patient plasma samples were tested for their ability to inhibit C3b deposition on hRBCs. Plasma samples from CAD patients P8, P11, P14, and P15 were incubated with IPN003 or control IgG2a; and the percent of C3b-positive cells was determined using flow cytometry. The data are shown in FIGS. 31 and 32. As shown in FIG. 31, 100 µg/mL IPN003, but not control IgG2a, significantly inhibited C3b deposition on the RBC surface. The average inhibition was ~90%. As shown in FIG. 32, CAD plasma-mediated deposition of C3b on hRBCs was inhibited by IPN003, but not by control IgG2a, in a concentration-dependent manner. The $IC_{50}$ for IPN003 was about 6.6 µg/ml.

Example 9

Immunogenic Potential of a Humanized Variant of IPN003

Humanized anti-C1s antibody was assessed for immunogenic potential. An EpiScreen™ assay was used. See, e.g., Jones et al. (2004) *J. Interferon Cytokine Res.* 24:560; and Jones et al. (2005) *J. Thromb. Haemost.* 3:991. Time course T cell assays were performed using CD8⁺-depleted peripheral blood mononuclear cells (PBMC); and T cell proliferation was measured by incorporation of [³H]-thymidine at various time points after addition of test antibody samples. Proliferation responses to a humanized anti-C1s antibody or a chimeric anti-C1s antibody are shown in FIGS. 33A and 33B.

Figure 33A:
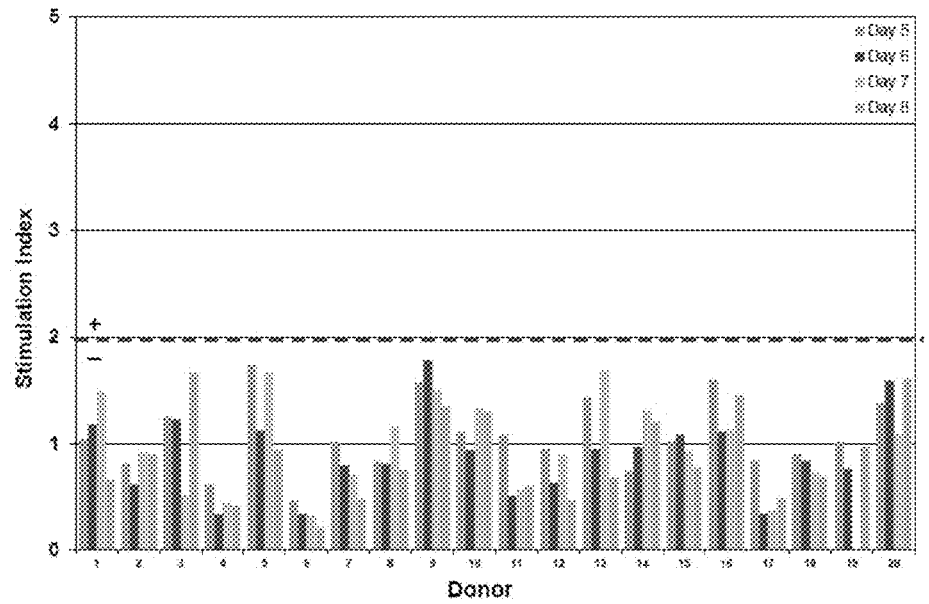
FIGS. 33A and 33B depict proliferation responses to a humanized variant of IPN003 (FIG. 33A) and to a chimeric anti-C1s antibody (FIG. 33B).
Figure 33B:
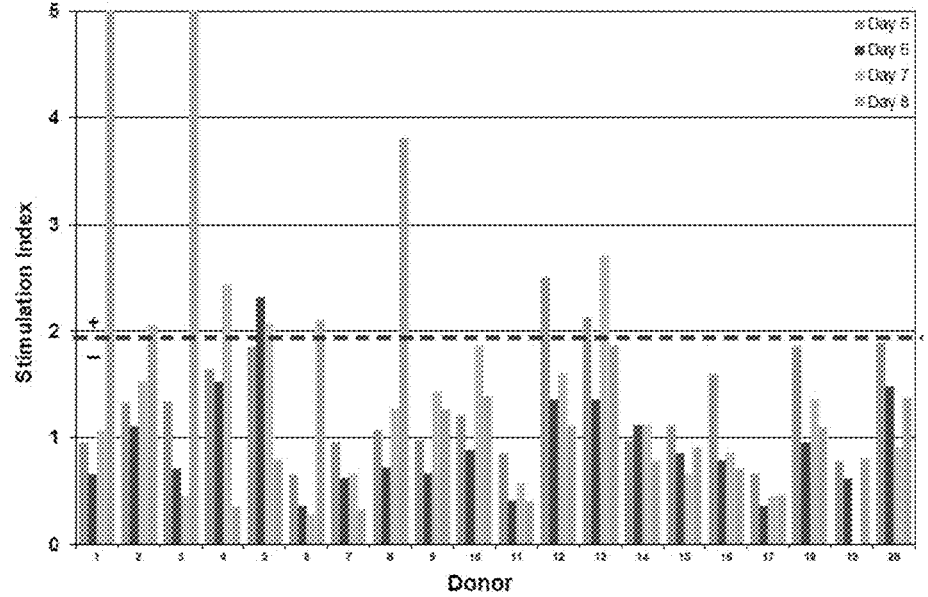

As shown in FIG. 33A, a test fully humanized IPN003 antibody had low immunogenic potential (below the SI threshold of 2.0). FIG. 33B shows results with a reference chimeric antibody, where the reference chimeric antibody has IPN003 murine heavy and light chain variable regions and human IgG4 constant region.

Example 10

Effect of TNT003 on Complement-Dependent, CAD Autoantibody-Mediated Activities The effect of TNT003 on hemolysis, phagocytosis, and C4a generation mediated by autoantibodies present in sera of patients with cold agglutinin disease (CAD) was determined.

The data are shown in FIGS. 34-37.

Figure 34:
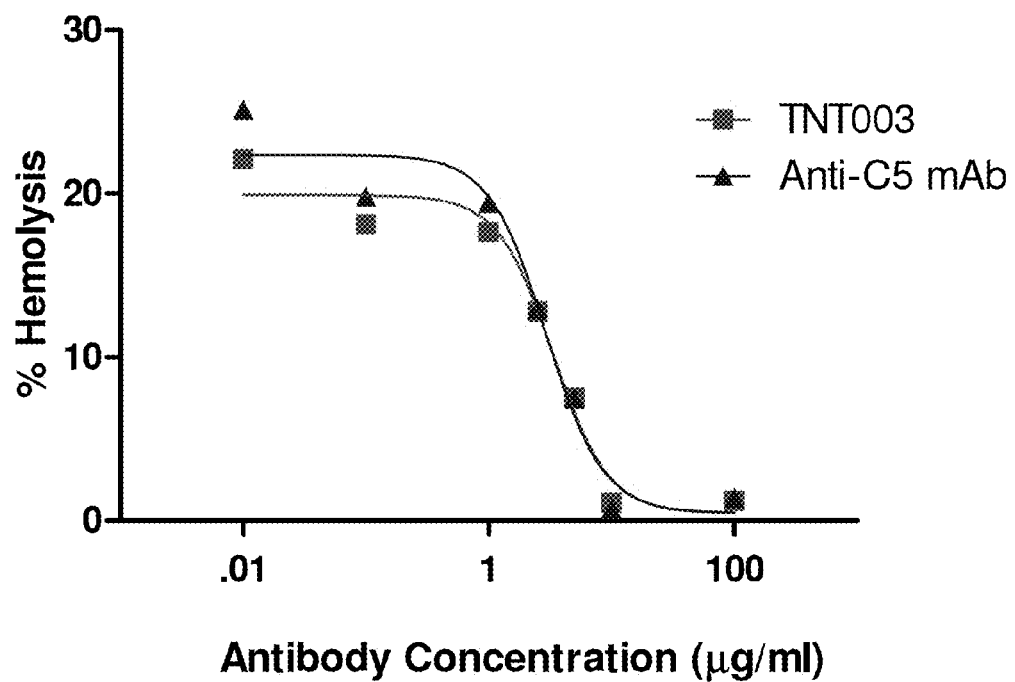
FIG. 34 depicts the effect of TNT003 on complement-dependent hemolysis mediated by autoantibodies present in plasma of patients with cold agglutinin disease (CAD).

As shown in FIG. 34, both TNT003 and an anti-05 mAb prevent complement dependent CAD autoantibody-mediated hemolysis in a concentration-dependent manner. In a 96-well plate, Type O⁻ red blood cells were incubated in the presence of plasma from a CAD patient and 10 mM EDTA to allow for autoantibody binding (45 minutes at 4° C.). Cells were then washed with GVB++ (GVB with Ca++ and Mg++) buffer. GVB++ buffer: 0.1% gelatin, 5 mM Veronal, 145 mM NaCl, 0.025% $NaN_3$, pH 7.3. Containing 0.15 mM calcium chloride and 0.5 mM magnesium chloride Fresh normal human serum (25% final concentration in GVB++) and varying concentrations of either TNT003 or an anti-05 mAb were then added to the cells and allowed to incubate for 1 hr at 17° C. Following incubation, 50 µL of GVB++ was added to each well to stop the reaction. The 96-well plate was then centrifuged and a portion of the supernatant collected and transferred to a new 96-well plate. Peak absorbance values (540 nm) were read on a microplate reader. A well that contained 10 mM EDTA instead of antibody was used as a control well to determine non-complement mediated hemolysis (positive control). The absorbance value from this well was subtracted from all other wells to determine the extent of complement-dependent lysis. Similarly, a control well without antibody was used to determine maximal complement dependent hemolysis (negative control).

Figure 35:
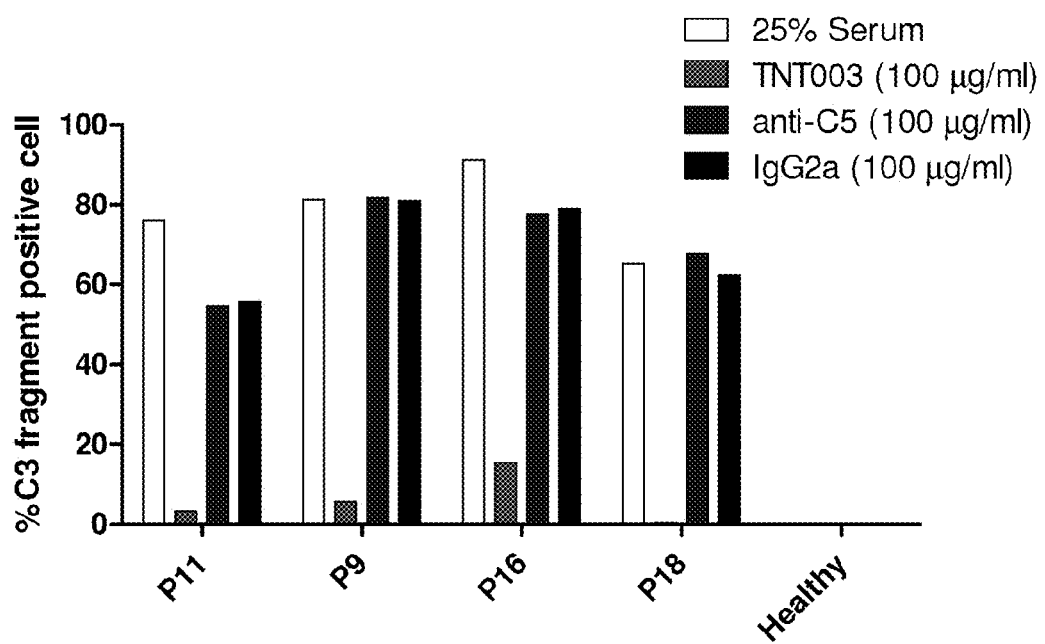
FIG. 35 depicts the effect of TNT003 on complement-dependent C3b deposition mediated by autoantibodies present in plasma of patients with CAD.

As shown in FIG. 35, TNT003, but not an anti-05 mAb nor a control mouse IgG2a antibody, inhibited C3b deposition mediated by CAD autoantibodies. In a 96-well plate, Type O$^-$ red blood cells were incubated in the presence of plasma and 10 mM EDTA from a CAD patient or healthy normal plasma (negative control) to allow for autoantibody binding (45 minutes at 4° C.). Cells were then washed with GVB++ buffer. Fresh normal human serum (25% final concentration in GVB++) and 100 µg/mL of TNT003, a mouse IgG2a control Ab, or an anti-05 mAb were then added to the cells and allowed to incubate for 1 hr at 17° C. Cells were then washed with FACS buffer (2×). FACS buffer: phosphate-buffered saline (PBS) w/o+0.5% bovine serum albumin (BSA)+0.1% $NaN_3$). FACS buffer is the buffer in which cells and antibodies are incubated prior to running in a flow cytometer. Cells were then incubated in the presence of a mouse anti human C3b monoclonal antibody (1 hr, 4° C.). Cells were then washed with FACS buffer (3×) and incubated with a secondary antibody (Alexa Fluor 488 conjugated goat anti-mouse IgG1) at room temperature for 30 minutes. Cells were then washed with FACS buffer (3×) and fluorescence read out at 488 nm on a flow cytometer.

Figure 36:
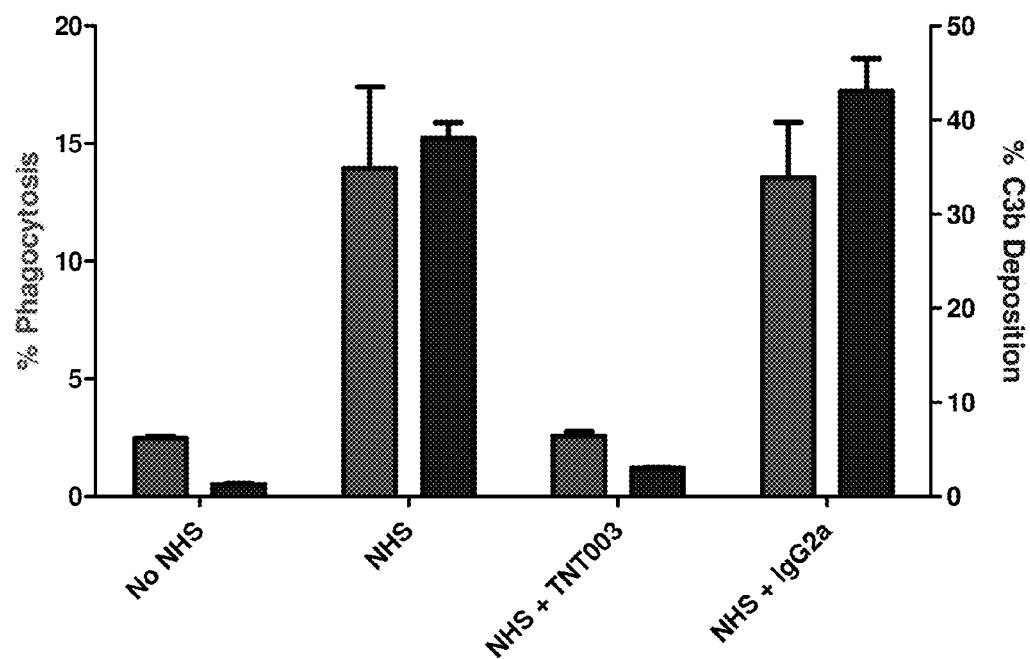
FIG. 36 depicts the effect of TNT003 on complement-dependent phagocytosis mediated by autoantibodies present in plasma of patients with CAD.

As shown in FIG. 36, TNT003 prevented complement-mediated phagocytosis induced by CAD autoantibodies. To understand the effect of CAD autoantibody-mediated complement deposition on RBC phagocytosis, a phagocytosis assay was developed using the THP-1 monocytic cell line. Type O-human RBC were labeled with Cell Tracker Green and sensitized with CAD autoantibodies by incubating in the presence of CAD patient plasma and 10 mM EDTA overnight (4° C.). Following washout of CAD plasma, normal human serum (NHS; final concentration 25%) and either 100 µg/mL TNT003 or 100 µg/mL IgG2a control Ab was added (1 hr at 17°C.). Retinoic acid treated THP-1 cells (3 µM, 3 days) were then plated in a 96 well plate (1×10^5 cells/well) and treated with FcX. FcX is a reagent used to prevent activation of FcgR, a potential confounding factor in the phagocytosis assay as FcgR can mediate phagocytosis as well; see, e.g., www(dot)biolegend(dot)com. The hRBC were then added to the THP-1 cells at 5×10^6 cells/well for 2 hr at 37° C. to allow for phagocytosis (red bars). Phagocytosis was determined by flow cytometer and expressed as a percentage of THP-1 cells containing Cell Tracker Green-labeled RBC. A portion of the hRBC was also taken to stain with an anti C3b Ab to quantify C3b deposition by FACS analysis as described above (blue bars).

It was found that hRBC coated with CAD autoantibodies but not incubated in the presence of NHS had very low levels of membrane bound C3b and were not readily phagocytosed by THP-1 cells (No NHS). Upon exposure to 25% NHS, C3b deposition increased ~30 fold and phagocytosis by ~5 fold (NHS). 100 µg/mL TNT003, but not IgG2a control antibody, inhibited both C3b deposition and phagocytosis to baseline levels, providing evidence that TNT003 can prevent CAD autoantibody-mediated RBC phagocytosis. Data presented are the average of two independent experiments preformed with one patient sample (P18), and are representative of results generated from 5 different CAD patient samples.

Figure 37A:
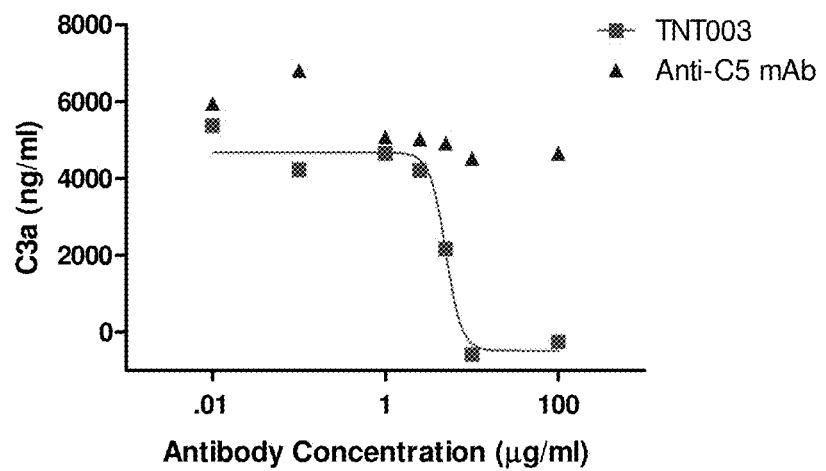
FIGS. 37A-C depict the effect of TNT003 on complement-dependent C3a, C4a and C5a generation mediated by autoantibodies present in plasma of patients with CAD.
Figure 37B:
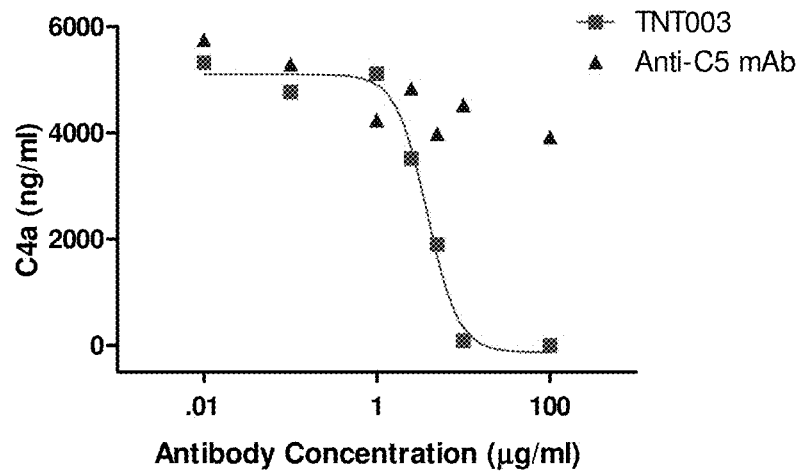
Figure 37C:
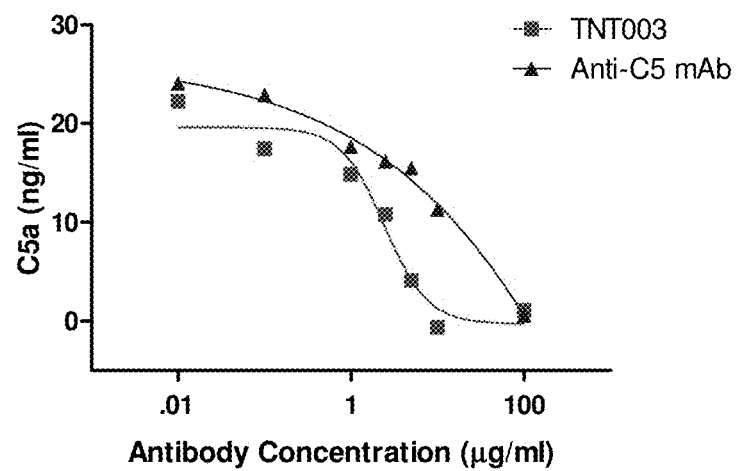

As shown in FIG. 37A and FIG. 37B, TNT003, but not an anti-05 mAb, prevents C3a and C4a generation by CAD autoantibodies. As shown in FIG. 37C, both TNT003 and an anti-05 mAb are able to inhibit CAD autoantibody-mediated C5a generation. Commercially available ELISA kits were used to detect and quantify C3a, C4a, and C5a from the supernatants of the experiments described above. C3a, C4a and C5a levels in the human serum used as a complement source were subtracted as background.

Example 11

In Vivo Effects of TNT003

In vivo effects of TNT003 were tested in a non-human primate. The data are shown in FIGS. 38 and 39.

Figure 38A:
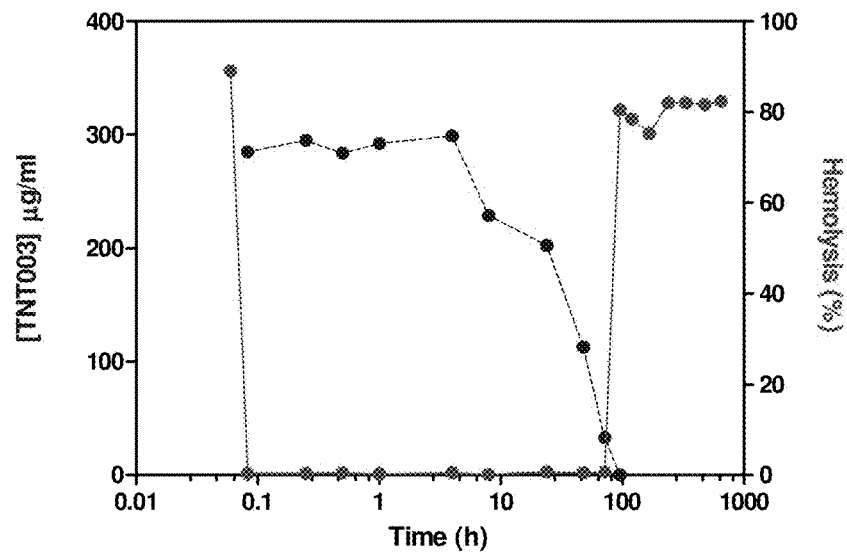
FIGS. 38A and 38B depict the ex vivo activity of TNT003 on hemolysis and C3b deposition following administration to non-human primates.
Figure 38B:
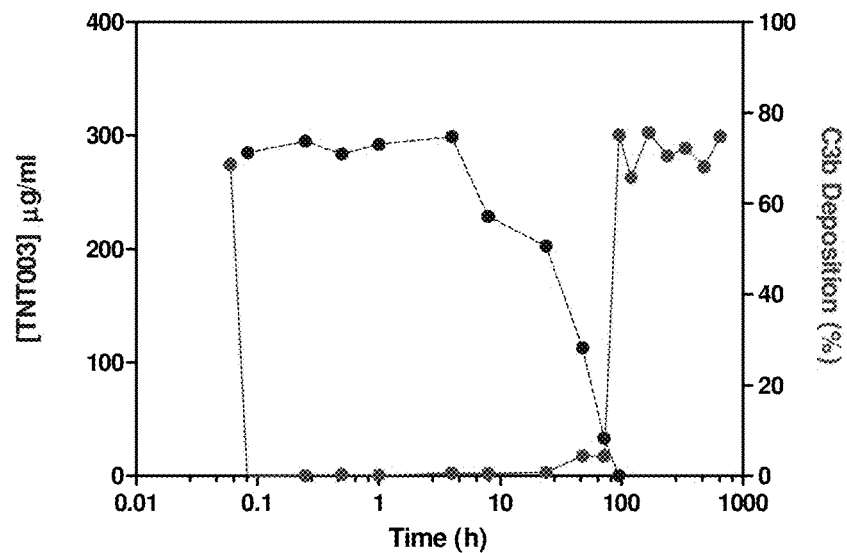

As shown in FIG. 38, TNT003-containing sera from cynomolgus monkeys given a single i.v. dose of TNT003 (30 mg/kg) were unable to induce complement-dependent hemolysis or deposit C3b on the plasma membrane of IgM-sensitized sheep red blood cells. Sera taken from monkeys before and after i.v. injection at various time points were used as a source of complement for inducing hemolysis of IgM-sensitized sheep red blood cells. Final serum concentration was 1.25%. As depicted in FIG. 38A, immediately following i.v. injection of TNT003, sera samples obtained from the monkeys were unable to hemolyse IgM-sensitized sheep red blood cells in all samples containing detectable TNT003 levels (up to and including 72 hours; plotted on the right Y-axis). At 96 hours, TNT003 fell below detectable levels (as determined by an ELISA capture assay; plotted on the left Y-axis) at which point serum hemolytic capacity was restored to pre-bleed levels. FACS assays designed to detect the presence of membrane-bound C3b (FIG. 38B) show that TNT003 containing sera also fail to deposit C3b on the plasma membrane of IgM-sensitized sheep red blood cells. These data suggest that TNT003 is present at efficacious levels following in vivo administration to inhibit the classical complement pathway in ex vivo hemolysis assays.

Figure 39:
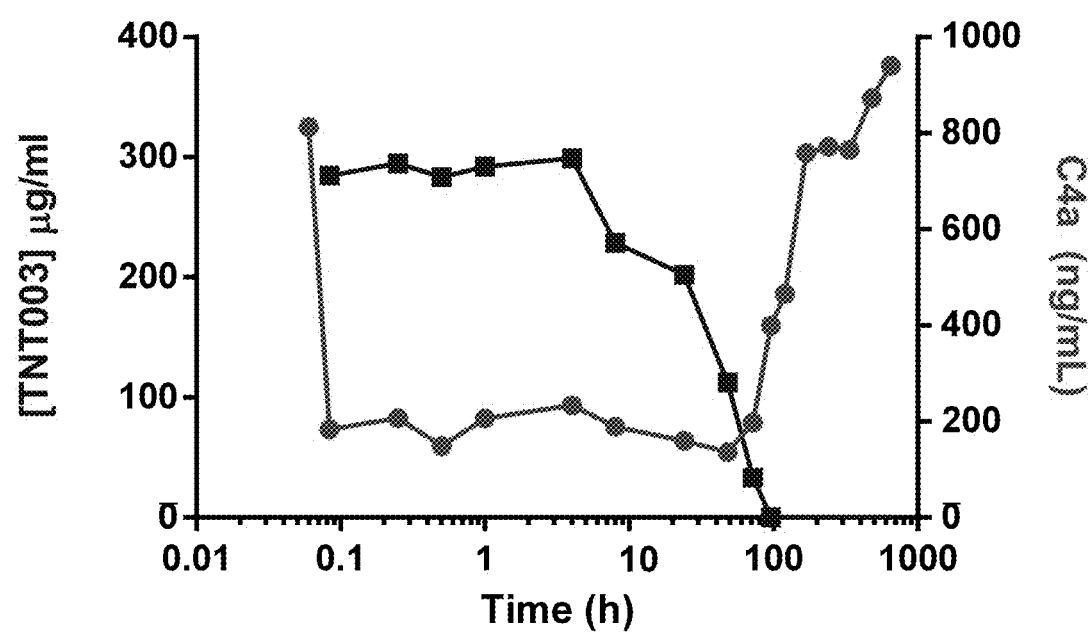
FIG. 39 depicts the in vivo effect of TNT003 on C4a generation following administration to non-human primates.

As shown in FIG. 39, TNT003 inhibits in vivo C4a generation in cynomolgus monkeys given a single i.v. dose of TNT003 (30 mg/kg). C4a concentrations in serum samples taken from TNT003-dosed monkeys were determined using commercially available ELISA kits (plotted on the right Y-axis). The data show that C4a levels drop by approximately 90% immediately following TNT003 administration and remain low in all samples containing detectable TNT003 (up to and including 72 hours). At 96 hours, TNT003 fell below detectable levels (as determined by an ELISA capture assay; plotted on the left Y-axis) at which point serum C4a were restored to pre-bleed levels. These data provide evidence that TNT003 is active in vivo and upon 30 mg/kg administration, reaches levels that inhibit classical pathway activity in the cynomolgus monkey.

Example 12

TNT003 Epitope Mapping

Figure 40:
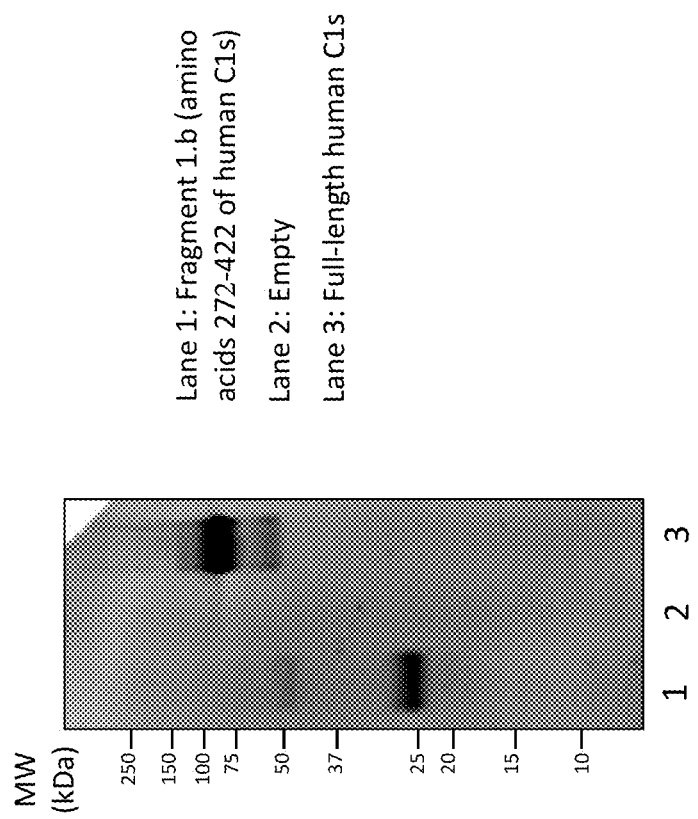
FIG. 40 depicts binding of TNT003 to human C1s fragments.

To identify the minimal region of human C1s (hC1s) required for TNT003 binding, full-length hC1s and N-terminal and C-terminal truncations of hC1s were expressed in HEK293 cells. Recombinant proteins were purified by affinity chromatography and analyzed by western blots of non-reduced SDS-PAGE gels. As shown in FIG. 40, a fragment (hC1s fragment 1.b), consisting of amino acids 272-422 that specifically bound TNT003, was identified. Additional N-terminal and C-terminal truncations of this amino acid fragment eliminated binding of TNT003.

FIG. 40. Identification of the minimal human C1s fragment required for TNT003 binding. Full-length or fragments of C1s were expressed in HEK293 cells. Proteins were purified by affinity chromatography and analyzed by western blot of non-reduced SDS-PAGE gels with TNT003. TNT003 binds to full-length C1s (Lane 3) and a fragment of C1s (fragment 1.b) containing amino acids 272-422 of the C1s A-chain.

Figure 41:
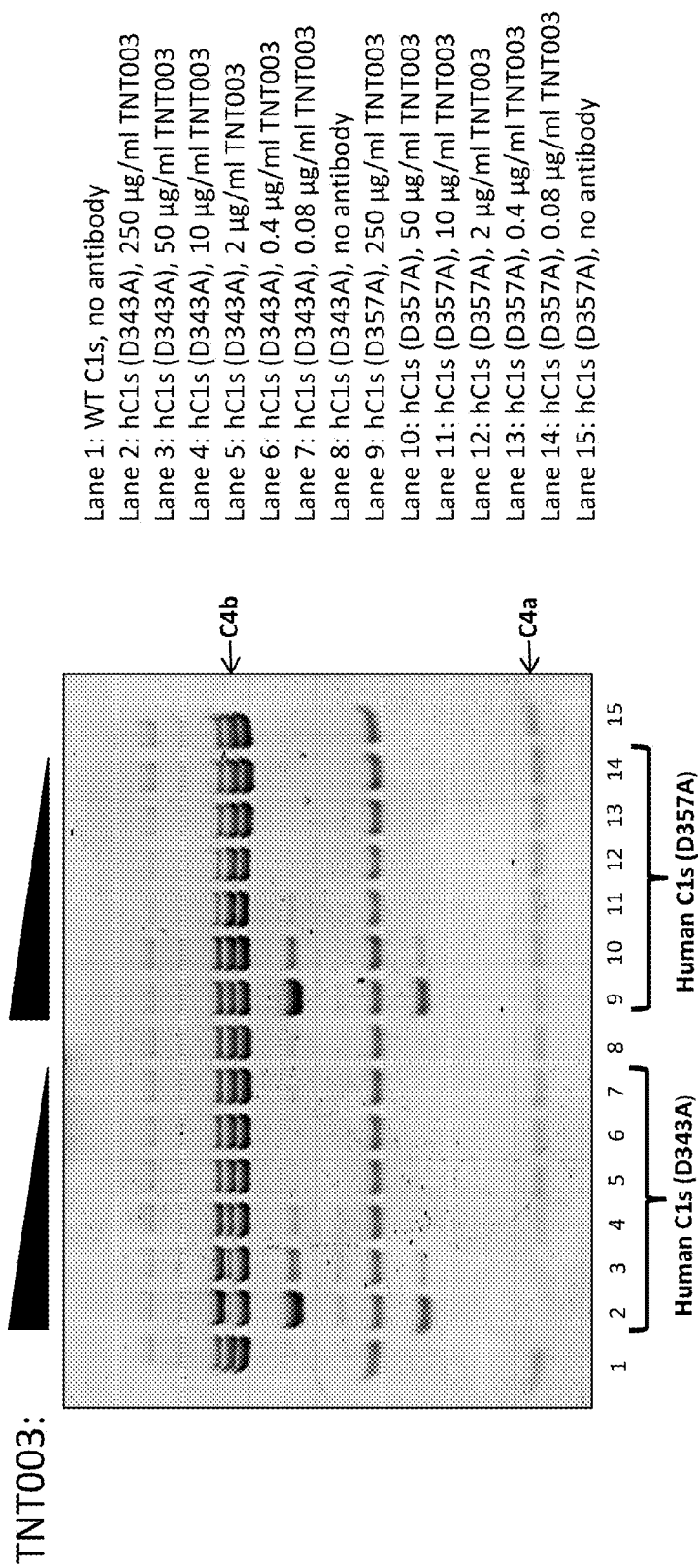
FIG. 41 depicts the effect of mutation of D343 and D357 on inhibition of C1s activity by TNT003.

To further identify the epitope of TNT003 in full-length human C1s, alanine scanning mutagenesis was performed using standard techniques. Mutation of amino acid 357 (aspartic acid) to alanine significantly decreased binding of TNT003 to human C1s. Importantly, as shown in FIG. 41, this mutation had no significant effect on the catalytic activity of C1s and did not alter its ability to cleave its substrate, C4, suggesting that the protein was correctly folded. However, in contrast to its effect on wild-type C1s, TNT003 was unable to inhibit the activity of this mutant C1s, even at high concentrations. Taken together, these data suggest that the epitope of TNT003 contains aspartic acid 357 and that this amino acid is critical to the binding and inhibitory activity of the antibody.

FIG. 41: Identification of a specific amino acid (aspartic acid 357) required for TNT003 binding to human C1s. Alanine scanning mutagenesis of human C1s was performed using standard techniques. Each C1s mutant protein was expressed in HEK293 cells and purified by affinity chromatography. To measure enzymatic activity each mutant C1s protein was incubated with purified human C4 for 1 h at 37° C. in the presence or absence of TNT003. Reactions were analyzed by SDS-PAGE to identify C4 cleavage products (C4a and C4b). Mutation of aspartic acid 357 eliminated the ability of TNT003 to inhibit C1s activity. In contrast, mutation of aspartic acid 343 to alanine had no effect on C1s enzymatic activity, or the ability of TNT003 to inhibit

Example 13

TNT003 Avidity

Figure 42:
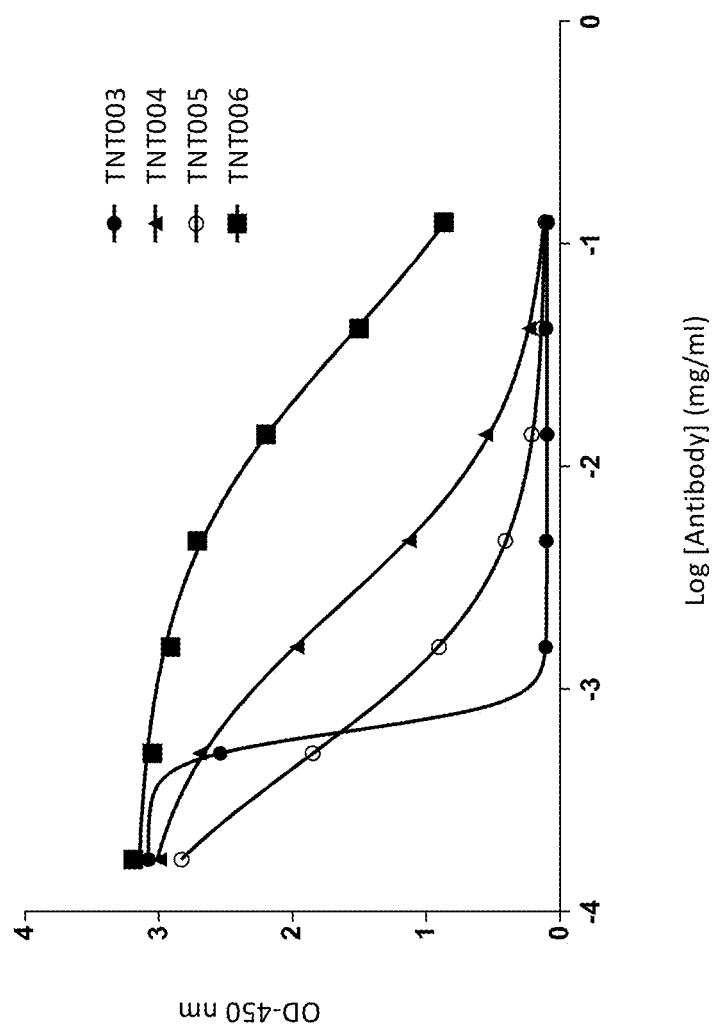
FIG. 42 depicts inhibition of human C1s activity by TNT003.

TNT003 is a potent inhibitor of C1s activity both in purified systems and in functional assays—for example red blood cell hemolysis. The activity of TNT003 was compared to other C1s antibodies in a plate based C4 deposition assay (FIG. 42). TNT003 was a more potent inhibitor of C1s activity than other anti-C1s antibodies (TNT004, TNT005, TNT006; anti-C1s antibodies that inhibit C1s protease activity)—even if the other anti-C1s antibodies bound to C1s with higher affinity. These data suggested that the potency of TNT003 was mediated in part by its avidity for C1s within the C1 complex and that a single molecule of TNT003 could contact (and therefore inhibit) both C1s molecules simultaneously.

FIG. 42: TNT003 is a potent inhibitor of human C1 s activity. Wells of a 96-well plate were coated with human IgM antibodies and non-specific binding blocked using gelatin. Human serum (final concentration 1.25%) was added to the wells in the presence or absence of increasing concentrations of antibody and incubated for 1 h at 37° C. The amount of C4 deposited on the plate was measured using a biotinylated anti-human C4 antibody and a streptavidin-HRP conjugate.

Figures 43A, 43B:
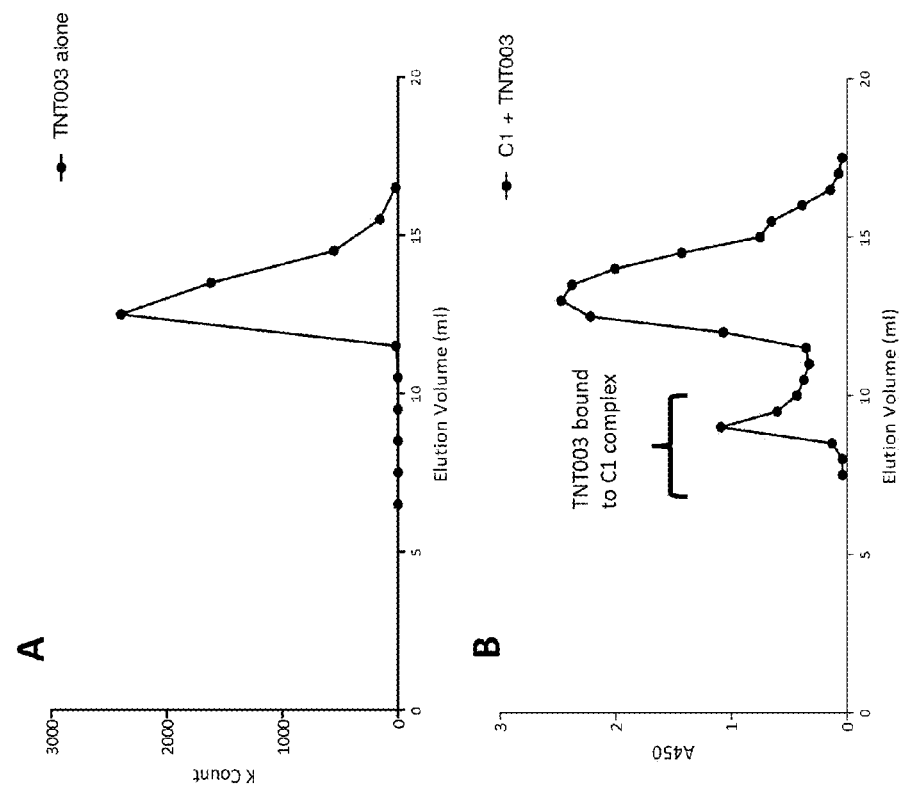
FIGS. 43A and 43B depict TNT003 binding to C1s present in a C1 complex.

To demonstrate that TNT003 could bind the C1 complex, biotin-labeled TNT003 was incubated with purified C1 complex and the reaction was fractionated on a Sepharose Superdex-200 column. As shown in FIG. 43B, C1 bound TNT003 to form a complex with a molecular weight consistent with a single TNT003 antibody binding to each C1 complex.

FIGS. 43A and 43B: TNT003 binds to the C1 complex. TNT003 was biotin-labeled and incubated with purified human C1 complex. The reaction was fractionated on a Sepharose Superdex-200 column and each fraction analyzed for the presence of TNT003 by western blotting. As shown in FIG. 43A, TNT003 alone eluted as a single peak. In contrast, following incubation with purified C1 complex, a second peak was observed, consistent with the formation of a TNT003:C1 complex (FIG. 43B).

Figure 44:
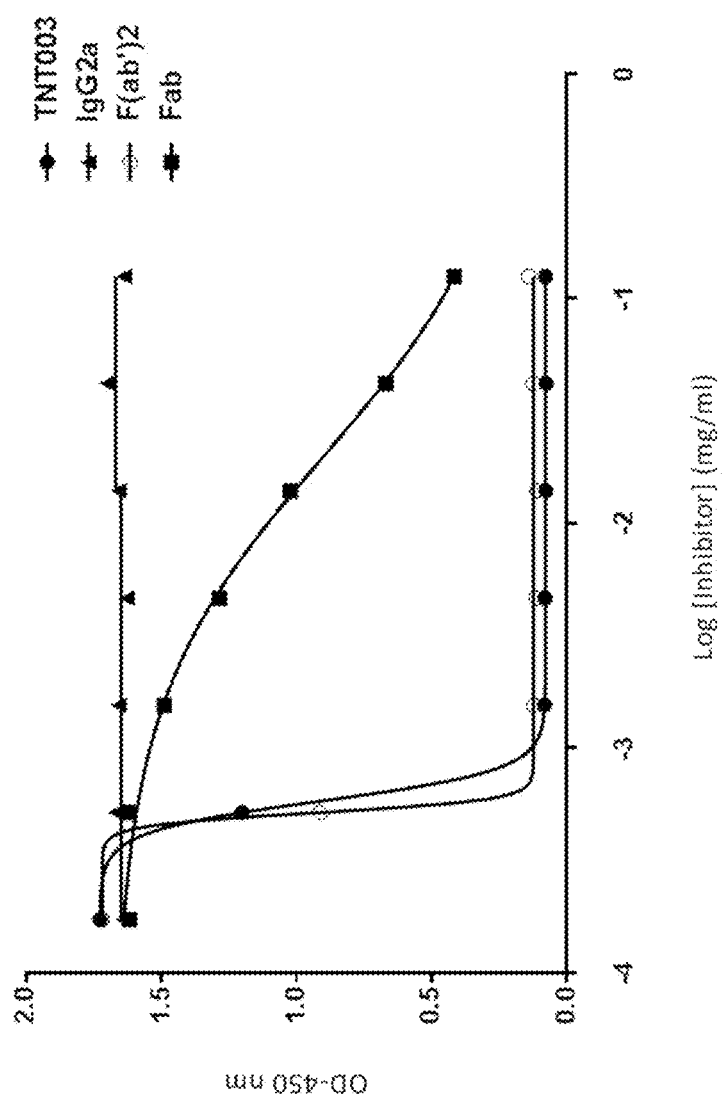
FIG. 44 depicts inhibition of human C1s by TNT003 and fragments of TNT003

To further characterize the mechanism of inhibition, the ability of TNT003, the TNT003 F(ab')$_2$ fragment, and the TNT003 Fab fragment, to inhibit C1s activity was measured. As shown in FIG. 44, TNT003 and the TNT003 F(ab')$_2$ fragment inhibited C1s activity with equal activity. In contrast, the TNT003 Fab fragment was a much less potent inhibitor of C1s activity. Taken together, these data suggest that the potent activity of TNT003 is related, at least in part, to the bivalent nature of the antibody (and F(ab')$_2$ fragment) and that the antibodies ability to inhibit C1s has a significant avidity component.

FIG. 44: TNT003 and the TNT003 Fab'2 fragment are more potent inhibitors of C1s activity than the TNT003 Fab. Wells of a 96-well plate were coated with human IgM antibodies and non-specific binding blocked using gelatin. Human serum (final concentration 1.25%) was added to the wells in the presence or absence of increasing concentrations of TNT003 or F(ab')$_2$ and Fab fragments of TNT003 and incubated for 1 h at 37° C. The amount of C4 deposited on the plate was measured using a biotinylated anti-human C4 antibody and a streptavidin-HRP conjugate.

Example 14

TNT003 Binding Characteristics

Figure 45:
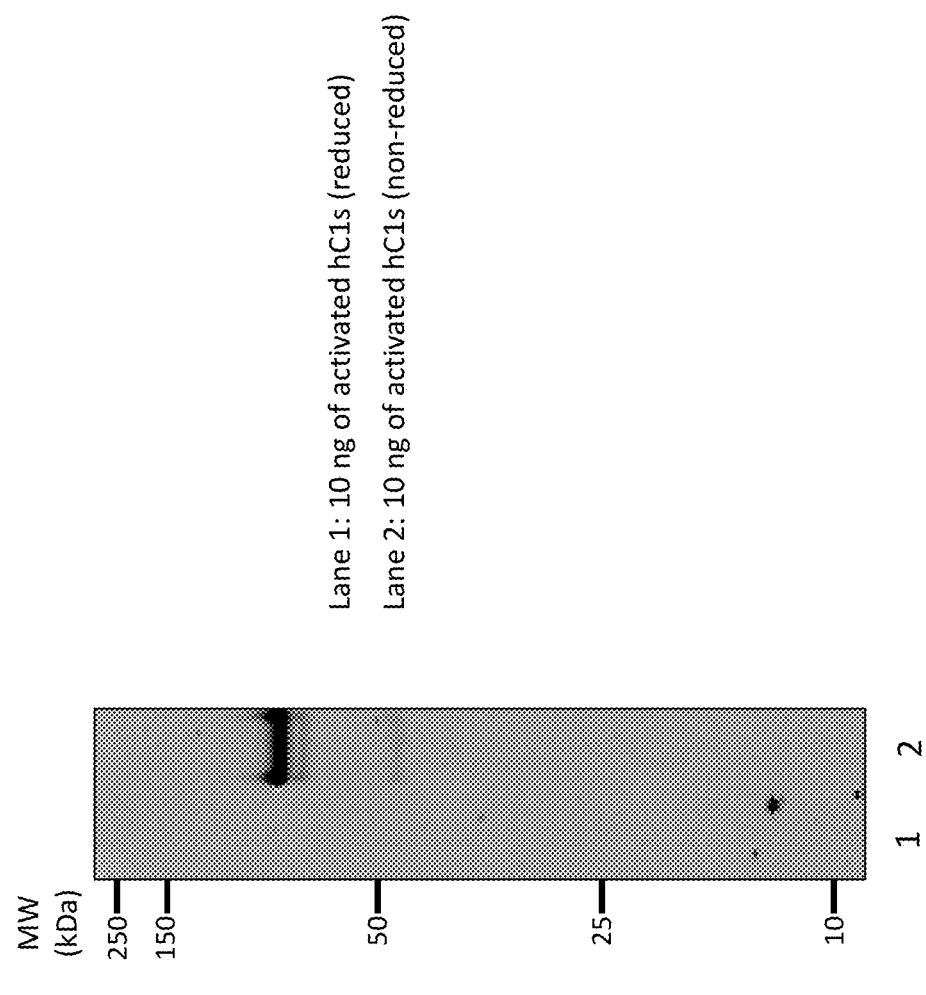
FIG. 45 depicts binding of TNT003 to human C1s under non-reducing conditions.

To determine whether TNT003 could bind C1s under reducing and non-reducing conditions, western blots on SDS-PAGE gels were performed with reduced and non-reduced activated human C1s. As shown in FIG. 45, TNT003 only binds to C1s under non-reducing conditions, consistent with the antibody binding to a conformation specific epitope within C1s.

FIG. 45: TNT003 specifically binds human C1s under non-reducing conditions. Activated human C1s was fractionated by SDS-PAGE under reducing and non-reducing conditions and western blotted with TNT003. TNT003 only binds C1s under non-reducing conditions suggesting that it binds to a conformation dependent epitope.

Figure 46:
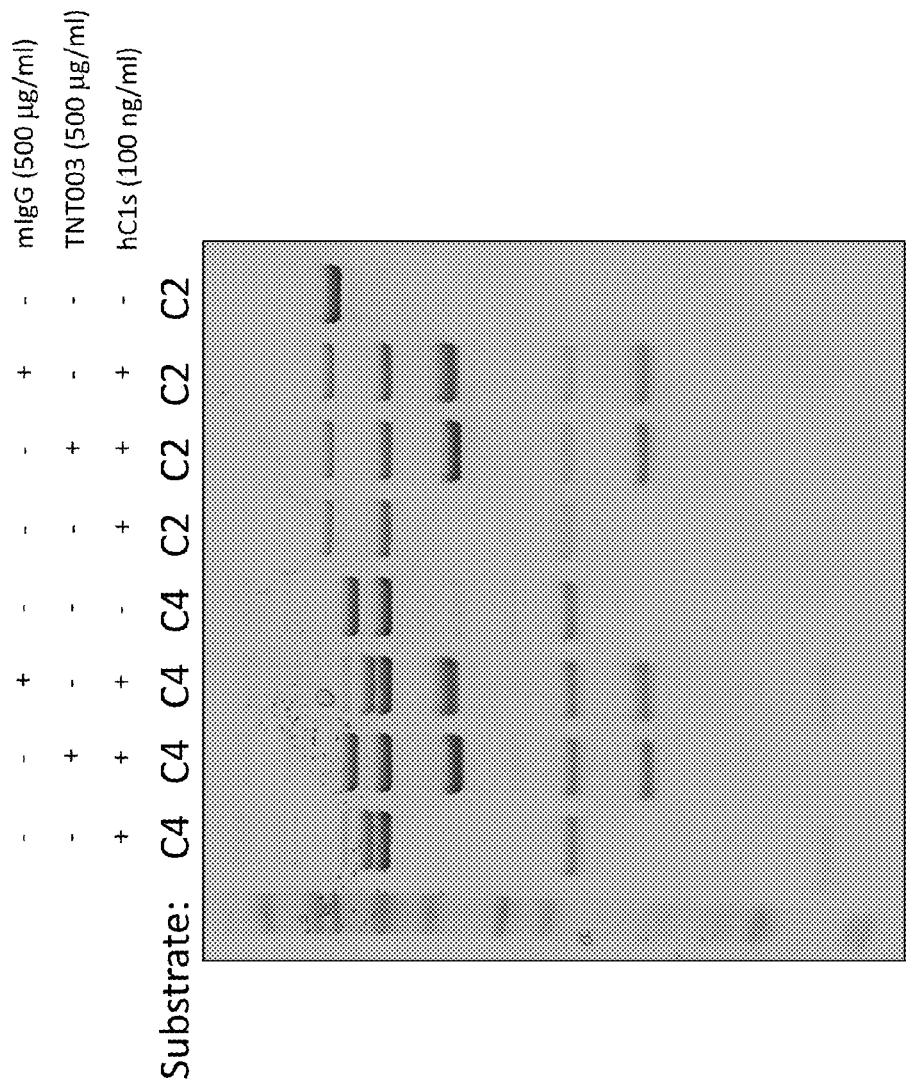
FIG. 46 depicts inhibition of activation of complement C4, but not complement C2, by TNT003.

To determine whether TNT003 inhibits complement C2 or complement C4 activation, purified C1s was incubated with C2 or C4 in the presence or absence of TNT003. As shown in FIG. 46, TNT003 specifically inhibited C1s activation of C4 but not C1s activation of C2, consistent with TNT003 being a competitive inhibitor of C4 binding to C1s rather than an inhibitor of the C1s serine protease domain.

FIG. 46: TNT003 inhibits C1s activation of complement C4 but not complement C2. Purified human C1s was incubated with either human complement C2 or human complement C4 for 3 h at 37° C. Reaction products were separated on SDS-PAGE gels. TNT003 specifically inhibited activation of human complement C4, but not complement C2, by human C1s.

Example 15

C1s Determination

C1s levels were measured in patient samples by ELISA. High binding plates (Costar, 3590) were coated with 100 μl of 5 μg/ml rabbit polyclonal antibody to C1s (Abcam, ab87986) in 1×dPBS (Life Technologies, 14190-144) overnight. Blocking was performed by adding 1% gelatin (Sigma-Aldrich, G2500) in 1×dPBS for 3 hours. These plates were then stored at 4° C. Prior to use, the plates were incubated at 37° C. for 15 minutes. After washing the plates with Buffer A (1×dPBS containing 0.01% Tween 20, and 20 mM EDTA), serially diluted human serum in Buffer A or purified C1s in Buffer A was added to the wells. After incubating for 1 hour at ambient temperature, the wells were washed three times with buffer A. Each well was incubated with 100 μl of 1 μg/ml biotinylated TNT003 (diluted in Buffer A) for 1 hour then washed three times with buffer A. The wells were further incubated with 5000 fold diluted streptavidin-coupled horse radish peroxidase (HRP) (SouthernBiotech, 7100-05)(diluted in Buffer A) for 10 minutes. After washing four times with buffer A, enzymatic color development was achieved using TMB (Thermo Scientific, 34029) and the reaction was stopped using 1 M sulfuric acid. The absorbance at 450 nm was measured.

Figure 47:
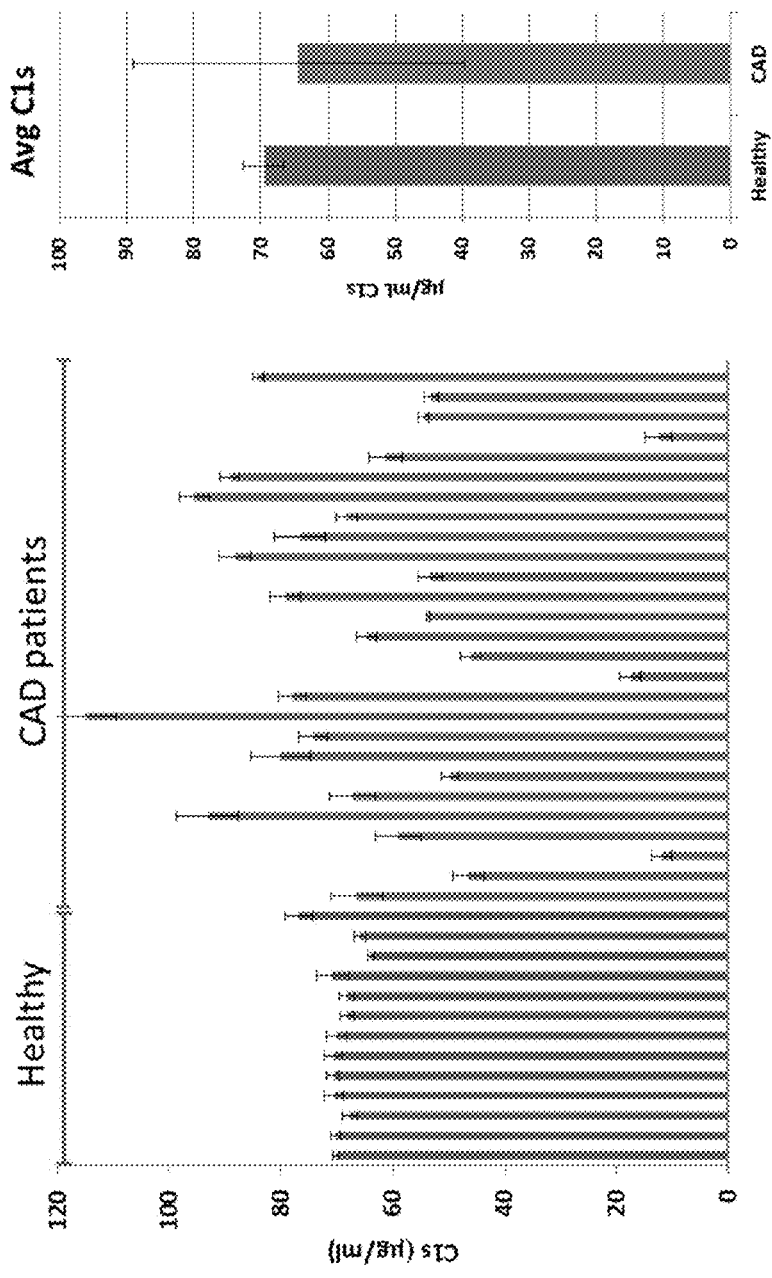
FIG. 47 depicts C1s levels in plasma samples from healthy volunteers and from CAD patients.

The results are shown in FIG. 47. FIG. 47 compares the C1s concentrations in the plasma samples of healthy volunteers (green; n=13) versus CAD patients (gray; n=27). It was found that, on average, C1s concentrations were comparable between healthy individuals and CAD patients. These data provide a rationale for using similar dose levels and dosing regimens for a C1s inhibitor to obtain target coverage in either healthy or CAD patients in Phase I trials.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto.

---

What is claimed is:

1. A container comprising a composition comprising a humanized antibody that binds complement C1s protein and comprises light chain complementarity determining regions (CDRs) of an antibody light chain variable region comprising amino acid sequence SEQ ID NO:7 and heavy chain CDRs of an antibody heavy chain variable region comprising amino acid sequence SEQ ID NO:8.

2. The container of claim 1, wherein the container is sterile.

3. The container of claim 1, wherein the container is a vial.

4. The container of claim 1, wherein the container is a bottle.

5. The container of claim 1, wherein the container is a syringe.

6. The container of claim 1, wherein the composition comprises a pharmaceutically acceptable excipient.

7. The container of claim 1, wherein the humanized antibody comprises a humanized light chain framework region.

8. The container of claim 1, wherein the humanized antibody comprises a humanized heavy chain framework region.

9. The container of claim 1, wherein the humanized antibody comprises a humanized light chain framework region and a humanized heavy chain framework region.

10. The container of claim 1, wherein the humanized antibody comprises a heavy chain constant region of the isotype IgG1, IgG2, IgG3, or IgG4.

11. The container of claim 1, wherein the humanized antibody is selected from the group consisting of a Fab fragment, a F(ab')$_2$ fragment, a scFv, and a Fv.

12. A lyophilized composition comprising a humanized antibody that binds complement C1s protein and comprises light chain complementarity determining regions (CDRs) of an antibody light chain variable region comprising amino acid sequence SEQ ID NO:7 and heavy chain CDRs of an antibody heavy chain variable region comprising amino acid sequence SEQ ID NO:8.

13. The lyophilized composition of claim 12, comprising a lyoprotectant.

14. The lyophilized composition of claim 12, wherein the humanized antibody comprises a humanized light chain framework region.

15. The lyophilized composition of claim 12, wherein the humanized antibody comprises a humanized heavy chain framework region.

16. The lyophilized composition of claim 12, wherein the humanized antibody comprises a humanized light chain framework region and a humanized heavy chain framework region.

17. The lyophilized composition of claim 12, wherein the humanized antibody comprises a heavy chain constant region of the isotype IgG1, IgG2, IgG3, or IgG4.

18. The lyophilized composition of claim 12, wherein the humanized antibody is selected from the group consisting of a Fab fragment, a F(ab')$_2$ fragment, a scFv, and a Fv.

19. A composition comprising:
  a) a humanized antibody comprising:
    i) a light chain variable region comprising a complementarity-determining region (CDR) comprising a CDR-L1 having the amino acid sequence of SEQ ID NO:1, a CDR-L2 having the amino acid sequence of SEQ ID NO:2, a CDR-L3 having the amino acid sequence of SEQ ID NO:3; and ii) a heavy chain variable region comprising a CDR comprising a CDR-H1 having amino acid sequence SEQ ID NO:4, a CDR-H2 having amino acid sequence SEQ ID NO:5, and a CDR-H3 having amino acid sequence SEQ ID NO:6; and b) a pharmaceutically acceptable excipient.

20. The composition of claim 19, wherein the composition comprises one or more of a tonicity agent, a suspending agent, an emulsifying agent, a stabilizer, a preservative, a lyoprotectant, a surfactant, and a sugar.

21. The composition of claim 19, wherein the composition comprises a tonicity agent.

22. The composition of claim 19, wherein the composition comprises a suspending agent.

23. The composition of claim 19, wherein the composition comprises an emulsifying agent.

24. The composition of claim 19, wherein the composition comprises a stabilizer.

25. The composition of claim 19, wherein the composition comprises a preservative.

26. The composition of claim 19, wherein the composition comprises a lyoprotectant.

27. The composition of claim 19, wherein the composition comprises a surfactant.

28. The composition of claim 19, wherein the composition comprises a sugar.

29. The composition of claim 28, wherein the sugar is trehalose or sucrose.

30. The composition of claim 19, wherein the humanized antibody comprises a humanized light chain framework region.

31. The composition of claim 19, wherein the humanized antibody comprises a humanized heavy chain framework region.

32. The composition of claim 19, wherein the humanized antibody comprises a humanized light chain framework region and a humanized heavy chain framework region.

33. The composition of claim 19, wherein the humanized antibody comprises a heavy chain constant region of the isotype IgG1, IgG2, IgG3, or IgG4.

34. The composition of claim 19, wherein the humanized antibody is selected from the group consisting of a Fab fragment, a F(ab')₂ fragment, a scFv, and a Fv.

35. A composition comprising:
a) a humanized antibody that binds complement C1s protein and comprises light chain complementarity-determining regions (CDRs) of an antibody light chain variable region comprising amino acid sequence SEQ ID NO:7 and heavy chain CDRs of an antibody heavy chain variable region comprising amino acid sequence SEQ ID NO:8, wherein the humanized antibody comprises a humanized light chain framework region; and b) a pharmaceutically acceptable excipient.

36. The composition of claim 35, wherein the humanized antibody comprises a humanized heavy chain framework region.

37. The composition of claim 35, wherein the humanized antibody comprises a heavy chain constant region of the isotype IgG1, IgG2, IgG3, or IgG4.

38. The composition of claim 35, wherein the humanized antibody is selected from the group consisting of a Fab fragment, a F(ab')₂ fragment, a scFv, and a Fv.

39. A composition comprising:
a) a humanized antibody that binds complement C1s protein and comprises light chain complementarity-determining regions (CDRs) of an antibody light chain variable region comprising amino acid sequence SEQ ID NO:7 and heavy chain CDRs of an antibody heavy chain variable region comprising amino acid sequence SEQ ID NO:8, wherein the humanized antibody comprises a humanized heavy chain framework region; and b) a pharmaceutically acceptable excipient.

40. The composition of claim 39, wherein the humanized antibody comprises a humanized light chain framework region.

41. The composition of claim 39, wherein the humanized antibody comprises a heavy chain constant region of the isotype IgG1, IgG2, IgG3, or IgG4.

42. The composition of claim 39, wherein the humanized antibody is selected from the group consisting of a Fab fragment, a F(ab')₂ fragment, a scFv, and a Fv.

43. A humanized antibody that binds complement C1s protein and comprises an antibody heavy chain variable region comprising amino acid sequence SEQ ID NO:8 comprising one or more humanized heavy chain framework regions.

44. The humanized antibody of claim 43, wherein the humanized antibody comprises a humanized light chain framework region.

45. The humanized antibody of claim 43, wherein the humanized antibody comprises a heavy chain constant region of the isotype IgG1, IgG2, IgG3, or IgG4.

46. The humanized antibody of claim 43, wherein the humanized antibody is selected from the group consisting of a Fab fragment, a F(ab')₂ fragment, a scFv, and a Fv.

47. A composition comprising:
a) the humanized antibody of claim 43; and
b) a pharmaceutically acceptable excipient.

* * * * *